US006033847A

United States Patent [19]
Sherr et al.

[11] Patent Number: 6,033,847
[45] Date of Patent: Mar. 7, 2000

[54] INK4C-P18 AND INK4D-P19, INHIBITORS OF CYCLIN-DEPENDENT KINASES CDK4 AND CDK6, AND USES THEREOF

[75] Inventors: Charles J. Sherr, Memphis; James Downing, Cordova; Hiroshi Hirai; Tsukasa Okuda, both of Memphis, all of Tenn.

[73] Assignee: St. Jude Children's Research Hospital, Memphis, Tenn.

[21] Appl. No.: 08/384,106

[22] Filed: Feb. 6, 1995

[51] Int. Cl.$^7$ .............................. C12Q 1/68; C07H 21/00; C12N 15/12; C12N 15/85; C07K 14/435

[52] U.S. Cl. .............................. 435/6; 435/69.1; 435/375; 435/455; 536/23.1; 536/23.5; 530/350

[58] Field of Search .................................. 530/23.1, 23.5, 530/350; 435/6, 69.1, 325, 375, 455; 514/44; 935/34; 536/23.1, 23.5

[56] References Cited

U.S. PATENT DOCUMENTS

| | | | |
|---|---|---|---|
| 4,965,188 | 10/1990 | Mullis et al. | 435/6 |
| 5,174,986 | 12/1992 | Berns | 800/3 |
| 5,185,260 | 2/1993 | Crissman et al. | 435/244 |

FOREIGN PATENT DOCUMENTS

| | | |
|---|---|---|
| WO 92/20796 | 11/1992 | WIPO . |
| WO 96/32956 | 10/1996 | WIPO . |

OTHER PUBLICATIONS

Tseng et al., "Antisense oligonucleotide technology in the development of cancer therapeutics", Cancer Gene Therapy 1(1): 75–71, Mar. 1994.
Brown, "Gene therapy 'oversold' by researchers, journalists: NIH advisers cite nearly uniform failure". The Washington Post, pp. AI & AZZ, Dec. 8, 1995.
Coghlan, "Gene dream fades away", New Scientist 2005: 14–15, Nov. 25, 1995.
James, "Towards gene–inhibition therapy: a review of progress and prospects in the field of antiviral antisense nucleic acids and ribozymes", Antiviral Chem. Chemother. 2(4): 191–214, 1991.
Monia et al., "antitumor activity of a phosphororthioate antisense oligodeoxyribonucleotide targeted against C–raf kinase", Nature Med. 2(6): 668–675, Jun. 1996.
Gura, "Antisense has growing pains", Science 270: 575–577, Oct. 1995.
Stein et al., "Antisense oligonucleotides as therapeutic agents—is the bullet really magical", Science 261: 1004–1012, Aug. 1993.
Baldin, V., et al., "Cyclin D1 is a Nuclear Protein Required for Cell Cycle Progression in $G_1$," Genes & Devel. 7:812–821 (May 1993).
Bates, S., et al., "Absence of Cyclin D/cdk Complexes in Cells Lacking Functional Retinoblastoma Protein," Oncogene 9(6):1633–1640 (Jun. 1994).
Dowdy, S.F., et al., "Physical Interaction of the Retinoblastoma Protein with Human D Cyclins," Cell 73(3):499–511 (May 7, 1993).
El–Deiry, W.S., et al., "WAF1, a Potential Mediator of p53 Tumor Suppression," Cell 75(4):817–825 (Nov. 19, 1993).
Ewen, M.E., et al., "Functional Interactions of the Retinoblastoma Protein with Mammalian D–type Cyclins," Cell 73(3):487–497 (May 7, 1993).
Gu, Y., et al., "Inhibition of CDK2 Activity in vivo by an Associated 20K Regulatory Subunit," Nature 366:707–710 (Dec. 16, 1993).
Guan, K.–L., et al., "Growth Suppression by p18, a $p16^{INK4/MTS1}$–and $p14^{INK4B/MTS2}$–Related CDK6 Inhibitor, Correlates with Wild–type pRb Function," Genes & Devel. 8(24):2939–2952 (Dec. 15, 1994).
Hannon, G.J., and Beach, D., "$p15^{INK4B}$ is a Potential Effector of TGF–β–induced Cell Cycle Arrest," Nature 371:257–261 (Sep. 15, 1994).
Harper, J.W., et al., "The p21 Cdk–Interacting Protein Cip1 Is a Potent Inhibitor of G1 Cyclin–Dependent Kinases," Cell 75(4):805–816 (Nov. 19, 1993).
Kato, J.–Y., et al., "Direct Binding of Cyclin D to the Retinoblastoma Gene Product (pRb) and pRb Phosphorylation by the Cyclin D–Dependent Kinase CDK4," Genes & Devel. 7(3):331–342 (Mar. 1993).

(List continued on next page.)

Primary Examiner—Scott D. Priebe
Attorney, Agent, or Firm—Sterne, Kessler, Goldstein & Fox P.L.L.C.

[57] ABSTRACT

Members of the InK4 (Inhibitors of CDK4) family inhibit the activities of specific cyclin D-dependent kinases (CDK4 and/or CDK6), thereby arresting cell cycle progression in G1 phase and preventing chromosomal DNA replication. Disclosed herein are novel mammalian InK4 family members, having apparent molecular masses of 18,000 and 19,000 daltons, designated "InK4c-p18" and "InK4d-p19," respectively, or simply "p18" and "p19." In particular, the invention provides p19 genes and proteins isolated from murine or human cells and p18 genes and proteins from murine cells. When constitutively expressed in cells, p19 inhibits cyclin D-dependent kinase activity in vivo and induces G1 phase arrest. Materials and methods disclosed herein include (1) nucleic acids that encode p18 or p19; (2) methods for detecting nucleic acids encoding p18 or p19 proteins; (3) methods for producing p18 or p19 proteins using nucleic acids that encode p18 or p19, respectively; (4) purified pl8 or p19 proteins and peptide fragments, oligopeptides, or fusion proteins derived therefrom; (5) methods of inhibiting cells from replicating their chromosomal DNA using purified p18 or p19 proteins or derivatives thereof; (6) antibodies that specifically bind p18 or p19; (7) methods for detecting p18 and p19 proteins; (8) methods of stimulating cell growth by blocking p18 or p19 expression via antisense oligonucleotides; (9) methods of gene therapy using nucleic acids that encode p18 or p19; and (10) methods of making transgenic non-human animals that have alterations in the gene encoding p18 or p19, or in both genes.

5 Claims, 21 Drawing Sheets

OTHER PUBLICATIONS

Lukas, J., et al., "DNA Tumor Virus Oncoproteins and Retinoblastoma Gene Mutations Share the Ability to Relieve the Cell's Requirement for Cyclin D1 Function in G1," *J. Cell Biol.* 125(3):625–638 (May 1994).

Matsushime, H., et al., "Colony–Stimulating Factor 1 Regulates Novel Cyclins During the G1 Phase of the Cell Cycle," *Cell* 65(4):701–713 (May 17, 1991).

Matsushime, H., et al., "Identification and Properties of an Atypical Catalytic Subunit ($p34^{PSK-J3}$/cdk4) for Mammalian D Type G1 Cyclins," *Cell* 71(2):323–334 (Oct. 16, 1992).

Matsushime, H., et al., "D–Type Cyclin–Dependent Kinase Activity in Mammalian Cells," *Mol. Cell. Biol.* 14(3):2066–2076 (Mar. 1994).

Meyerson, M., and Harlow, E., "Identification of $G_1$ Kinase Activity for cdk6, a Novel Cyclin D Partner," *Mol. Cell. Biol.* 14(3):2077–2086 (Mar. 1994).

Nasmyth, K., and Hunt, T., "Dams and Sluices," *Nature* 366:634–635 (Dec. 16, 1993).

Peters, G., "Stifled by Inhibitions," *Nature* 371:204–205 (Sep. 15, 1994).

Polyak, K., et al., "$p27^{Kip1}$, a Cyclin–Cdk Inhibitor, Links Transforming Growth Factor–$\beta$ and Contact Inhibition to Cell Cycle Arrest," *Genes & Devel.* 8(1):9–22 (Jan. 1994).

Polyak, K., et al., "Cloning of $p27^{Kip1}$, a Cyclin–Dependent Kinase Inhibitor and a Potential Mediator of Extracellular Antimitogenic Signals," *Cell* 78(1):59–66 (Jul. 15, 1994).

Quelle, D.E., et al., "Overexpression of Mouse D–type Cyclins Accelerates $G_1$ Phase in Rodent Fibroblasts," *Genes & Devel.* 7(8):1559–1571 (Aug. 1993).

Serrano, M., et al., "A New Regulatory Motif in Cell–Cycle Control Causing Specific Inhibition of Cyclin D/CDK4," *Nature* 366:704–707 (Dec. 16, 1993).

Sherr, C.J., "Mammalian $G_1$ Cyclins," *Cell* 73:1059–1065 (Jun. 18, 1993).

Tam, S.W., et al., "Differential Expression and Regulation of Cyclin D1 Protein in Normal and Tumor Human Cells: Association with Cdk4 is Required for Cyclin D1 Function in G1 Progression," *Oncogene* 9(9):2663–2674 (Sep. 1994).

Toyoshima, H., and Hunter, T., "p27, a Novel Inhibitor of G1 Cyclin–Cdk Protein Kinase Activity, Is Related to p21," *Cell* 78(1):67–74 (Jul. 15, 1994).

Xiong, Y., et al., "Subunit Rearrangement of the Cyclin–Dependent Kinases is Associated with Cellular Transformation," *Genes & Devel.* 7(8):1572–1583 (Aug. 1993).

Xiong, Y., et al., "p21 Is a Universal Inhibitor of Cyclin Kinases," *Nature* 366:701–704 (Dec. 16, 1993).

Stein, C.A., et al., "Oligodeoxynucleotides as Inhibitors of Gene Expression: A Review," *Cancer Research* 48:2659–2668 (May 15, 1988).

```
HUMAN p16  M------EPSADWLATAAARGRVEEVRALL--EAVALPNAPNSYGRRPIQVMM    45
              | |    ||| | ||| ||   | |   | | |       |||
MOUSE p19  MLLEEVCVGDRLSGARARGDVQEVRRLLHRELV-HPDALNRFGKTALQVMM    50
           | |    | | | |||| |    |    |    | || ||||||
MOUSE p18  MA-EPW---GNELASAAARGD-LEQLTSLLQNNV-NVNAQNGFGRTALQVMK    46
              <            REPEAT 1              ><

HUMAN p16  MGSARVAELLLLHGAEPNCADPATLTRPVHDAAREGFLDTLVVLHRAGARL     96
           ||  ||  || || ||  | |  |  |||||||| ||||||       ||
MOUSE p19  FGSPAVALELLKQGASPNVQD-ASGTSPVHDAARTGFLDTLKVLVEHGADV    100
           | |   || || ||  |    |      |||||  ||||| |    | |||
MOUSE P18  LGNPEIARRLLLRGANPNLKD-GTGFAVIHDAARAGFLDTVQALLEFQADV    96
                  REPEAT 2        ><        REPEAT 3

HUMAN p16  DVRDAWGRLPVDLAEELGHRDVARYL------------RAAAGGTRGSNHARI    137
           | | ||  ||  ||  ||    |              | | |    ||
MOUSE p19  NALDSTGSLPIHLAIREGHSSVVSFL--APESDLHHRDASGLT-PLELARQ    148
           | |  | ||| ||| ||| || ||     || ||    ||| |  |||
MOUSE p18  NIEDNEGNLPLHLAAKEGHLPVVEFLMKGTACNVGHRNHKGDT-AFDLARF    146
                       ><         REPEAT 4              ><

HUMAN p16  DA----AEGPS---------DIPD     148
           |                    ||
MOUSE p19  RG----AQNLM---------DILQGHMMIPM     166
           |      ||           ||
MOUSE p18  YGRNEVISLMEANGVGGATSLQ     168
                REPEAT 5       >
```

FIG. 1A

```
16 Repeat 1:   EPSADWLATAAAR-GRVEEVRALL----EA-VALPN-APNS
16 Repeat 2:   YGRRPIQVMMGSA-RVAE-LLLLH---GAEPNCAD--P-A
16 Repeat 3:   TLTRPVHD---AAREGFLDT-LVVLHRAGARLDVRDDA 18 Repeat 1:   WGNELAS---AAAR-GDLEQLTSLLQN-NVNVNAQ----NG
18 Repeat 2:   FGRTALQVMKLGNPEI-AR-RLLLR-GANPNLKD----G
18 Repeat 3:   TGFAVIHD---AARAGFLDTVQALLEF-QADVNIED---N 19 Repeat 1:   VCVGDRLSGARAR-GDVQEVRRLLHR-EL-V-HPD-ALNR
19 Repeat 2:   FGKTALQVMMFGSPA-VA---LELLKQ-GASPNVQD-A
19 Repeat 3:   SGTSPVHD---AARTGFLDT-LKVLVEHGADVNALD----S
```

FIG. 1B

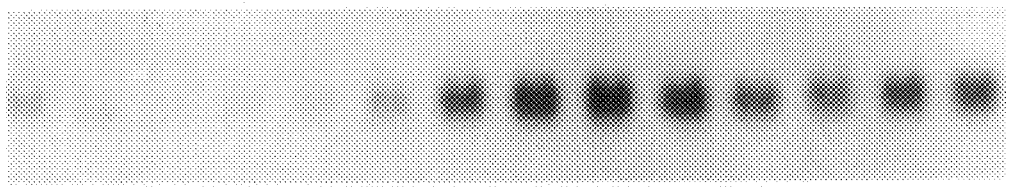
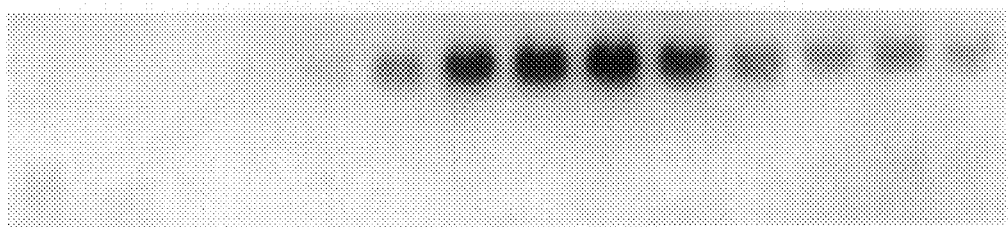
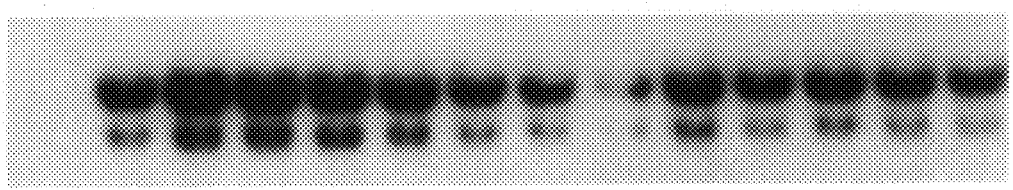
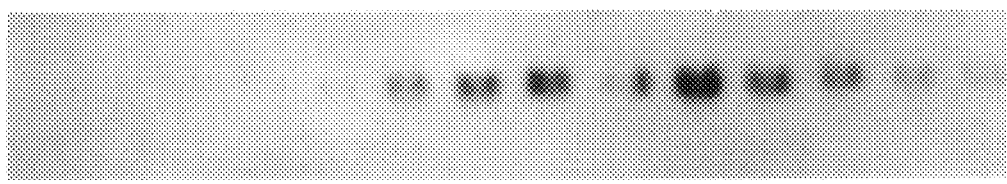
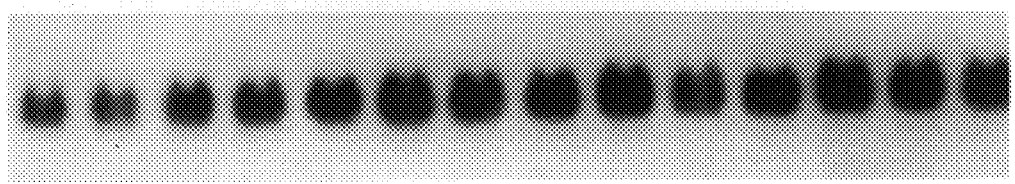
FIG. 7A

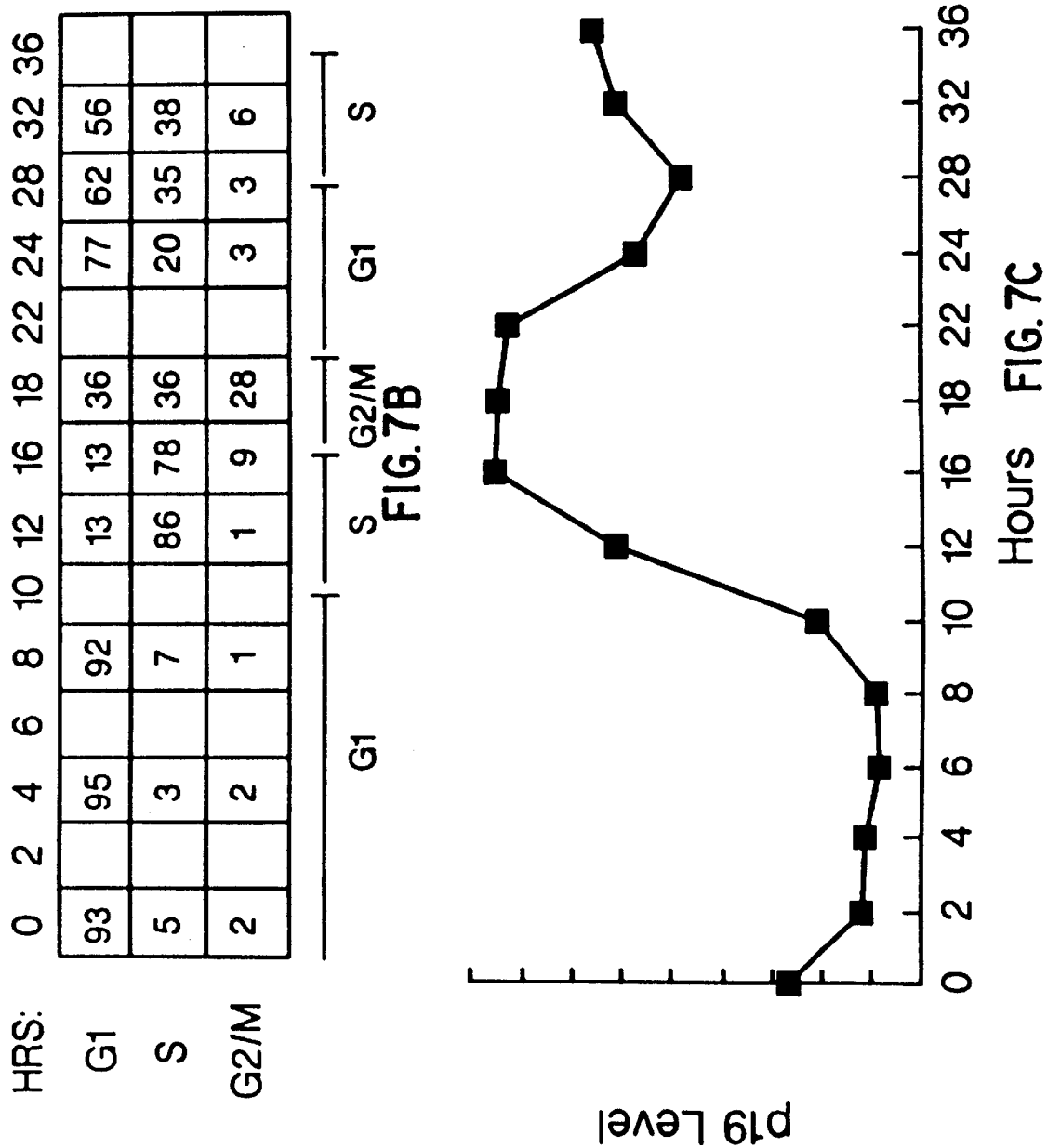

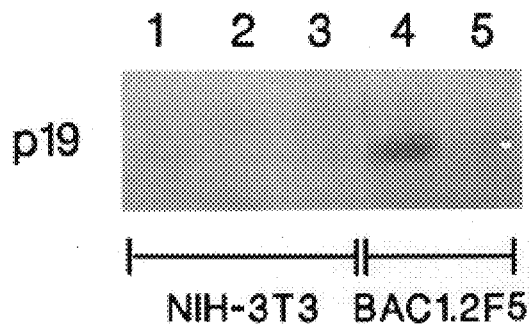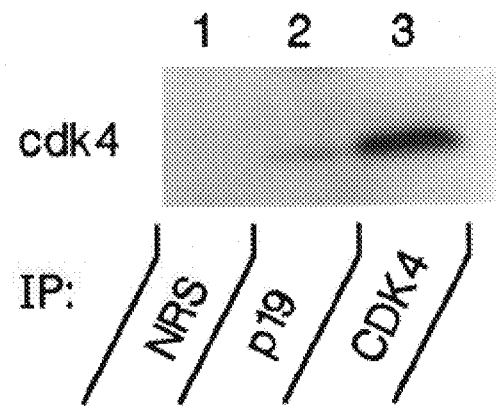
FIG.8A    FIG.8B
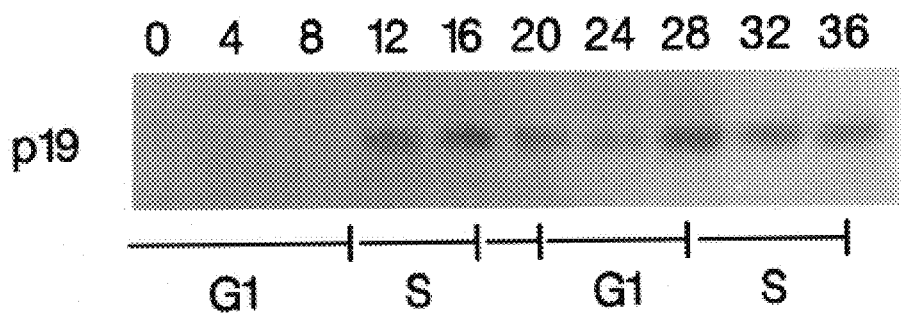
FIG.8C

```
1    TGACAGCGCCGGGCTGGGGCGGGGCGGGGGGCTTTGCAGGCCGCCAGTGTCGAC

55   ATGCTGCTGGAGGAGGTTCGCGCCGGCGACCGGCTGAGTGGGGCGGCGGCCCGG
     M   L   L   E   E   V   R   A   G   D   R   L   S   G   A   A   A   R      18
109  GGCGACGTGCAGGAGGTGCGCCGCCTTCTGCACCGCGAGCTGGTGCATCCCGAC
     G   D   V   Q   E   V   R   R   L   L   H   R   E   L   V   H   P   D      36
163  GCCCTCAACCGCTTCGGCAAGACGGCGCTGCAGGTCATGATGTTTGGCAGCACC
     A   L   N   R   F   G   K   T   A   L   Q   V   M   M   F   G   S   T      54
217  GCCATCGCCCTGGAGCTGCTGAAGCAAGGTGCCAGCCCCAATGTCCAGGACACC
     A   I   A   L   E   L   L   K   Q   G   A   S   P   N   V   Q   D   T      72
271  GCCATCGCCCTGGAGCTGCTGAAGCAAGGTGCCAGCCCCAATGTCCAGGACACC
     S   G   T   S   P   V   H   D   A   A   R   T   G   F   L   D   T   L      90
325  AAGGTCCTAGTGGAGCACGGGGCTGATGTCAACGTGCCTGATGGCACCGGGGCA
     K   V   L   V   E   H   G   A   D   V   N   V   P   D   G   T   G   A     108
379  CTTCCAATCCATCTGGCAGTTCAAGAGGGTCACACTGCTGTGGTCAGCTTTCTG
     L   P   I   H   L   A   V   Q   E   G   H   T   A   V   V   S   F   L     126
433  GCAGCTGAATCTGATCTCCATCGCAGGGACGCCAGGGGTCTCACACCCTTGGAG
     A   A   E   S   D   L   H   R   R   D   A   R   G   L   T   P   L   E     144
487  CTGGCACTGCAGAGAGGGGCTCAGGACCTCGTGGACATCCTGCAGGGCCACATG
     L   A   L   Q   R   G   A   Q   D   L   V   D   I   L   Q   G   H   M     162
541  GTGGCCCCGCTGTGA
     V   A   P   L   *                                                         166
```

FIG. 10A

```
Hu-P19  MLLEEVRAGDRLSGAAARGDVQEVRRLLHRELV-HPDALNRFGKTALQVMMFGSTAIALELL   61
        ||||||  |||||||  |||||||||||||||| |||||||||||||||||||| | |||||
Mu-P19  MLLEEVCVGDRLSGARARGDVQEVRRLLHRELV-HPDALNRFGKTALQVMMFGSPAVALELL   61
          |    |  |||||  |    |    |        ||  |||||| || |  |   ||
Hu-P18  M-AEPW--GNELASAAARGD-LEQLTSLLQNNV-NVNAQNGFGRTALQVMKLGNPEIARRL   57
        |       | |||||| |    |    |    |   ||  ||  |||   |      ||
Hu-P16  M----EPSADWLATAAARGRVEEVRALL--EAVALPNAPNSYGRRPIQVMMMGSARVAELLL   56
        |       ||  ||||||  ||  ||   ||  ||   |||  |||||||||||||||||
Hu-P15  M-PSGGGSDEGLASAAARGLVEKVRQLL--EAGADPNGVNRFGRRAIQVMMMGSARVAELLL   66

Hu-P19  KQGASPNVQD-TSGTSPVHDAARTGFLDTLKVLVEHGADVNVPDGTGALPIHLAVQEGHTAV  122
        ||||||||||  |||||||||||||||||||||||||||||  | || ||||| |  |  |
Mu-P19  KQGASPNVQD-ASGTSPVHDAARTGFLDTLKVLVEHGADVNALDSTGSLPIHLAIREGHSSV  122
           ||   |     |   ||||| ||||||| || |  ||||  | |  | ||  || |
Hu-P18  LRGANPDLKD-RTGFAVIHDAARAGFLDTLQTLLEFQADVNIEDNEGNLPLHLAAKEGHLRV  118
        | ||   |        |||||| ||||||  |   |    |  |   |  ||  ||  ||
Hu-P16  LHGAEPNCADPATLTRPVHDAAREGFLDTLVVLHRAGARLDVRDAWGRLPVDLAEELGHRDV  118
        |||||||||||||||||||||||||||||||||||||||||||||||||||||||| |||||
Hu-P15  LHGAEPNCADPATLTRPVHDAAREGFLDTLVVLHRAGARLDVRDAWGRLPVDLAEERGHRDV  128

Hu-P19  VSFL--AAESDLHRRDARGLTPLE-LALQRGAQDLVDILQGHMVAPL*                166
        ||||  | ||||||  | ||||||| || |||| | || |||| |  |
Mu-P19  VSFL--APESDLHHRDASGLTPLE-LARQRGAQNLMDILQGHMMIPM*                166
        | ||    |   ||  ||    ||    ||  |   |    |
Hu-P18  VEFLVKHTASNVGHRNHKGDTACD-LARLYGRNEVVSLMQANGAGGATNLQ*            168
              |      |   ||       ||    ||
Hu-P16  ARYL---------RAAAGGTRGSNHARIDAA-EGPSDIPD*                      148
        | ||         | | |
Hu-P15  AGYL---------RTATGD*                                            138
```

FIG. 10B

INK4C-P18 AND INK4D-P19, INHIBITORS OF CYCLIN-DEPENDENT KINASES CDK4 AND CDK6, AND USES THEREOF

FIELD OF THE INVENTION

This invention relates to the regulation of cellular growth, and methods of cancer detection and treatment, involving two related but distinct proteins, the first called "InK4c-p18," "p18INK4c," "p18$^{INK4c}$," or simply "p18," and the second called "InK4d-p19," "p19INK4d," "p19$^{INK4d}$," or simply "p19," that regulate the eukaryotic cell cycle and, when overexpressed, inhibit cells from proceeding past the G1 phase of the cell cycle, i.e., prevent cells from initiating the replication of chromosomal DNA molecules. In particular, materials and methods disclosed herein include (1) nucleic acids that encode p18 or p19 polypeptide sequences, isolated from mice, humans and other mammals; (2) methods for detecting nucleic acids encoding p18 or p19 proteins, or alterations in such nucleic acids; (3) methods for producing proteins having p18 or p19 polypeptide sequences using nucleic acids that encode p18 or p19, respectively; (4) purified p18 or p19 proteins and peptide fragments, oligopeptides, or fusion proteins derived therefrom; (5) methods of inhibiting cells from replicating their chromosomal DNA using purified p18 or p19 proteins or derivatives thereof; (6) antibodies that specifically bind p18 or p19; (7) methods for detecting p18 and p19 proteins; (8) methods of stimulating cell growth by blocking p18 or p19 expression using antisense oligonucleotides that contain nucleotide sequences complementary to nucleic acids that encode p18 or p19 polypeptide sequences; (9) methods of gene therapy using nucleic acids that encode p18 or p19; and (10) methods of making transgenic non-human animals that have a genetically engineered alteration in the gene encoding p18 or p19, or in both genes.

Statement as to Rights to Inventions Made Under Federally-Sponsored Research and Development This invention was made with U.S. Government support under grants CA-47064 and CA-20150, awarded by the National Institutes of Health, and Cancer Center CORE grant CA-21765. The U.S. Government has certain rights in this invention. Support for this invention was also provided by the Howard Hughes Medical Institute and the American Lebanese Syrian Associated Charities of St. Jude Children's Research Hospital.

BACKGROUND OF THE INVENTION

Neoplasia, the pathological process by which tumors develop, necessarily involves unregulated, or at best misregulated, cellular growth and division. The molecular pathways that regulate cellular growth must inevitably intersect with those that regulate the cell cycle. The cell cycle consists of a cell division phase and the events that occur during the period between successive cell divisions, known as interphase. Interphase is composed of successive G1, S, and G2 phases, and normally comprises 90% or more of the total cell cycle time. Most cell components are made continuously throughout interphase; it is therefore difficult to define distinct stages in the progression of the growing cell through interphase. One exception is DNA synthesis, since the DNA in the cell nucleus is replicated only during a limited portion of interphase. This period is denoted as the S phase (S=synthesis) of the cell cycle. The other distinct stage of the cell cycle is the cell division phase, which includes both nuclear division (mitosis) and the cytoplasmic division (cytokinesis) that follows. The entire cell division phase is denoted as the M phase (M=mitotic). This leaves the period between the M phase and the start of DNA synthesis, which is called the G1 phase (G=gap), and the period between the completion of DNA synthesis and the next M phase, which is called the G2 phase (Alberts, B. et at., *Molecular Biology of the Cell*, Garland Publishing, Inc., New York & London (1983), pages 611–612.).

Progression through different transitions in the eukaryotic cell cycle is positively regulated by a family of master enzymes, the cyclin-dependent kinases (reviewed by Sherr, C. J., *Cell* 73:1059–1065 (1993)). These holoenzymes are composed of two proteins, a regulatory subunit (the cyclin), and an associated catalytic subunit (the actual cyclin-dependent kinase or CDK), the levels of which vary with different phases of the cell cycle (Peters, G., *Nature* 371:204–205 (1994)). Both cyclins and CDKs represent molecular families that encompass a variety of genetically related but functionally distinct proteins. Generally, different types of cyclins are designated by letters (i.e., cyclin A, cyclin B, cyclin D, cyclin E, etc.); CDKs are distinguished by numbers (CDK1, CDK2, CDK3, CDK4, CDK5, etc.; CDK1 is a.k.a. CDC2).

CDK-cyclin D complexes regulate the decision of cells to replicate their chromosomal DNA (Sherr, *Cell* 73:1059–1065 (1993)). As cells enter the cycle from quiescence, the accumulation of CDK-cyclin D holoenzymes occurs in response to mitogenic stimulation, with their kinase activities being first detected in mid-G1 phase and increasing as cells approach the G1/S boundary (Matsushime et al., *Mol. Cell. Biol.* 14:2066–2076 (1994); Meyerson and Harlow, *Mol. Cell. Biol.* 14:2077–2086 (1994)). The cyclin D regulatory subunits are highly labile, and premature withdrawal of growth factors in G1 phase results in a rapid decay of CDK-cyclin D activity that correlates with the failure to enter S phase. In contrast, removal of growth factors late in G1 phase, although resulting in a similar collapse of CDK-cyclin D activity, has no effect on further progression through the cell cycle (Matsushime et al., *Cell* 65:701–713 (1991)). Microinjection of antibodies to cyclin D1 into fibroblasts during G1 prevents entry into the S phase, but injections performed at or after the G1/S transition are without effect (Baldin et al., *Genes & Devel.* 7:812–821 (1993); Quelle et al., *Genes & Devel.* 7:1559–1571 (1993)). Therefore, CDK-cyclin D complexes execute their critical functions at a late G1 checkpoint, after which cells become independent of mitogens for completion of the cycle.

In mammals, cells enter the cell cycle and progress through G1 phase in response to extracellular growth signals which trigger the transcriptional induction of D-type cyclins. The accumulation of D cyclins leads to their association with two distinct catalytic partners, CDK4 and CDK6, to form kinase holoenzymes. Several observations argue for a significant role of the cyclin D-dependent kinases in phosphorylating the retinoblastoma protein, pRb, leading to the release of pRB-associated transcription factors that are necessary to facilitate progression through the G1→S transition. First, CDK-cyclin D complexes have a distinct substrate preference for pRb but do not phosphorylate the canonical CDK substrate, histone Hi (Matsushime et al., *Cell* 71:323–334 (1992); Matsushime et al., *Mol. Cell. Biol.* 14:2066–2076 (1994); Meyerson and Harlow, *Mol. Cell. Biol.* 14:2077–2086 (1994)). Their substrate specificity may be mediated in part by the ability of D-type cyclins to bind to pRb directly, an interaction which is facilitated by a Leu-X-Cys-X-Glu pentapeptide that the D cyclins share with DNA oncoproteins that also bind pRb (Dowdy et al.,

*Cell* 73:499–511 (1993); Ewen et al., *Cell* 73:487–497 (1993); Kato et al., *Genes & Devel.* 7:331–342 (1993)). Second, cells in which pRb function has been disrupted by mutation, deletion, or after transformation by DNA tumor viruses are no longer inhibited from entering S phase by microinjection of antibodies to D cyclin, indicating that they have lost their dependency on the cyclin D-regulated G1 checkpoint (Lukas et al., *J. Cell. Biol.* 125:625–638 (1994); Tam et al., *Oncogene* 9:2663–2674 (1994)). However, introduction of pRb into such cells restores their requirement for cyclin D function (Lukas et al., *J. Cell. Biol.* 125:625–638 (1994)). Third, pRb-negative cells synthesize elevated levels of a 16 kDa polypeptide inhibitor of CDK4, "p16$^{Ink4a}$" (a.k.a. "InK4a-p16" or simply "p16"), which is a member of a recently discovered class of cell cycle regulatory proteins (Nasmyth and Hunt, *Nature* 366:634–635 (1993); Peters, G., *Nature* 371:204–205 (1994)). InK4a-p16 is found in complexes with CDK4 at the expense of D-type cyclins during G1 phase (Bates et al., *Oncogene* 9:1633–1640 (1994); Serrano et al., *Nature* 366:704–707 (1993); Xiong et al., *Genes & Devel.* 7:1572–1583 (1993)). The fact that such cells cycle in the face of apparent CDK4 inhibition again implies that D-type cyclins are dispensable in the Rb-negative setting.

A protein related to p16 is a 15 kDa protein that inhibits both CDK4 and CDK6, "p15$^{InK4b}$" (a.k.a. "InK4b-p15" or simply "p15"), which is induced in human epithelial cells treated by transforming growth factor-β (TGF-β) (Hannon and Beach, *Nature* 371:257–261 (1994)). Thus, in contradistinction to the positive regulation of D-type cyclin synthesis by growth factors, extracellular inhibitors of G1 progression can negatively regulate the activity of D-type cyclin-dependent kinases by inducing InK4 proteins. Structurally, known InK4 proteins are composed of repeated 32 amino acid ankyrin motifs. Unlike other universal CDK inhibitors, such as p21$^{Cip1/Waf1}$ (El-Deiry et al., *Cell* 75:817–825 (1993); Gu et al., *Nature* 366:707–710 (1993); Harper et al., *Cell* 75:805–816 (1993); Xiong et al., *Nature* 366:701–704 (1993)) and p27$^{Kip1}$ (Polyak et al., *Genes & Devel.* 8:9–22 (1994); Polyak et al., *Cell* 78:59–66 (1994); Toyoshima and Hunter, *Cell* 78:67–74 (1994)), the InK4 proteins selectively inhibit the activities of CDK4 and CDK6, but do not inhibit the activities of other CDKs (Guan et al., *Genes & Devel.* 8:2939–2952 (1994); Hannon and Beach, *Nature* 371:257–261 (1994); Serrano et al., *Nature* 366:704–707 (1993)).

Related Art

Mullis et al., U.S. Pat. No. 4,965,188 (Oct. 23, 1990), describe methods for amplifying nucleic acid sequences using the polymerase chain reaction (PCR).

Beach, published PCT patent application WO 92/20796 (Nov. 26, 1992), describes genes encoding D cyclins and uses thereof.

Berns, U.S. Pat. No. 5,174,986 (Dec. 29, 1992), describes methods for determining the oncogenic potential of chemical compounds using a transgenic mouse predisposed to develop T-cell lymphomas.

Crissman et al., U.S. Pat. No. 5,185,260 (Feb. 9, 1993), describe methods for distinguishing and selectively killing transformed (neoplastic) cells using synthetic G1 kinase inhibitors.

Guan et al. (*Genes & Devel.* 8:2939–2952 (1994)) describe the isolation of a gene encoding human p18, the apparent homolog of mouse p18 described herein.

SUMMARY OF THE INVENTION

The present invention relates to the discovery in mammalian cells of a novel cell cycle regulatory protein, having an apparent molecular mass of 19 kDa, here designated "InK4d-p19," "p19$^{ink4/6}$," or more simply "p19". In particular, the invention relates to p19 isolated from cells derived from a mouse or a human.

The present invention also relates to the discovery in mouse cells of a novel cell cycle regulatory protein, having an apparent molecular mass of 18 kDa, here designated "InK4c-p18," "p18$^{ink4/6}$," or more simply "p18." Mouse p18 is the apparent homolog of human p18, the gene for which has been isolated and mapped to human chromosome 1 (Guan et al., *Genes & Devel.* 8:2939–2952 (1994)).

The proteins of the invention belong to the InK4 gene family ("InK4" signifies Inhibitors of CDK4), known to include at least two other low molecular weight polypeptides, InK4a-p16 and InK4b-p15 (Serrano, M. et al., *Nature* 366:704–707 (1993); Hannon G. J. and Beach, D., *Nature* 371:257–261 (1994)). Members of the InK4 family are typically composed of repeated ankyrin motifs, each of about 32 amino acids in length. All known members of the InK4 family act to specifically inhibit enzymatic activities of D-type cyclin-dependent kinases such as CDK4 and CDK6. Like many CDK inhibitors (CKIs) (Nasmyth and Hunt, *Nature* 366:634–635 (1993)), InK4 family members negatively regulate progression through the mammalian cell cycle, in part in response to anti-proliferative extracellular signals. The InK4 proteins, by inhibiting the activities of a specific class of the D-type cyclin-dependent kinases (i.e., CDK4 and/or CDK6), arrest cell cycle progression in G1 phase and thus prevent cells from replicating their chromosomal DNA. InK4d-p19 is periodically expressed during the cell cycle, being maximally induced as cells enter S phase. Significantly, when constitutively expressed in mouse NIH-3T3 fibroblasts, p19 inhibits cyclin D-dependent kinase activity in vivo and induces G1 phase arrest.

One aspect of the invention is directed to methods of using the proteins of the invention to inhibit the growth of cancer cells and/or to prevent cancer cells from replicating their chromosomal DNA. Both InK4-p16 and InK4-p15 appear to act as tumor suppressors (Noburi, T. et al., *Nature* 368:753–756 (1994); Kamb, A. et al., *Science* 264:436–440 (1994)). The genes encoding p16 and p15 map in a tandem array to the short arm of human chromosome 9 within a region that is frequently deleted in cancer cells, and the resulting loss of their anti-proliferative functions can contribute to tumorigenesis (Noburi et al., *Nature* 368:753–756 (1994)). As members of the InK4 gene family, p18 and p19 have similar properties, namely, (1) they play a role in preventing the G1→S phase transition in normal mammalian cells; (2) synthesis of p18 or p19 is induced by particular anti-mitogenic compounds that arrest cells in G1 phase; (3) and deletion of the gene encoding p18 or p19, in subverting the possibility of such control, contributes to oncogenesis in some cancers.

In another aspect, the invention provides nucleic acid sequences encoding p19 polypeptides from mice, humans and other mammals, and p18 polypeptides from non-human mammals. The nucleic acid sequences of the invention may be expressed in the form of isolated nucleic acids, such as cDNA clones, genomic DNA clones, mRNA transcribed from either cDNA or genomic DNA clones, synthetic oligonucleotides, and/or synthetic amplification products resulting from PCR, and may be single-stranded or double-stranded.

In a related aspect, the invention provides methods for detecting nucleic acids encoding p18 or p19 using the nucleic acid sequences of the invention described above.

The detection of deletions of, or other mutations in, the genes encoding p18 or p19 is predicative of a predisposition to, or diagnostic of, certain types of cancer.

In another related aspect, the DNA molecules of the invention described above may be cloned into expression vectors and placed in an appropriate host in order to produce p18 or p19 proteins or fusion proteins containing p18 or p19 polypeptide sequences. When placed in an animal that has cancer, this aspect of the invention relates to gene therapy for certain types of cancers.

In another related aspect, the invention provides methods of stimulating cell growth by blocking p18 or p19 expression using antisense oligonucleotides that contain nucleotide sequences complementary to nucleic acids that encode p18 or p19 polypeptide sequences. These methods are used to stimulate cells, particularly hematopoietic stem cells, to replicate their chromosomal DNAs and to enter a proliferative state.

In another aspect, the invention provides antibody compositions that bind specifically to p18 or p19 proteins. The antibody compositions of the invention may be polyclonal, monoclonal, or monospecific. The antibody compositions of the invention bind specifically to p18 or p19, or to fusion proteins or oligopeptides containing p18 or p19 polypeptide sequences.

In a related aspect, the invention provides methods for detecting p18 or p19 proteins using the antibody compositions described above. The detection of reduced amounts of, or altered forms of, p18 or p19 proteins is predicative of a predisposition to, or diagnostic of, certain types of cancer.

In another aspect, the invention provides transgenic non-human animals that have at least one mutation in the gene(s) encoding p18, p19, or both p18 and p19. Because of the transgenic mutation(s) introduced into the genome of the non-human animal, the animal has reduced levels of p18 and/or p19 activity compared to wild-type animals, and consequentially develops certain types of cancers in a reproducible and thus predictable manner.

In a related aspect, compositions are evaluated for their potential to stimulate or inhibit certain types of cancers using the transgenic non-human animals of the invention.

BRIEF DESCRIPTION OF THE FIGURES

FIG. 1 shows the amino acid sequences of mouse InK4c-p18 (SEQ ID NO:1) and mouse InK4d-p19 (SEQ ID NO:2) aligned with human InK4a-p16 (SEQ ID NO:16). In Panel A, the predicted amino acid sequences of mouse p18 (SEQ ID NO:18) and human InK4a-p16 are aligned (using the Intelligenetics FAST DB computer program) with that of mouse p19 (SEQ ID NO:17). The limits of the five ankyrin repeats are indicated by the arrows below the aligned sequences. In Panel B, Ankyrin repeats 1–3 of human p16 and of mouse p18 and p19 are shown as aligned with each other by visual inspection. Sequences shared between at least two of three repeats within the same protein (e.g., between repeats 1 and 2 of p16) are indicated by bold type face, whereas sequences shared by cognate repeats in at least one of the two homologous proteins (e.g., by repeats 1 in p19 and p18) are demarcated by double underlines. Nucleotide sequences of the cDNAs for mouse InK4d-p19 (SEQ ID NO:6) and mouse InK4c-p18 (SEQ ID NO:4) will be accessible from GENBANK under accession numbers U19597 and U19596, respectively, after May 1, 1995.

FIG. 7 shows the expression of p19 and different cyclins during the macrophage cell cycle. BAC1.2F5 macrophages arrested in early G1 phase by CSF-1 starvation for 18 hrs were restimulated with CSF-1 to enter the cell cycle synchronously. Total RNA extracted from cells at the indicated times in hrs (Panel A) were subjected to Northern blotting analysis using the probes indicated at the left margin. The different cell cycle phases were determined by flow cytometric analysis of cellular DNA content (Panel B). The cells lost synchrony as they progressed into the second cell cycle, and their second G1 phase was shorter than the first (Matsushime et al., Cell 65:701–713 (1991)). The concentration of p19 mRNA, as quantitated with a phosphoimager, is shown in Panel C. Exposure times for the Northern blots were 6 days for p19, 8 days for p18, 2 days for cyclins D1 and A, and 1 day for G6PD mRNA.

FIGS. 10A and 10B show the cDNA nucleotide (SEQ ID NO:19) and predicted amino acid (SEQ ID NO:20) sequences of human InK4d-p 19 FIG. 10A and the alignment of the polypeptide sequences of InK4 proteins: human p19 (Hu-P19) (SEQ ID NO:21), mouse p19 (Mu-P19) (SEQ ID NO:22), human p18 (SEQ ID NO:23) (Hu-P18), human p16 (SEQ ID NO:24) (Hu-P16) and human p15 (SEQ ID NO:25) (Hu-P15) (FIG. 10B).

DETAILED DESCRIPTION OF THE DISCLOSURE

Terms and Symbols

Figure 2A:
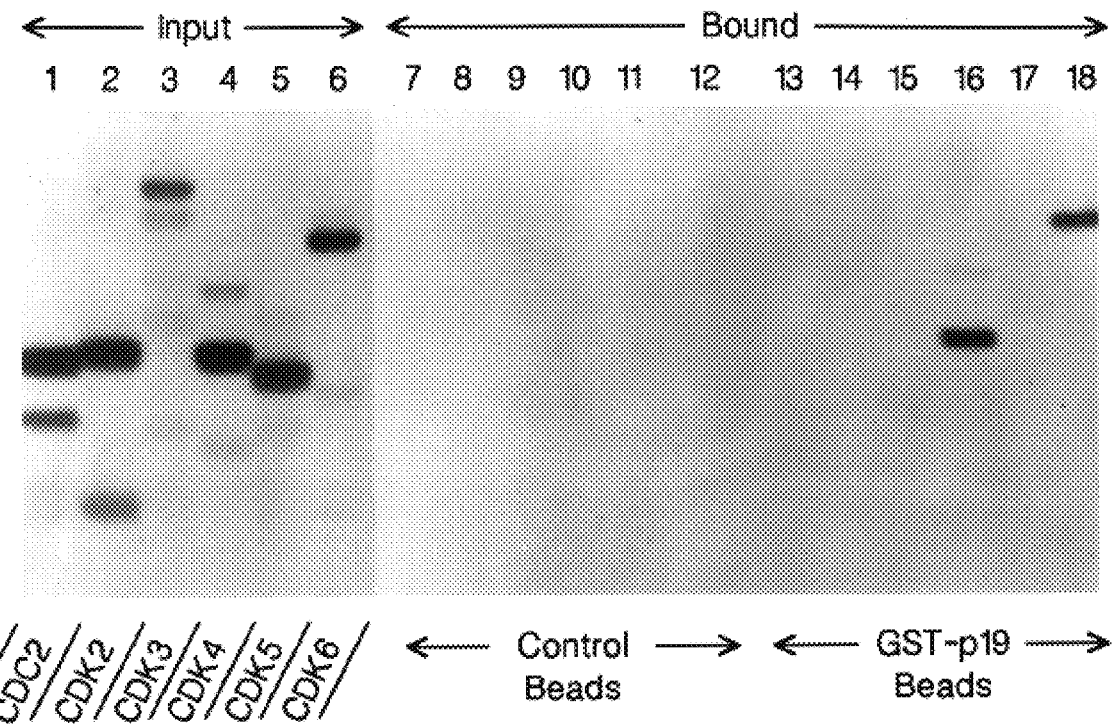
FIG. 2 displays results demonstrating the binding of mouse p19 to the cdk4 and cdk6 gene products. Panel A is an autoradiograph of aliquots of the $^{35}$S-methionine-labeled products, derived from the in vitro transcription and translation of plasmids containing CDNA coding sequences of the cdc or cdk gene indicated in the legend below lanes 1–6, separated by electrophoresis on denaturing polyacrylamide gels. Equal aliquots of the "input" samples shown in lanes 1–6 were incubated with control beads (lanes 7–12) (i.e., GST-Sepharose; GST=glutathione S-transferase) or with beads containing a GST-p19 fusion protein (lanes 13–18), after which the beads were washed, and adsorbed radiolabeled products were separated on gels and autoradiographed. In Panel B, the experiments were performed as in panel A, except that radiolabeled cyclins D2 and D3 were substituted for cdk gene products; the cdk4 gene product was used as a positive control. All autoradiographic exposure times were 15 hrs.

Throughout the disclosure, abbreviations for amino acid and nucleotide residues present in, respectively, polypeptide and nucleic acid sequences, are as described in 37 C.F.R. § 1.822, revised as of Jul. 1, 1994.

The following additional abbreviations and definitions are used herein unless otherwise indicated.

ABBREVIATIONS

| | | |
|---|---|---|
| 3-AT | = | 3-amino-1,2,4-trizole |
| ATP | = | adenosine triphosphate |
| CDK | = | cyclin-dependent kinase (protein); |
| | | *cdk* = gene |
| cDNA | = | complementary deoxyribonucleic acid |
| cpm | = | counts per minute |
| DNA | = | deoxyribonucleic acid |
| DMEM | = | Dulbecco's modified Eagle's medium |
| DTT | = | dithiothreitol |
| EDTA | = | ethylenediamine tetraacetic acid |
| EGTA | = | ethylene glycol-bis(β-aminoethyl ether) N,N,N',N'-tetraacetic acid |
| ES | = | embryonic stem |
| FISH | = | fluorescent *in situ* hybridization |
| G6PD | = | glucose 6-phosphate dehydrogenase |
| GST | = | glutathione S-transferase |
| HSV | = | herpes simplex virus |
| InK | = | inhibitor of CDK (protein); |
| | | *Ink* = gene |
| IP | = | immunoprecipitating |
| IPTG | = | isopropyl-β-D-thiogalactoside |
| kb | = | kilobase(s) |
| kDa | = | kilodalton(s) |
| LTR | = | long terminal repeat |
| mRNA | = | messenger RNA |
| MSV | = | mouse sarcoma virus |
| NRS | = | nonimmune rabbit serum |
| PBS | = | phosphate-buffered saline |
| PCR | = | polymerase chain reaction |
| pRB | = | retinoblastoma protein |
| RT | = | reverse transcriptase |
| SDS | = | sodium dodecyl sulfate |
| Sf9 | = | *Spodoptera frugiperda* |
| Tg | = | transgenic |
| TK | = | thymidine kinase |
| YPD | = | Yeast extract plus peptone and dextrose |

Glossary

Amino acid sequence: The sequence of a polypeptide given in the order of from amino terminal (N-terminal), to carboxyl terminal (C-terminal). Synonymous with "polypeptide sequence," "peptide sequence," "protein sequence," or "primary protein sequence."

Animal: (1) Excludes human beings, individually and collectively, in all stages of development, including embryonic and fetal stages, unless otherwise indicated; and (2) includes all other vertebrate animals, including an individual animal in any stage of development, including embryonic and fetal stages. "Non-human animal" has the same meaning as "animal."

Animal model: A non-human animal that faithfully mimics a human disease and in which potential therapeutic compositions or potentially harmful compositions may be evaluated for their effect on the disease.

Antibody: A protein molecule synthesized by a B-cell upon exposure to antigen capable of combining specifically with that antigen. Synonymous with immunoglobulin (Ig).

Antibody, polyclonal: A composition that comprises an assortment of different antibodies that all recognize a particular antigen.

Antibody, monoclonal: A unique, isolated antibody molecule produced by a hybridoma.

Antibody, monospecific: A polyclonal antibody produced in immunological response to a single or few epitopes found in (1) a short, isolated, synthetic antigen or (2) a short, isolated, carrier-bound hapten.

Antigen: A molecule or composition of matter which (1) induces an immune response in an animal, and (2) interacts specifically with antigen-recognizing components of an immune animal's immune system.

Carrier: A molecule required in combination with a hapten in order for an immune response to the hapten to occur. That is, a molecule which puts a hapten in a molecular context in which the hapten has enhanced immunogenicity.

Detectable label: A chemical moiety that is coupled to a biomolecule to enable detection of the biomolecule and which may be selected from the group consisting of a radiolabel, an enzyme such as horseradish peroxidase or alkaline phosphatase, streptavidin, biotin, an epitope recognized by an antibody, and equivalents thereof.

Detectably labelled: A state of a biomolecule in which the biomolecule has covalently attached to it a detectable label.

Disease: (1) Excludes pregnancy per se but not autoimmune and other diseases associated with pregnancy; (2) includes any abnormal condition of an organism or part, especially as a consequence of infection, inherent weakness, environmental stress, that impairs normal physiological functioning; and (3) includes cancers and tumors.

DNA sequence: The sequence of contiguous nucleotide bases of a strand of DNA as read from 5' to 3'. Synonymous with "DNA molecule."

Enzyme: Protein that is a catalyst for a specific chemical reaction, often one involving one or more biomolecules as substrates and/or products. Unlike non-biologically derived catalysts, enzymes may recognize a substrate with stereospecificity, i.e., some enzymes are capable of recognizing, and thus catalyzing the chemical reaction of, only one of a pair of L- and D-enantiomers.

Epitope: A part of an antigen that interacts specifically with antigen-recognizing components of an animal's immune system. In a polypeptidic antigen, epitopes may correspond to short sequences of contiguous amino acids; the remainder of the antigen is called the carrier. Synonymous with antigenic determinant.

Expression vector: An artificial DNA sequence or a naturally-occurring DNA sequence that has been artificially modified, into which foreign or abnormal genes can be inserted for expression thereof in host organisms appropriate for the vector.

Foreign or abnormal: Not endogenous to a healthy, wild-type organism. "Foreign or abnormal genes" designates nucleic acid sequences that are not endogenous to an organism's genome, or originally endogenous nucleic acid sequences that have been rearranged, mutated, or otherwise genetically engineered so as to possess properties (i.e., genomic location, regulation of expression, copy number, etc.) not possessed by the endogenous nucleic acid sequences from which they were derived.

Gene: A DNA sequence that consists of a structural gene, e.g., a reading frame that encodes a polypeptide sequence, according to the standard genetic code; and expression elements, e.g., promoters, terminators, enhancers, etc., required for transcription of the structural gene.

Genetically engineered: Subject to human manipulation intended to introduce genetic change.

Hapten: A small molecule which (1) cannot, by itself, induce an immune response in an animal, (2) can, in combination to a carrier to which it is bound, induce an immune response in an animal, and (3) interacts specifically with the antigen-recognizing components of an immune animal's immune system.

Host animal: An animal that harbors foreign and/or abnormal genes introduced as a result of (1) invasion of cells of the animal by a naturally occurring or genetically engineered intracellular parasite; or (2) introduction into cells of foreign or abnormal genes by human manipulation.

Immune animal. An animal which has been presented with an immunizing amount of antigen and has generated a humoral and/or cell-mediated immune response thereto.

Mammal: (1) Excludes human beings, individually and collectively, in all stages of development, including embryonic and fetal stages, unless otherwise indicated; and (2) includes all other animals that are members of the vertebrae class Mammalia, including an individual animal in any stage of development, including embryonic and fetal stages, wherein members of the class are distinguished by self-regulating body temperature, hair, and, in the females, milk-producing mammae.

Microorganism: A single-celled organism (e.g., a bacterium) or an intracellular parasite (e.g., a rickettsia or a virus); includes both "live" and "attenuated" microorganisms.

Polypeptide: A polymer of amino acid residues.

Protein: A biomolecule comprising one or more polypeptides arranged into a functional, three-dimensional form.

Restriction endonuclease: An endonuclease that cleaves DNA at each occurrence therein of a specific recognition sequence. Synonymous with "restriction enzyme."

Transgene: A gene that does not occur naturally in an animal, i.e., a foreign or abnormal gene, introduced into an animal by nonnatural means, i.e., by human manipulation.

Transgenic animal: An animal into which has been introduced, by nonnatural means, i.e., by human manipulation, one or more transgenes.

DETAILED DESCRIPTION OF THE PREFERRED EMBODIMENTS

In its broadest form, the invention comprises two novel mammalian protein members of the InK4 family, known as "InK4c-p18" (a.k.a. "p18") and "InK4d-p19" (a.k.a. "p19"), that regulate the cell cycle by inhibiting cyclin-dependent kinases such as CDK4; nucleic acid molecules having sequences encoding polypeptide sequences of p18 and p19; antibodies specific for p18 or p19 polypeptide sequences; transgenic non-human animals with alterations in the gene (s) encoding p18, p19, or both p18 and p19; methods of making p18 and p19 nucleic acids and polypeptides; methods of making p18- or p19-specific antibodies; methods of making transgenic non-human animals with alterations in the gene(s) encoding p18, p19, or both p18 and p19; and methods of using the nucleic acids, proteins, antibodies and transgenic animals of the invention to detect p18 and p19 nucleic acids or proteins in a sample, to diagnose cancers or predispositions thereto, to evaluate compositions for their therapeutic or oncogenic potential, and to prepare therapeutic compositions for the treatment of tumors and cancers.

Nucleic Acids and Related Embodiments

In one embodiment, the invention comprises nucleic acids having sequences encoding mouse p19, human p19 and p19 polypeptides from other mammals. For example, the invention provides cDNA molecules encoding mouse p19 (SEQ ID NO:6) and human p19 (SEQ ID NO:7). The p19 cDNAs of the invention are in turn used to isolate additional nucleic acids that encode p19 polypeptide sequences, such as mouse and human genomic DNA clones. Moreover, because the homology between the nucleotide sequences of mouse and human p19 genes is quite high, the mouse and human nucleic acids may be used to design probes or degenerate primers for PCR in order to isolate cDNA and genomic clones of p19 genes from other mammals.

In a parallel embodiment, the invention comprises nucleic acid sequences encoding mouse p18 and p18 polypeptides from other non-human mammals. For example, the invention provides cDNA molecules encoding mouse p18 (SEQ ID NO:4). The p18 nucleic acids of the invention are in turn used to isolate additional nucleic acids that encode p18 polypeptide sequences, such as mouse genomic DNA clones, and cDNA and genomic clones from other mammals. A nucleic acid encoding human p18 has recently been described by Guan et al. (*Genes & Develop.* 8:2939–2952 (1994)).

One skilled in the art can readily adapt the nucleic acid sequences of the invention to any system which is capable of producing nucleic acids to produce the nucleic acids of the invention. The nucleic acids of the invention, which may optionally comprise a detectable label, may be prepared as cDNA clones, genomic clones, RNA transcribed from either cDNA or genomic clones, synthetic oligonucleotides, and/or synthetic amplification products resulting, e.g., from PCR. The nucleic acids of the invention may be prepared in either single- or double-stranded form.

Methods of preparing cDNA clones are known in the art (see, for example, Chapter 8 in Sambrook et al., *Molecular Cloning: A Laboratory Manual*, Vol. 2, 2d. Ed., Cold Spring Harbor Laboratory Press, Cold Spring Harbor, N.Y. (1989), pages 8.1–8.86). Methods of analyzing genomic DNA sequences and preparing genomic clones are known in the art (see, for example, Chapter 9 in Sambrook et al., *Molecular Cloning: A Laboratory Manual*, Vol. 2, 2d. Ed., Cold Spring Harbor Laboratory Press, Cold Spring Harbor, N.Y. (1989), pages 9.1–9.62; and Chapter 2 in *Current Protocols in Molecular Biology*, Vol. 1, Ausubel et al., eds., John Wiley & Sons, Inc., Boston, Mass. (1994), pages 2.1.1–2.14.8). Genomic DNA sequences, i.e., chromosomally-derived nucleic acids, are isolated (see Example 9) from mice and other non-human animals and used for the production of transgenic non-human animals. RNA containing p18 or p19 sequences may be prepared from cells expressing p18 or p19, respectively, according to methods known in the art (see, e.g., Chapter 4 in *Current Protocols in Molecular Biology*, Vol. 1, Ausubel et al., eds., John Wiley & Sons, Inc., Boston, Mass. (1994), pages 4.1.1–4.10.11), or may be generated by in vitro transcription using the DNA molecules of the invention (see, e.g., Chapter 10 in Sambrook et al., *Molecular Cloning: A Laboratory Manual*, Vol. 2, 2d. Ed., Cold Spring Harbor Laboratory Press, Cold Spring Harbor, N.Y. (1989), pages 10.1–10.70). Synthetic oligonucleotides having p18 or p19 nucleotide sequences can be prepared using the nucleic acid sequences of the invention by known methods (see, e.g., Chapter 11 in Sambrook et al., *Molecular Cloning: A Laboratory Manual*, Vol. 2, 2d. Ed., Cold Spring Harbor Laboratory Press, Cold Spring Harbor, N.Y. (1989), pages 11.1–11.61). When used as primers in the polymerase chain reaction (PCR), the synthetic oligonucleotides preferably contain from about 15 to about 30 contiguous nucleotides exactly corresponding to the p18 or p19 of the invention, but may optionally contain additional nucleotides 5' therefrom (Innis, M. A. and Gelfand, D. H., Chapter 1 in *PCR Protocols: A Guide to Methods and Applications*, Innis et al., eds., Academic Press, Inc., New York (1990), pages 3–12; Saiki, R. K., Chapter 2 in *PCR Protocols: A Guide to Methods and Applications*, Innis et al., eds., Academic Press, Inc., New York (1990), pages 13–20). Synthetic amplification products are prepared using the synthetic oligonucleotides of the invention in amplification systems such as PCR (see, e.g., U.S. Pat. No. 4,965,188 to Mullis et al. (Oct. 23, 1990); Scharf, S. J., Chapter 11 in *PCR Protocols: A Guide to Methods and Applications*, Innis et al., eds., Academic Press, Inc., New York (1990), pages 84–98; Chapter 15 in *Current Protocols in Molecular Biology*, Vol. 2, Ausubel et al., eds., John Wiley & Sons, Inc., Boston, Mass. (1994), pages 15.0.1–15.8.8; and Chapter 14 in Sambrook et al., *Molecular Cloning: A Laboratory Manual*, Vol. 2, 2d. Ed., Cold Spring Harbor Laboratory Press, Cold Spring Harbor, N.Y. (1989), pages 14.1–14.35). Those of skill in the art will appreciate that chemical derivatives of nucleotide structures can be substituted for natural nucleotides in the nucleic acids of the invention.

Methods of making proteins: In one aspect of this embodiment of the invention, the nucleic acids of the invention are used to prepare p18 or p19 proteins, or fusion proteins derived from p18 or p19, via recombinant DNA technology. By inserting any of the nucleic acids of the invention that encode p18 or p19 polypeptide sequences into an appropriate expression vector, and introducing the resultant expression vector construct into appropriate host cells, those skilled in the art can produce large quantities of p18 or p19 polypeptides.

There are numerous host/expression vector systems available for the generation of proteins from the isolated nucleic acids of the invention. These include, but are not limited to, bacteria/plasmid systems, bacteria/phage systems, eukaryotic cell/plasmid systems, eukaryotic cell/virus systems, and the like (see, for example, U.S. Pat. No. 4,440,859 to Rutter et al. (Apr. 3, 1984); Chapter 16 in *Current Protocols in Molecular Biology*, Vol. 2, Ausubel et al., eds., John Wiley & Sons, Inc., Boston, Mass. (1994), pages 16.0.5–16.20.16; and Sambrook et al., *Molecular Cloning: A Laboratory Manual*, Vol. 3, 2d. Ed., Cold Spring Harbor Laboratory Press, Cold Spring Harbor, N.Y. (1989)). One skilled in the art can readily adapt the nucleic acids of the invention to any host/expression vector system which is capable of propagating and expressing heterologous nucleic acids to produce the proteins or polypeptides of the invention. Preferred host/expression systems include bacteria/plasmid systems and insect cell/baculoviral expression vector systems.

Diagnostic methods and kits: In another aspect of this embodiment, p18 and p19 nucleic acid sequences are used to prepare oligonucleotide probes, or PCR primers, to serve as materials for diagnostic tests for p18 or p19 expression, mutation, or deletion in samples of cells isolated from mammals. Deletions of the genes encoding p15 and p16 occur frequently in cancer cells, and the resulting loss of their anti-proliferative functions can contribute to tumorigenesis (Noburi et al., *Nature* 368:753–756 (1994)). Similarly, deletions or other mutations in the genes encoding p18 and p19 are diagnostic of cancer or indicative of a predisposition to develop certain types of cancers.

Mutations in the human gene for p19 are detected by any of a variety of methods depending in part on the nature of the mutation of interest. Deletions and insertions of about 100 base pairs (bp) or more are detected by electrophoretic separation of genomic DNA and hybridization analysis using nucleic acid probes preferably derived from the nucleotide sequence of the human p19 coding sequence (SEQ ID NO:8), or by PCR of genomic DNA using synthetic oligonucleotides derived from the nucleotide sequence of the human p19 coding sequence as primers (e.g., SEQ ID NOS:14 and 15).

In one aspect, the invention comprises a method of detecting the presence of a nucleic acid polymorphism associated with a predisposition to develop cancer by analyzing DNA or RNA from a mammal using nucleic acid molecules containing nucleotide sequences from a p19 gene from a mammal, such as a mouse or a human, or the reverse complement thereof. In a parallel aspect, the invention comprises a method of detecting the presence of a DNA polymorphism associated with a predisposition to develop cancer by analyzing DNA or RNA from a non-human mammal using nucleic acid molecules containing nucleotide sequences from a p18 gene from a non-human mammal, such as a mouse, or the reverse complement thereof. Both methods are used in conjunction with any procedure which will detect the nucleic acids of the invention. Examples of such procedures include hybridization analysis using the nucleic acids of the invention, i.e., isolation of nucleic acids from the cells of a mammal, followed by restriction digestion, separation by a means such as gel electrophoresis, transfer to nitrocellulose or a comparable material, and detection of p18 or p19 nucleic acid sequences thereon by exposure to detectably labeled nucleic acid probes which contain nucleotide sequences encoding p18 or p19 polypeptide sequences. The detection procedures are chosen such that they are capable of identifying a polymorphism present within the gene for p18 (InK4c) in a non-human mammal, or for a polymorphism p19, InK4d, in a mammal. In particular, polymorphisms of human InK4d, located on human chromosome 19, are detected by the methods of the invention.

In one embodiment of the present invention, the preferred method of detecting the presence of a DNA polymorphism associated with a predisposition to develop cancer involves RFLP (restriction fragment length polymorphism) techniques based on amplification of p19 sequences via PCR, followed by restriction digestion and agarose gel electrophoresis. In this method, a biological sample containing nucleated cells, preferably leukocytes, is obtained from a human. Suitable biological samples having nucleated cells that may be used in this invention include, but are not limited to, blood and tissue. The method of obtaining the biological sample will vary depending upon the nature of the sample. By the term "nucleated cells" is meant any cell containing a nucleus. Examples of such cells include, but are not limited to, white blood cells, epithelial cells, or mesenchymal cells. The cells are then isolated from the sample and the DNA from the nucleated cells is purified using conventional methods known in the art such as phenolchloroform extraction, lytic enzymes, chemical solutions and centrifugation, or size exclusion chromatography (see, for example, Blin and Stafford, *Nucl. Acid Res.* 3:2303–2308 (1976); Maniatis, *Molecular Cloning: A Laboratory Manual*, Cold Spring Harbor Laboratory, Cold Spring Harbor, N.Y. (1982)). Following isolation, the DNA sequences of interest are amplified using conventional PCR methods (see, for example, Innis et al., *PCR Protocols*, Academic Press, New York (1990); Mullis et al., *Cold Spring Harbor Symp. Quant. Biol.* 51:263–273 (1986); Mullis and Faloona, *Methods Enzymol.* 155:335–350 (1987); and Mullis et al., U.S. Pat. No. 4,965,188 (Oct. 23, 1990)).

In one aspect of this embodiment, sequences flanking the coding sequences for p19 in InK4d are utilized as primers for sequence amplification. In this aspect, the 5' primer is preferably from base 239 to base 263 of the human p19 DNA sequence (SEQ ID NO:7) and has the sequence

AGCAAGGTGCCAGCCCCAATGTCCA (SEQ ID NO: 14).

The 3' primer is preferably the reverse complement of the sequence from base 440 to base 464 of the human p19 DNA sequence (SEQ ID NO:7) and has the sequence

GCGTCCCTGCGATGGAGATCAGATT (SEQ ID NO: 15).

In such an embodiment the amplified product is subjected to restriction digestion prior to visualization. Different alleles of Ink4d will yield amplified fragments of differing size after digestion with an appropriate restriction endonuclease.

The amplified DNA is then precipitated, and digested with a restriction enzyme, such as BamHI, BglII, PstI, or EcoRI.

Digested DNA fragments are separated according to their molecular weights to form a pattern, typically using agarose gel electrophoresis. Following electrophoresis, the gel is stained with an appropriate agent, such as ethidium bromide, using standard protocols, and photographed under ultraviolet transillumination. Polymorphisms result in the appearance of additional bands (i.e., bands not found in the wild-type InK4d allele) on the gel.

In an alternative aspect of this embodiment, the DNA isolated from the cells' nuclei is digested with a given restriction endonuclease, utilizing PCR amplification. The restriction endonucleases that may be used in this invention include, but are not limited to, BamHI, BglII, PstI, or EcoRI. After a digest is obtained, and the DNA is separated by standard technique, for example by agarose gel electrophoresis, the separated bands are probed with a DNA fragment containing sequences encoding human p19 polypeptide sequences. In one aspect of this embodiment, the preferred probe of the invention is based on the cDNA or genomic sequence from the gene for human p19, InK4d, on human chromosome 19.

The use of RFLP technology is only one preferred embodiment of detecting polymorphisms in the nucleic acids of the invention. Since, ultimately, the use of RFLP depends on polymorphism in DNA restriction sites along the nucleic acid molecule, other methods of detecting the polymorphism can also be used. Any method of analysis which allows one skilled in the art to determine the linkage between the polymorphism detected by the probes and primers of the present invention can be utilized. Techniques such as direct location of the polymorphism on chromosome 19 by in situ hybridization using radiolabeled, fluorescence-labeled, or enzyme-labeled probes may be employed. Other suitable techniques include, but are not limited to, amplification methods such as the ribonuclease mis-match cleavage assay and direct oligonucleotide hybridization.

Any size fragment of the human InK4d gene (SEQ ID NO:7) can be utilized as a probe as long as it is capable of hybridizing to a restriction fragment which displays a polymorphism within an intron or an exon in the InK4d gene on chromosome 19. The hybridization probes can be labeled by standard labeling techniques such as with a radiolabel, enzyme label, fluorescent label, biotin-avidin label, chemiluminescence, and the like. After hybridization, the probes are visualized using known methods. Comparison of the RFLP or RFLP's for the subject under investigation will quickly reveal the presence or absence of polymorphisms in the gene encoding human p19 linked to a predisposition to cancer. Polymorphisms that may be detected by the methods of the invention include RFLPs, point mutations, insertions, deletions, inversions, alternately spliced mRNAs, and the like.

The materials for use in this aspect of the invention are ideally suited for the preparation of a kit. Specifically, the invention provides a compartmentalized kit to receive in close confinement, one or more containers which comprises: (a) a first container comprising one or more of the probes or amplification primers of the present invention; and (b) one or more other containers comprising one or more of the following: a sample reservoir, wash reagents, reagents capable of detecting presence of bound probe from the first container, or reagents capable of amplifying sequences hybridizing to the amplification primers.

In detail, a compartmentalized kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (Tris-buffers, etc.), and containers which contain the reagents used to detect the bound probe or amplified product.

Types of detection reagents include labeled secondary probes, or in the alternative, if the primary probe is labeled, the enzymatic, or antibody binding reagents which are capable of reacting with the labeled probe. One skilled in the art will readily recognize that the disclosed probes and amplification primers of the present invention can readily be incorporated into one of the established kit formats which are well known in the art. In one example, a first container may contain a hybridization probe. The second container may contain the restriction enzyme to be used in the digest. Other containers may contain reagents useful in the localization of labeled probes, such as enzyme substrates such as x-gal tagged avidin if a biotinylated probe is utilized. Still other containers may contain buffers, etc.

Genetic and antisense oligonucleotide therapy: In another embodiment of this invention, p18 or p19 nucleic acid sequences are used for genetic therapy, i.e., to inhibit, enhance or restore expression of p18 or p19 in cells with reduced, altered or no p18 or p19 activity, using the nucleic acid sequences of the invention.

1. In order to enhance or restore p18 and/or p19 activity to cells in need of growth regulation, p18, p19 or p18/p19 expression constructs are prepared. An expression construct consists of nucleic acid sequences encoding a protein having p18 polypeptide sequences, nucleic acid sequences encoding a protein having p19 polypeptide sequences, or both types of nucleic acid sequences, operably linked to nucleic acid sequences required for genetic expression in a cell (such as promoters) in an expression vector. The expression constructs are introduced into cells, wherein they direct expression of proteins having p18 or p19 polypeptide sequences, or, in the case of p18/p19 expression constructs, both types of proteins or a single protein having polypeptide sequences from both p18 and p19. The expressed proteins may be fusion proteins that additionally include polypeptide sequences designed to improve the in vivo activity, targeting and/or stability of the gene products expressed by the expression construct.

The expressed proteins function to restore or enhance p18 and/or p19 function in their host cells and thus negatively regulate the progression of the cell through the cell cycle. The disclosure demonstrates that, even in cells genetically engineered to overexpress cyclin D and thus possessing 5–10 fold greater levels of CDKs than corresponding wild-type cells, the constitutive expression of p19 in a cell results in a G1 phase arrest, i.e., inhibition of DNA replication (see Example 7). Thus, even in cells with runaway cyclin D expression, the introduction of p19 function in excess inhibits the progression of the cells through the cell cycle and thus prevents their further growth.

2. In order to inhibit p18 or p19 activity in cells in need of growth stimulation, synthetic antisense oligonucleotides are prepared from the coding sequences for p18 or p19 found in cDNA or genomic clones. An antisense oligonucleotide consists of nucleic acid sequences corresponding to the reverse complements of p18 or p19 coding sequences or other sequences required to be present in p18 or p19 mRNA or DNA molecules for in vivo expression. The antisense oligonucleotides are introduced into cells, wherein they specifically bind to p18 or p19 mRNA molecules (and thus inhibit translation of p18 or p19 gene products), or to double-stranded DNA molecules to form triplexes (see U.S. Pat. No. 5,190,931 to Inouye (Mar. 2, 1993); Riordan and Martin, *Nature* 350:442–443 (1991)).

Because antisense oligonucleotides bind with high specificity to their targets, selectivity is high and toxic side effects resulting from misdirection of the compounds are minimal, particularly given the present state of the art with regard to the design of, preparation and chemical modification of, and means of delivery to cells for, oligonucleotides (see, e.g., Wagner, R. W., *Nature* 372:333–335 (1994); Tseng and Brown, *Cancer Gene Therapy* 1:65–71 (1994); Morishita, R., et al., *J. Clin. Invest.* 93:1458–1464 (1994); Stein and Cheng, *Science* 261:1004–1012 (1993); Lisziewicz, J., et al., *Proc. Natl. Acad. Sci.* (USA) 90:3860–3864 (1993); Watson, P. H., et al., *Cancer Res.* 51:3996–4000 (1991); Han, L., et al., *Proc. Natl. Acad. Sci.* (*USA*) 88:4313–4317 (1991); Florini and Ewton, *J. Biol. Chem.* 265:13435–13437 (1990); and Uhlmann and Peyman, *Chem. Reviews* 90:543–583 (1990)). Means for the delivery of oligonucleotides to cells include, but are not limited to, liposomes (see, e.g., Renneisen, K., etal., *J. Biol. Chem.* 265:16337–16342 (1990)) and introduction of expression constructs that direct the transcription of antisense oligoribonucleotides in vivo (see, e.g., Shohat, O., et al., *Oncogene* 1:277–283 (1987)).

Cells in need of growth stimulation may include stem cells, which both self-renew and differentiate in vivo. Stem cells are pluripotent and give rise to a variety of differentiated cell types; for example, a few hematopoietic stem cells can repopulate the entire hematopoietic system (including white blood cells, red blood cells and platelets) of a lethally-irradiated adult mouse. InK4c-p18 and InK4d-p19 are expressed at high levels in hematopoietic tissues, i.e., bone marrow and spleen. In principle, p18 and/or 19 may likely act to prevent the cycling of hematopoietic stem cells. It is well-known that treatment of cells with FIAU kills cells in cycle but spares hematopoietic stem cells. Therefore, hematopoietic stem cells are, for the most part, non-cycling, and are triggered to enter the cell cycle when new blood cells are needed. A key goal of transplantation therapy is to grow hematopoietic stem cells in vitro, maintaining them in an immature, multipotential state. If these cells are kept out of cycle by CDK inhibitors p18 or p19, then it is possible to move them into the cell cycle by reducing the amount of p18 or p19 present in stem cells by treatment with the antisense oliognucleotides of the invention.

Polypeptides and Related Embodiments

In one embodiment, the invention comprises proteins having amino acid sequences of mouse p19 protein, human p19 protein and p19 polypeptides from other mammals. For example, the invention provides the amino acid sequences of mouse p19 (SEQ ID NO:2) and human p19 (SEQ ID NO:9). In a parallel embodiment, the invention comprises proteins having amino acid sequences of mouse p18 protein and p18 polypeptides from other non-human mammals. For example, the invention provides the amino acid sequence of mouse p18 (SEQ ID NO:1).

One skilled in the art can readily adapt the amino acid sequences of the invention to a variety of known applications. For example, fusion proteins that comprise amino acid sequences from p18 or p19 and a second polypeptide can be produced by recombinant DNA technology to generate novel proteins having properties of both parent proteins (see Example 2). Similarly, the proteins of the invention can be conjugated to other proteins in order to target the conjugated protein to CDK-cyclin complexes in a cell. Synthetic oligopeptides (a.k.a. "peptides") generally contain from about 5 to about 100 contiguous amino acids exactly corresponding to the polypeptide sequence of p18 or p19 of the invention, but may optionally contain additional amino acids at the carboxyl terminus, the amino terminus, or both. Moreover, those of skill in the art will appreciate that substitution of endogenous amino acids for chemical derivatives and/or isomers of amino acids will yield peptides with properties that are enhanced relative to the native p18 or p19 proteins. Properties that may be so altered include, but are not limited to, in vivo stability, affinity for CDK-cyclin complexes, and the like.

Therapeutic Embodiments: Another embodiment of the invention includes identifying and producing drugs based on the p18 and p19 structures that serve as p18 or p19 mimetics to inhibit the activity of endogenous CDKs, with the resultant effect that, when cells are treated therewith, the cells are prevented from progressing through the cell cycle, are inhibited from replicating their chromosomal DNAs, and/or undergo reduced or no cellular growth. Therapeutically, this treatment is used for diseases characterized by uncontrolled cell growth such as cancers, carcinomas, tumors, neoplasms and the like. In a related embodiment, the invention includes identifying and producing drugs based on the p18 and p19 structures that serve as p18 or p19 mimetics to inhibit the activity of endogenous p18 or p19 proteins, with the resultant effect that the cells are stimulated to advance through the cell cycle, are stimulated to replicate their chromosomal DNAs, and/or undergo enhanced cellular growth. This treatment is used in vitro in order to culture cells or therapeutically to promote healing of endogenous tissues or to stimulate the growth of transplanted tissues.

1. As an example of the first therapeutic (anti-cancer) embodiment, p19 is introduced into eukaryotic cells and arrests their progression from G1 to S phases during interphase and thus inhibits the growth of the cells, particularly cells undergoing rapid or uncontrolled growth (see Example 7).

InK4c-p18 and InK4d-p19, or derivatives thereof, i.e., fusion polypeptides (Example 2), peptide fragments generated by proteolysis or synthetic oligopeptides containing different portions of the p18 or p19 polypeptide sequences, can be assayed for their ability to bind CDK4 and CDK6 kinases by using the assay described in Example 3. In this fashion, the polypeptide sequences comprised within CDK-binding motifs are identified. The structure of these polypeptide motifs is used in turn in computer-assisted rational drug design to generate p18 or p19 mimetics that are assayed for their ability to bind CDK4 and/or CDK6 kinases according to the methods of the invention (Martin, Y. C., *Methods in Enzymology* 203:587–613 (1991)).

As another example, mutant p18 or p19 proteins are prepared that bind more tightly to CDK-cyclin complexes, but which inhibit the catalytic (kinase) activity of the CDK-cyclin complexes to the same or greater degree, than wild-type p18 or p19 proteins, respectively, using the assays described herein. These "tight-binding" mutant p18 or p19 proteins, or peptide fragments, oligopeptides or other derivatives thereof, inhibit the activity of endogenous CDKs when introduced into a cell, with the resultant effect that the cells (1) are prevented from progressing through the cell cycle, (2) are inhibited from replicating their chromosomal DNAs, and/or (3) undergo cellular growth at a decreased rate relative to that of untreated cells.

2. A related embodiment of the invention includes screening for and producing compounds that inhibit the activity of p18 or p19, to be applied, either in vitro or in vivo, to cells in need of stimulation of their progression through the cell cycle, DNA replication, and/or cellular growth. Cells in need of such stimulation by the compositions and methods of the invention are hemopoietic cells, which reside in vivo in the bone marrow and spleen of mammals but which cannot be indefinitely maintained in vitro. As an example, p18 or p19 mutant proteins are prepared that retain the ability to bind to CDK-cyclin complexes but which have lost the ability to prevent the catalytic (kinase) activity of the CDKs. These "negative-dominant" mutant p18 or p19 proteins, or peptide fragments, oligopeptides or other derivatives thereof, competitively inhibit endogenous p18 or p19 proteins when introduced into a cell, with the resultant effect that the cells (1) are advanced through the cell cycle, (2) are stimulated to replicate their chromosomal DNAs, and/or (3) undergo cellular growth at an enhanced rate relative to that of untreated cells.

3. The p18 or p19 proteins, fusion proteins, peptide fragments, synthetic oligopeptides or mimetics derived therefrom according to the above embodiments can be employed in combination with conventional excipients, i.e., pharmaceutically acceptable organic or inorganic carrier substances suitable for parenteral application which do not deleteriously react with the active compound. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions preferably oily or aqueous solutions, as well as suspensions, emulsions, or implants. Aqueous suspensions may contain substances which increase the viscosity of the suspension and include, for example, sodium carboxymethyl cellulose, sorbitol, and/or dextran. Optionally, the suspension may also contain stabilizers.

The term "therapeutically effective amount," for the purposes of the invention, refers to the amount of p18 or p19 proteins, fusion proteins, synthetic oligopeptides or mimetics derived therefrom which is effective to achieve its intended purpose. While individual needs vary, determination of optimal ranges for effective amounts of p18 or p19 proteins, fusion proteins, synthetic oligopeptides or mimetics derived therefrom is within the skill of the art. Human doses can be extrapolated from animal studies (Fingle and Woodbury, Chapter 1 in *Goodman and Gilman's The Pharmacological Basis of Therapeutics*, 5th Ed., MacMillan Publishing Co., New York (1975), pages 1–46). Generally, the dosage required to provide an effective amount of the composition, and which can be adjusted by one of ordinary skill in the art will vary, depending on the age, health physical condition, weight, extent of disease of the recipient, frequency of treatment and the nature and scope of the desired effect.

The p18 or p19 proteins, fusion proteins, peptide fragments, synthetic oligopeptides or mimetics derived therefrom, can be delivered to mammals via intermittent or continuous intravenous injection of one or more these compositions or of a liposome (Rahman and Schein, in *Liposomes as Drug Carriers*, Gregoriadis, ed., John Wiley, New York (1988), pages 381–400; Gabizon, A., in *Drug Carrier Systems*, Vol. 9, Roerdink et al., eds., John Wiley, New York (1989), pages 185–212) or microparticle (Tice et al., U.S. Pat. No. 4,542,025 (Sep. 17, 1985)) formulation comprising one or more of these compositions; via subdermal implantation of drug-polymer conjugates (Duncan, R., *Anti-Cancer Drugs* 3:175–210 (1992); via microparticle bombardment (Sanford et al., U.S. Pat. No. 4,945,050 (Jul. 31, 1990)); via infusion pumps (Blackshear and Rohde, in *Drug Carrier Systems*, Vol. 9, Roerdink et al., eds., John Wiley, New York (1989), pages 293–310) or by other appropriate methods known in the art (see, generally, *Remington's Pharmaceutical Sciences*, 18th Ed., Gennaro, ed., Mack Publishing Co., Easton, Pa. (1990)). Of course, the anti-cancer (inhibitory of cell cycle, DNA replication and/or cellular growth) therapeutic compositions of the invention may be used in combination with other anti-cancer compositions known in the art. Similarly, the therapeutic compositions of the invention that stimulate progression through the cell cycle, DNA replication and/or cellular growth may be used in combination with known compositions having like effect.

Treatment of cells with p18 or p19 proteins, fusion proteins, peptide fragments, synthetic oligopeptides or mimetics derived therefrom, results in arrest of the affected cells in the G1 phase of the cell cycle (see Example 7). Accordingly, the outcome of treatment with the therapeutic compositions of the invention is a slowing or cessation of growth of malignant cells with a concomitant reduction in size of the tumor and relief from the primary and secondary symptoms associated with the carcinoma or neoplasm. These and other parameters of neoplasms and carcinomas are measured by methods known in the art (see, generally, Mendelesohn, J., and DeVita, V., in *Harrison's Principles of Internal Medicine*, 11th Ed., Braunwald et al., eds., McGraw-Hill, N.Y. (1987, pages 421–446).

Alternatively, at relatively low doses, the treatment of cells with p18 or p19 proteins, fusion proteins, peptide fragments, synthetic oligopeptides or mimetics derived therefrom, results in G1 arrest in non-neoplastic cells. This modality is used to selectively kill neoplastic cells with therapeutic agents that do not affect normal cells in the G1 phase (Crissman et al., U.S. Pat. No. 5,185,260 (Feb. 9, 1993)). The p18 and p19 proteins or derivatives thereof function in this alternative modality with enhanced selectivity with regard to the G1 kinases (i.e., CDK4, CDK6) and cell types (i.e., hemopoietic and other cells found in the bone marrow and spleen of mammals) that are specifically influenced thereby.

Antibodies and Related Embodiments

In another embodiment of the invention, p18 or p19 proteins, peptide fragments, fusion proteins or oligopeptides derived therefrom, are used to create antibody compositions that specifically recognize (bind) p18 or p19 epitopes. Antibodies to p18 and/or p19 serve as probes for diagnostic tests for p18 and/or p19 expression or as diagnostic materials.

Methods of generating antibodies using purified proteins or synthetic oligopeptides are known in the art (see *Antibodies: A Laboratory Manual*, Harlow, E., and Lane, D., Cold Spring Harbor Laboratory, Cold Spring Harbor (1988)). The antibody compositions of the invention may be polyclonal, monospecific or monoclonal.

Diagnostic methods and kits: In one aspect of this embodiment, the concentration of p18 or p19 protein in a sample of cells from a mammal is determined by contacting the sample with a detectably labeled antibody composition specific to p18 or p19, respectively, qualitatively or quantitatively determining the amount of label bound or not bound in the sample, and calculating therefrom the concentration of p18 or p19 in the sample. The sample of cells is obtained from a mammal and are washed in an appropriate buffer such as Hank's balanced salt solution. In order to release p18 and p19 proteins, the cells and their nuclei are lysed according to methods known in the art (Harlow and Lane, *Antibodies: A Laboratory Manual*, Cold Spring Harbor Laboratory, Cold Spring Harbor (1988), pages 446–460). It may be necessary to add protease inhibitors to the samples to stabilize p18 and p19 proteins (Sambrook et al., *Molecular Cloning: A Laboratory Manual*, 2d. Ed., Cold Spring Harbor Laboratory, Cold Spring Harbor (1989), pages 18.28–18.41), or to preclear samples to remove proteins that bind immunoglobulins non-specifically (Harlow and Lane, *Antibodies: A Laboratory Manual*, Cold Spring Harbor Laboratory, Cold Spring Harbor (1988), pages 461–463; Sambrook et al., *Molecular Cloning: A Laboratory Manual*, 2d. Ed., Cold Spring Harbor Laboratory, Cold Spring Harbor (1989), page 18.43).

The samples are incubated with a detectably labeled p18- or p19-specific antibody composition for an appropriate amount of time, and are washed with the buffer a second time to remove unbound antibody. The amount of bound or unbound labeled antibody is then determined by means known in the art. Suitable types of immunoassays for detecting p18 or p19 include sandwich immunoassay and competition assays, performed using conventional methods (Catty and Raykundalia, in *Antibodies: A Practical Approach, Volume II*, Catty, ed., IRL Press, Oxford (1989), pages 97–154). Other ligands specific for p18 or p19 may be used in lieu of p18- or p19-specific antibodies.

Alternatively, unlabeled p18- or p19-specific antibody compositions, bound or unbound in a sample, are detected using a secondary antibody or protein which is specific for an immunoglobulin, e.g., protein A, protein G, anti-IgM or anti-IgG antibodies. In this alternative embodiment, the secondary (anti-immunoglobulin) antibodies, which may be monoclonal or polyclonal, are detectably labelled and are detected in the course of carrying out the method (Catty and Raykundalia, in Antibodies: A Practical Approach, Volume II, Catty, ed., IRL Press (Oxford) 1989, pages 97–154).

Alternatively, p18 or p19 levels in a sample of mammalian cells are determined by detecting the level of soluble p18 or p19, respectively, in a sample of lysed cells. In this aspect, a sample of lysed cells obtained from a mammal is contacted with a p18- or p19-specific antibody composition which is immobilized onto a solid matrix, and allowed to incubate so as to form a p18/p18-specific antibody or p19/p19-specific antibody complex. Following a wash step with suitable buffers to remove the unbound antibody, a detectably labeled molecule which binds to the p18- or p19-specific antibody composition is added. The amount of bound label then is detected to determine the concentration of p18 or p19 present in the sample (Nakamura and Robbins, in *Manual of Clinical Laboratory Immunology*, 3rd Ed., Rose et al., eds., American Society for Microbiology, Washington, D.C.(1986), pages 116–123).

Of course, the specific amounts of p18- or p19-specific antibody compositions and detectably labeled second antibodies, the temperature and time of incubation, as well as other assay conditions may be varied, depending on various factors including the concentration of p18 or p19 in the sample, the nature of the sample, and the like. Those skilled in the art will be able to determine operative and optimal assay conditions for each determination by employing routine experimentation. Other such steps as washing, stirring, shaking, filtering and the like may be added to the assays as is customary or necessary for the particular situation.

A variety of means may be used to detectably label antibody compositions for use in the methods of the invention. For example, one means by which p18- or p19-specific antibody compositions, or secondary antibodies, can be detectably labeled is by conjugation to an enzyme. The conjugated enzyme, when later exposed to its substrate, will react with the substrate in such a manner as to produce a chemical moiety which can be detected, for example, by spectrophotometric, fluorometric or by visual means. Enzymes which can be used to detectably label antibody compositions include, but are not limited to, malate dehydrogenase, staphylococcal nuclease, delta-v-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase. Antibody compositions may also be labeled with a radioactive isotope which can be determined by such means as the use of a gamma counter or a scintillation counter or by autoradiography. It is also possible to label antibody compositions with a fluorescent compound. When fluorescently labeled antibody is exposed to light of the proper wave length, its presence can then be detected due to the fluorescence of the dye. Among the most commonly used fluorescent labeling compounds are fluorescein isothiocyanate, rhodamine, phycoerythrin, phycocyanin, allophycocyanin, o-phthaldehyde and fluorescamine. Antibodies can also be detectably labeled using fluorescence emitting metals such as $^{152}$Eu, or others of the lanthanide series. These metals can be attached to p18- or p19-specific antibodies using such metal chelating groups as diethylenetriaminepentaacetic acid (DTPA) or ethylenediaminetetraacetic acid (EDTA). Antibodies also can be detectably labeled by coupling to a chemiluminescent compound. The presence of chemiluminescent-tagged antibodies is then determined by detecting the presence of luminescence that arises during the course of a chemical reaction. Examples of particularly useful chemiluminescent labeling compounds are luminol, isoluminol, theromatic acridium ester, imidazole, acridinium salt and oxalate ester. Likewise, a bioluminescent compound may be used to label antibody compositions for use in the methods of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of bound or unbound antibodies may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

In another embodiment of the present invention, kits are provided which contain the necessary reagents to carry out the previously described immunoassays with p18- or p19-specific antibodies, in order to diagnose certain types of cancers, or to detect a predisposition for certain types of cancers, in a mammal.

Specifically, the invention provides a compartmentalized kit to receive, in close confinement, one or more containers which comprises: (a) a first container containing a p18- or p19-specific antibody; and (b) one or more other containers containing one or more of the following: wash reagents, and reagents capable of detecting presence of bound or unbound p18- or p19-specific antibodies.

In detail, a compartmentalized kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody.

Types of detection reagents include detectably labeled secondary antibodies, or in the alternative, if the primary antibody is detectably labeled, the appropriate enzymatic or antibody binding reagents which are capable of reacting with the labeled antibody. One skilled in the art will readily recognize that the disclosed antibodies of the present invention can readily be incorporated into any one of the variety of established kit formats which are well known in the art.

Transgenic Animals and Related Embodiments In another embodiment of the invention, p18 or p19 nucleic acid sequences can be used to create transgenic non-human animals to serve as animal models for p18 or p19 overexpression (transgenic expression) or mutations such as deletions ("knockouts" or "null alleles") or other mutations which alter one or more p18 or p19 activities. For example, transgenic mice having little or no p19 activity due to mutations in one or both alleles of the gene for p19 (ink4d) are prone to develop certain types of tumors. Other examples include transgenic mice having little or no p18 activity due to mutations in one or both alleles of the gene for p18 (ink4c), and transgenic mice deficient in both p18 and p19 activity.

The non-human animals of the invention comprise any animal having a deficiency of p18 and/or p19 activity as a result of the transgenic interruption or alteration of the gene(s) encoding p18 and/or p19. Such non-human animals include vertebrates such as rodents, non-human primates, sheep, dog, cow, amphibians, reptiles, etc. Preferred non-human animals are selected from non-human mammalian species of animals, most preferably, animals from the rodent family including rats and mice, most preferably mice.

The transgenic animals of the invention are animals into which has been introduced by nonnatural means (i.e., by human manipulation), one or more genes that do not occur naturally in the animal, e.g., foreign genes, genetically engineered endogenous genes, etc. The nonnaturally introduced genes, known as transgenes, may be from the same or a different species as the animal but not naturally found in the animal in the configuration and/or at the chromosomal locus conferred by the transgene. Transgenes may comprise foreign DNA sequences, i.e., sequences not normally found in the genome of the host animal. Alternatively or additionally, transgenes may comprise endogenous DNA sequences that are abnormal in that they have been rearranged or mutated in vitro in order to alter the normal in vivo pattern of expression of the gene, or to alter or eliminate the biological activity of an endogenous gene product encoded by the gene. (Watson, J. D., et al., in *Recombinant DNA*, 2d Ed., W. H. Freeman & Co., New York (1992), pages 255–272; Gordon, J. W., *Intl. Rev. Cytol.* 115:171–229 (1989); Jaenisch, R., *Science* 240:1468–1474 (1989); Rossant, J., *Neuron* 2:323–334 (1990)).

Methods of preparing transgenic animals: In one aspect of this embodiment of the invention, the nucleic acids of the invention are used to prepare transgenic constructs to be introduced into non-human animals in order to generate the transgenic animals of the invention. Specifically, p18 or p19 sequences derived from the genome of the non-human animal of choice are used to create such transgenic constructs.

The transgenic non-human animals of the invention are produced by introducing p18 and/or p19 transgenic constructs into the germline of the non-human animal. Embryonic target cells at various developmental stages are used to introduce the transgenes of the invention. Different methods are used depending on the stage of development of the embryonic target cell(s).

1. Microinjection of zygotes is the preferred method for incorporating transgenes into animal genomes in the course of practicing the invention. A zygote, a fertilized ovum that has not undergone pronuclei fusion or subsequent cell division, is the preferred target cell for microinjection of transgenic DNA sequences. The murine male pronucleus reaches a size of approximately 20 micrometers in diameter, a feature which allows for the reproducible injection of 1–2 picoliters of a solution containing transgenic DNA sequences. The use of a zygote for introduction of transgenes has the advantage that, in most cases, the injected transgenic DNA sequences will be incorporated into the host animal's genome before the first cell division (Brinster, et al., *Proc. Natl. Acad. Sci.* (*USA*) 82:4438–4442 (1985)). As a consequence, all cells of the resultant transgenic animals (founder animals) stably carry an incorporated transgene at a particular genetic locus, referred to as a transgenic allele. The transgenic allele demonstrates Mendelian inheritance: half of the offspring resulting from the cross of a transgenic animal with a non-transgenic animal will inherit the transgenic allele, in accordance with Mendel's rules of random assortment.

2. Viral integration can also be used to introduce the transgenes of the invention into an animal. The developing embryos are cultured in vitro to the developmental stage known as a blastocyte. At this time, the blastomeres may be infected with appropriate retroviruses (Jaenich, R., *Proc. Natl. Sci.* (*USA*) 73:1260–1264). Infection of the blastomeres is enhanced by enzymatic removal of the zona pellucida (Hogan, et al., in *Manipulating the Mouse Embryo*, Cold Spring Harbor Press, Cold Spring Harbor, N.Y. (1986)). Transgenes are introduced via viral vectors which are typically replication-defective but which remain competent for integration of viral-associated DNA sequences, including transgenic DNA sequences linked to such viral sequences, into the host animal's genome (Jahner, et al., *Proc. Natl. Acad. Sci.* (*USA*) 82:6927–6931 (1985); Van der Putten, et al., *Proc. Natl. Acad. Sci.* (*USA*) 82:6148–6152 (1985)). Transfection is easily and efficiently obtained by culture of blastomeres on a mono-layer of cells producing the transgene-containing viral vector (Van der Putten, et al., *Proc. Natl. Acad. Sci.* (*USA*) 82:6148–6152 (1985); Stewart, et al., *EMBO Journal* 6:383–388 (1987)). Alternatively, infection may be performed at a later stage, such as a blastocoele (Jahner, D., et al., *Nature* 298:623–628 (1982)). In any event, most transgenic founder animals produced by viral integration will be mosaics for the transgenic allele; that is, the transgene is incorporated into only a subset of all the cells that form the transgenic founder animal. Moreover, multiple viral integration events may occur in a single founder animal, generating multiple transgenic alleles which will segregate in future generations of offspring. Introduction of transgenes into germline cells by this method is possible but probably occurs at a low frequency (Jahner, D., et al., *Nature* 298:623–628 (1982)). However, once a transgene has been introduced into germline cells by this method, offspring may be produced in which the transgenic allele is present in all of the animal's cells, i.e., in both somatic and germline cells.

3. Embryonic stem (ES) cells can also serve as target cells for introduction of the transgenes of the invention into animals. ES cells are obtained from pre-implantation embryos that are cultured in vitro (Evans, M. J., et al., *Nature* 292:154–156 (1981); Bradley, M. O., et al., *Nature* 309:255–258 (1984); Gossler, et al., *Proc. Natl. Acad. Sci.* (*USA*) 83:9065–9069 (1986); Robertson et al., *Nature* 322:445–448 (1986); Robertson, E. J., in *Teratocarcinomas and Embryonic Stem Cells: A Practical Approach*, Robertson, E. J., ed., IRL Press, Oxford (1987), pages 71–112). ES cells, which are commercially available (from, e.g., Genome Systems, Inc., St. Louis, Mo.), can be transformed with one or more transgenes by established methods (Lovell-Badge, R. H., in *Teratocarcinomas and Embryonic Stem Cells: A Practical Approach*, Robertson, E. J., ed., IRL Press, Oxford (1987), pages 153–182). Transformed ES cells can be combined with an animal blastocyst, whereafter the ES cells colonize the embryo and contribute to the germline of the resulting animal, which is a chimera (composed of cells derived from two or more animals) (Jaenisch, R., *Science* 240:1468–1474 (1988); Bradley, A., in *Teratocarcinomas and Embryonic Stem Cells: A Practical Approach*, Robertson, E. J., ed., IRL Press, Oxford (1987), pages 113–151). Again, once a transgene has been introduced into germline cells by this method, offspring may be produced in which the transgenic allele is present in all of the animal's cells, i.e., in both somatic and germline cells.

However it occurs, the initial introduction of a transgene is a Lamarckian (non-Mendelian) event. However, the transgenes of the invention may be stably integrated into germ line cells and transmitted to offspring of the transgenic animal as Mendelian loci. Other transgenic techniques result in mosaic transgenic animals, in which some cells carry the transgenes and other cells do not. In mosaic transgenic animals in which germ line cells do not carry the transgenes, transmission of the transgenes to offspring does not occur. Nevertheless, mosaic transgenic animals are capable of demonstrating phenotypes associated with the transgenes.

Transgenes may be introduced into animals in order to provide animal models for human diseases. Transgenes that result in such animal models include, e.g., transgenes that encode mutant gene products associated with an inborn error of metabolism in a human genetic disease and transgenes that encode a human factor required to confer susceptibility to a human pathogen (i.e., a bacterium, virus, or other pathogenic microorganism) (Leder et al., U.S. Pat. No. 5,175,383 (Dec. 29, 1992); Kindt et al., U.S. Pat. No. 5,183,949 (Feb. 2, 1993); Small et al., *Cell* 46:13–18 (1986); Hooper et al., *Nature* 326:292–295 (1987); Stacey et al., *Nature* 332:131–136 (1988); Windle et al., *Nature* 343:665–669 (1990); Katz et al., *Cell* 74:1089–1100 (1993)). Transgenic animals that are predisposed to a disease may be used to identify compositions that induce the disease and to evaluate the pathogenic potential of compositions known or suspected to induce the disease (Berns, A. J. M., U.S. Pat. No. 5,174,986 (Dec. 29, 1992)). The transgenic animals of the invention are predisposed to develop, and thus serve as animal models for, certain types of carcinomas and neoplasms.

Offspring that have inherited the transgenes of the invention are distinguished from littermates that have not inherited transgenes by analysis of genetic material from the offspring for the presence of biomolecules that comprise unique sequences corresponding to sequences of, or encoded by, the transgenes of the invention. For example, biological fluids that contain polypeptides uniquely encoded by the transgenes of the invention may be immunoassayed for the presence of the polypeptides. A more simple and reliable means of identifying transgenic offspring comprises obtaining a tissue sample from an extremity of an animal, e.g., a tail, and analyzing the sample for the presence of nucleic acid sequences corresponding to the DNA sequence of a unique portion or portions of the transgenes of the invention. The presence of such nucleic acid sequences may be determined by, e.g., hybridization ("Southern") analysis with DNA sequences corresponding to unique portions of the transgene, analysis of the products of PCR reactions using DNA sequences in a sample as substrates and oligonucleotides derived from the transgene's DNA sequence, etc. To produce transgenic animals having both p18 and p19 transgenes, transgenic p18 mice are mated with transgenic p19 mice, and the resulting offspring are screened for the presence of both p18 and p19 transgenes.

Null alleles: A preferred embodiment is a transgenic animal that is homozygous for a null (a.k.a. "knock-out") allele of Ink4c (encodes p18), or for Ink4d (encodes p19), or both Ink4c and Ink4d. These animals are predisposed to develop certain types of cancers in a reproducible and thus reliable manner. In order to generate null alleles in Ink4c and Ink4d in embryonic stem cells, the positive-negative selection strategy of Mansour et al. (*Nature* 336:348–352 (1988)) is applied. A positive selectable marker, for example the hygromycin phosphotransferase cassette (van Deursen and Wieringa, *Nucl. Acids Res.* 29:3815–3820 (1992)), is inserted into a 5' portion of an Ink4 gene. This position for the positive selectable marker is chosen to obtain a genuine null mutant allele, i.e., to avoid translation of a truncated polypeptide. In the resulting targeting vector the hygromycin gene is flanked 5' and 3' by several kb of homologous murine genomic sequences. In addition, a negative selectable marker, for example the Herpes Simplex Virus (HSV) thymidine kinase (TK) gene, is placed in a 3' position flanking the region of homologous sequences in order to enable selection against nonhomologous integrants. Both the positive and negative selectable markers are inserted in the antisense orientation with respect to the transcriptional orientation of the Ink4 gene, and are expressed due to the TK promoter and Py F441 Polyoma enhancer. Linearized targeting construct is introduced into ES cells by electroporation or other suitable means and selection with hygromycin and FIAU (1-[2-deoxy, 2-fluoro-β-D-arabinofuranosyl]) is carried out for 7 to 10 days. Resistant colonies are expanded in 24-well plates; half of the cells in each well are cryopreserved and the other half expanded for genotype analysis. Positive clones are stored in liquid nitrogen and thawed at least 3 days prior to blastocyst injection. Blastocysts are isolated, for example, at day 3.5 postcoitum by flushing the uterine horns of naturally mated C57BL/6 pregnant females with DMEM+10% FBS. Approximately 10 to 15 ES cells from each homologous recombinant clone with a normal karyotype are microinjected into recipient blastocysts, and about 10 to 20 embryos are transferred into the uterine horns of (C57BL/6×CBA/Ca)F1 pseudopregnant fosters (Bradley, A., in *Teratocarcinomas and Embryonic Stem Cells. A Practical Approach*, Robertson, E. J., ed., IRL Press, Oxford (1987), pages 113–151). Chimeric males are mated with C57BL/6 or FVB/J females and germline transmission of the mutant allele is verified by Southern blot analysis of tail DNA from F1 offspring with either agouti or gray coat color. F2 offspring from interbred heterozygotes are genotyped by Southern blotting to identify homozygous null mutants.

Methods of evaluating the therapeutic or oncogenic potential of compositions: Using the transgenic animals of the invention, it is possible to evaluate a variety of compositions for their therapeutic or oncogenic potential.

1. Generally, methods for determining the therapeutic potential of a composition to treat cancer comprise the step of administering a known dose of the composition to transgenic animals having a phenotype of reduced or altered p18 and/or p19 activity, monitoring resulting biological or biochemical parameters correlated with cancer, and comparing the symptoms of treated animals to those of untreated animals.

A first method of assessing the therapeutic potential of a composition using the transgenic animals of the invention comprises the steps of:

(1) Administering a known dose of the composition to a first transgenic animal having a phenotype of reduced or altered p18 and/or p19 activity;

(2) Detecting the time of onset of cancer in the first transgenic animal; and (3) Comparing the time of onset of cancer in the first transgenic animal to the time of onset of cancer in a second transgenic animal having a phenotype of reduced or altered p18 and/or p19 activity, which has not been exposed to the composition, wherein a statistically significant decrease in the time of onset of cancer in the first transgenic animal relative to the time of onset of the symptoms in the second transgenic animal indicates the therapeutic potential of the composition for treating cancer.

A second method of assessing the therapeutic potential of a composition using the transgenic animals of the invention comprises the steps of:

(1) Administering a known dose of the composition to a first transgenic animal having a phenotype of reduced or altered p18 and/or p19 activity, at an initial time, $t_0$;

(2) Determining the extent of cancer in the first transgenic animal at a later time, $t_1$; and (3) Comparing, at $t_1$, the extent of cancer in the first transgenic animal to the extent of cancer in a second transgenic animal having a phenotype of reduced or altered p18 and/or p19 activity, which has not been exposed to the composition at $t_0$, wherein a statistically significant decrease in the extent of cancer at $t_1$ in the first transgenic animal relative to the extent of the symptoms at $t_1$ in the second transgenic animal indicates the therapeutic potential of the composition for treating cancer.

A third method of assessing the therapeutic potential of a composition using the transgenic animals of the invention comprises the steps of:

(1) Administering a known dose of the composition to a first transgenic animal having a phenotype of reduced or altered p18 and/or p19 activity;

(2) Measuring the lifespan of the first transgenic animal; and (3) Comparing the lifespan of the first transgenic animal to the lifespan of a second transgenic animal having a phenotype of reduced or altered p18 and/or p19 activity, which has not been exposed to the composition, wherein a statistically significant increase in the lifespan of the first transgenic animal relative to the lifespan of the second transgenic animal indicates the therapeutic potential of the composition for treating cancer.

2. Generally, methods for determining the potential of a composition to cause or exacerbate cancer comprise the step of administering a known dose of the composition to a transgenic animals having a phenotype of reduced or altered p18 and/or p19 activity, monitoring resulting biological or biochemical parameters correlated with cancer, and comparing the symptoms of treated animals to those of untreated animals.

A first method of assessing the oncogenic potential of a composition using the transgenic animals of the invention comprises the steps of:

(1) Administering a known dose of the composition to a first transgenic animal having a phenotype of reduced or altered p18 and/or p19 activity;

(2) Detecting the time of onset of cancer in the first transgenic animal; and (3) Comparing the time of onset of cancer in the first transgenic animal to the time of onset of cancer in a second transgenic animal having a phenotype of reduced or altered p18 and/or p19 activity, which has not been exposed to the composition, wherein a statistically significant increase in the time of onset of cancer in the first transgenic animal relative to the time of onset of the symptoms in the second transgenic animal indicates the potential of the composition for causing or exacerbating cancer.

A second method of assessing the oncogenic potential of a composition using the transgenic animals of the invention comprises the steps of:

(1) Administering a known dose of the composition to a first transgenic animal having a phenotype of reduced or altered p18 and/or p19 activity, at an initial time, $t_0$;

(2) Determining the extent of cancer in the first transgenic animal at a later time, $t_1$; and (3) Comparing, at $t_1$, the extent of cancer in the first transgenic animal to the extent of neurological symptoms in a second transgenic animal having a phenotype of reduced or altered p18 and/or p19 activity, which has not been exposed to the composition at $t_0$, wherein a statistically significant increase in the extent of cancer at $t_1$ in the first transgenic animal relative to the extent of the symptoms at $t_1$ in the second transgenic animal indicates the potential of the composition for causing or exacerbating cancer.

A third method of assessing the oncogenic potential of a composition using the transgenic animals of the invention comprises the steps of:

(1) Administering a known dose of the composition to a first transgenic animal having a phenotype of reduced or altered p18 and/or p19 activity;

(2) Measuring the lifespan of the first transgenic animal; and (3) Comparing the lifespan of the first transgenic animal to the lifespan of a second transgenic animal having a phenotype of reduced or altered p18 and/or p19 activity, which has not been exposed to the composition, wherein a statistically significant decrease in the lifespan of the first transgenic animal relative to the lifespan of the second transgenic animal indicates the potential of the composition for causing or exacerbating cancer.

3. In both of the above sets of methods, the composition may comprise a chemical compound administered by circulatory injection or oral ingestion. The composition being evaluated may alternatively comprise a polypeptide administered by circulatory injection of an isolated or recombinant bacterium or virus that is live or attenuated, wherein the polypeptide is present on the surface of the bacterium or virus prior to injection, or a polypeptide administered by circulatory injection of an isolated or recombinant bacterium or virus capable of reproduction within a mouse, and the polypeptide is produced within a mouse by genetic expression of a DNA sequence encoding the polypeptide. Alternatively, the composition being evaluated may comprise one or more nucleic acids, including a gene from the human genome or a processed RNA transcript thereof.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

The entire text of all publications cited above and below are hereby incorporated by reference.

EXAMPLE

Example 1

Cloning of the Mouse p18 and p19 cDNAs

The yeast two-hybrid screen of Bartel et al. (In *Cellular Interactions in Development: A Practical Approach*, Hartley, D. A., ed., Oxford University Press, Oxford UK (1993), pages 153–179) as modified by Durfee et al. (*Genes & Devel.* 7:555–569 (1993)) was used to isolate cDNAs from a mouse T cell lymphoma library encoding proteins able to interact with CDK4. A BamHI fragment encoding the entire open reading frame of mouse CDK4 (Matsushime et al., *Cell* 71:323–334 (1992)) was inserted into the BamHI site of the plasmid, pAS2, which contains the TRP1 and CYH genes conferring auxotrophy to tryptophan and sensitivity to cycloheximide, respectively (Durfee et al., *Genes & Devel.* 7:555–569 (1993)). The resulting "bait" plasmid (pAS2cdk4) drives the expression from the alcohol dehydrogenase promotor of a GAL4-CDK4 fusion protein containing amino terminal GAL4 DNA binding sequences (amino acids 1–147). Screening was performed using yeast strain Y190, which expresses two GAL4-inducible markers, HIS3 and LacZ. Y190 cells containing pAS2-CDK4 were transformed with LEU2 pACT plasmids containing cDNAs (prepared from mouse T lymphoma cells) which were fused 3' to the GAL4 transcriptional activation domain (Clontech, Palo Alto, Calif.). Transformants were plated and selected for 9 days at 30° C. on SD synthetic medium lacking leucine, tryptophan, and histidine and containing 50 mM 3-amino-1,2,4-triazole (3-AT). Of $1.6 \times 10^7$ transformants, 327 HIS$^+$ colonies were obtained, which were transferred to Hybond-N nylon filters (Amersham, Arlington Heights, Ill.), frozen at −70° C. for 15 minutes, thawed, and overlaid on Whatman 3M paper containing 60 mM $Na_2HPO_4$, 40 mM $NaH_2PO_4$, 10 mM KCl, 1 mM $MgSO_4$, 40 mM β-mercaptoethanol, and 0.033% X-gal. After incubation for 20 hrs. at 30°, 158 blue colonies were identified and streaked on SD synthetic medium lacking leucine and containing 2.5 or 10 ug/ml cycloheximide in order to segregate pAS2-CDK4, and the surviving colonies were restreaked on medium lacking either leucine or tryptophan to confirm plasmid segregation. Ninety-nine such colonies were mated with yeast strain Y187 containing either pAS2-CDK4 or plasmids encoding other transactivating GAL4 fusion proteins (including the yeast kinase SNF1 and human lamin) by coincubation in YPD medium for 15 hr at 30° C., and the progeny were streaked on SD synthetic medium lacking leucine, tryptophan, histidine and containing 50 mM 3-AT. Eighty-three library plasmids which activated HIS3 and LacZ only in the presence of GAL4-CDK4 were isolated from yeast and used to transform *Escherichia coli* strain HB101. The *E. coli* transformants were cultivated, and the 83 library-derived plasmids were individually purified therefrom.

Positive plasmids were dot-blotted onto Hybond N filters and hybridized for 20 hours at 42° C. with a $^{32}$P-labeled cyclin D probe (a 1:1:1 mixture of mouse cyclins D1, D2, and D3) in 3× SSC (1× SSC is 0.15 M NaCl, 0.015 M Na citrate) containing 35% formamide. Filters were washed in 1× SSC containing 0.1% sodium dodecyl sulfate (SDS) for 30 minutes at 65° C., yielding 29 cyclin-positive clones. Several of the 54 remaining plasmid DNAs chosen at random were radiolabeled by nick translation and rehybridized to the filters, ultimately describing several families of related sequences. The nucleotide sequences of cDNA inserts from representative plasmids of each group were determined using a Sequenase version 2.0 kit (USB, Cleveland, Ohio.).

Of the 83 isolated library-derived plasmids, 29 contained cDNAs encoding D-type cyclins. Eighteen plasmids contained 9 sets of less abundant gene sequences, none of which showed significant homology to known sequences in GenBank. Thirty-six plasmids contained the coding sequences of two novel Ink4-related genes, which are here designated "p19" (represented by 29 clones) and "p18" (represented by 7 clones). The InK4 proteins were initially designated based upon their apparent molecular masses; when the two cDNAs were transcribed and translated in vitro and electrophoretically separated in parallel on a denaturing 15% polyacrylamide gel, the p19 product migrated more slowly than the p18 product. However, the nucleotide sequences of these two mouse InK4 family members predict polypeptides of 166 (p19) and 168 (p18) amino acids with molecular masses of 18,005 and 18,176 daltons, respectively.

Based on their predicted amino acid sequences, the two mouse InK4 proteins are approximately 40% identical to one another and share a similar degree of amino acid homology with the previously described human $p16^{InK4a}$ and $p15^{InK4b}$ polypeptides. Like the latter proteins, p19 and p18 are composed of tandem ankyrin motifs, each about 32 amino acids in length (FIG. 1, Panel A). The most highly conserved regions of mouse p19 and p18 include the amino acid sequences comprising repeats 1–3 and half of repeat 4. The most conserved repeats of p16, p18, and p19 can be aligned with one another as well as with those of other InK4 family members (FIG. 1, Panel B). After completion of this work, the cloning and sequencing of a cDNA molecule encoding human p18 was reported (Guan et al., *Genes & Devel.* 8:2939–2952 (1994)). The human and mouse p18 polypeptides, each 168 amino acids in length, are identical over 153 residues.

Mouse p19 and p18 exhibit only about 40% amino acid identity to one another, and both show a similarly limited degree of homology to human p16$^{InK4a}$ and p15$^{InK4b}$. In contrast, mouse p19 and p18 exhibit >90% amino acid identity with their human counterparts. Human p16 and p15 map in tandem on the short arm of human chromosome 9 (Kamb et al., Science 264:436–440 (1994)). The gene for human p18 has been assigned to chromosome 1 (Guan et al., Genes & Devel. 8:2939–2952 (1994)), indicating that the InK4 family includes a minimum of four distinct genes. We therefore suggest that the p18 and p19 genes be designated Ink4c and Ink4d, respectively.

Example 2

Production of Mouse p18 and p19 Fusion Proteins

Fragments containing the entire coding sequences for p19 were amplified by PCR using the following oligonucleotide primers:

CCGGATCCATGCTTCTGGAAGAAGT (5' primer) (SEQ ID NO:12); and

CCGAATTCTCACATTGGGATCATCA (3' primer) (SEQ ID NO:13).

Fragments containing the entire coding sequences for p18 were amplified by PCR using the following oligonucleotide primers:

CCGGATCCATGGCCGAGCCTTGGGG (5' primer) (SEQ ID NO:10); and

CCGAATTCTCACTGCAGGCTTGTGG (3' primer) (SEQ ID NO:11).

The underlined ATGs in the sense strand oligonucleotides correspond to the p19 and p18 initiator codons, which were preceded by BamHI sites to enable subsequent cloning. Products digested with BamHI and EcoRI were inserted into pGEX-3X (Pharmacia, Uppsala, Sweden) in frame with GST. pGST-MAD3, a plasmid encoding mouse IκB, and pGST-ANK6, which encodes the MAD3 subdomain containing only the five ankyrin repeats (amino acids 73–242), were kindly provided by Dr. Lawrence Kerr (Vanderbilt University, Nashville, Tenn.).

Overnight cultures of bacteria transformed with plasmids encoding the GST fusion proteins were diluted 10-fold with fresh media and cultured for 2–4 hours at 37° C. Recombinant proteins were induced with 1 mM isopropyl-β-D-thiogalactoside (IPTG) for 1 hour at 37° C., and the harvested cells were lysed by sonication in phosphate-buffered saline (PBS) containing 1% Triton X-100 and clarified by centrifugation. GST fusion proteins were adsorbed to glutathione-Sepharose beads (Pharmacia), washed with 50 mM Tris HCl (pH 7.5), and eluted in the same buffer containing 5 mM reduced glutathione (Sigma, St Louis, Mo.). Proteins were dialyzed against 50 mM Hepes (pH 7.5), 150 mM NaCl, and 1 mM EDTA and quantitated with a bicinchoninic acid assay kit (Pierce, Rockford, Ill.) using bovine serum albumin (BSA) as a protein standard.

Example 3

Mouse InK4 Proteins Specifically Bind to and Inhibit CDK4 and CDK6 Kinases

CDK Binding Assays

Human InK4 polypeptides specifically bind to the cyclin D-dependent catalytic subunits, CDK4 and CDK6 (5,18,45). To study the interactions of mouse p19 and p18 with CDKs, cDNAs encoding CDC2 (CDK1) and CDKs 2–6 were transcribed and translated in vitro, and the radiolabeled products were mixed with GST-tagged p19 and p18 fusion proteins adsorbed to glutathione-Sepharose beads or to GST-Sepharose beads as a control.

Plasmids derived from pBluescript and containing the entire coding sequences of the mouse cdk2, cdk4, cdk5, or cdk6 genes (Matsuoka et al., Mol. Cell. Biol. 14:7265–7275 (1994); Matsushime et al., Cell 71:323–334 (1992)) or human cdc2/cdk1 or cdk3 genes (provided by Drs. Matthew Meyer-son and Edward Harlow (MGH Cancer Center, Cambridge, Mass.)) were transcribed and translated in vitro (Matsuoka et al., Mol. Cell. Biol. 14:7265–7275 (1994)). Mouse cdk6 cDNA was cloned from a mouse macrophage library (Stratagene, La Jolla, Calif.) by screening with a full-length human cdk6 clone (also provided by M. Meyerson and E. Harlow). Following transcription and translation, rabbit reticulocyte lysates containing $^{35}$S-methionine labeled CDKs (20–40 ul) were diluted to 0.5 ml in IP kinase buffer (50 mM Hepes, pH 7.5, containing 150 mM NaCl, 1 mM EDTA, 1 mM DTT, 0.1% Tween-20) containing 10 mg/ml BSA and mixed with 1 ug of purified GST or GST-p19 immobilized on glutathione-Sepharose beads. After 2 hours of incubation at 4° C., beads were collected by centrifugation, washed 4 times in IP kinase buffer, and the bound proteins were denatured and analyzed by electrophoresis on 12.5% polyacrylamide gels containing SDS (Anderson, S. J., et al., J. Virol. 51:730–741 (1984)).

Figure 2B:
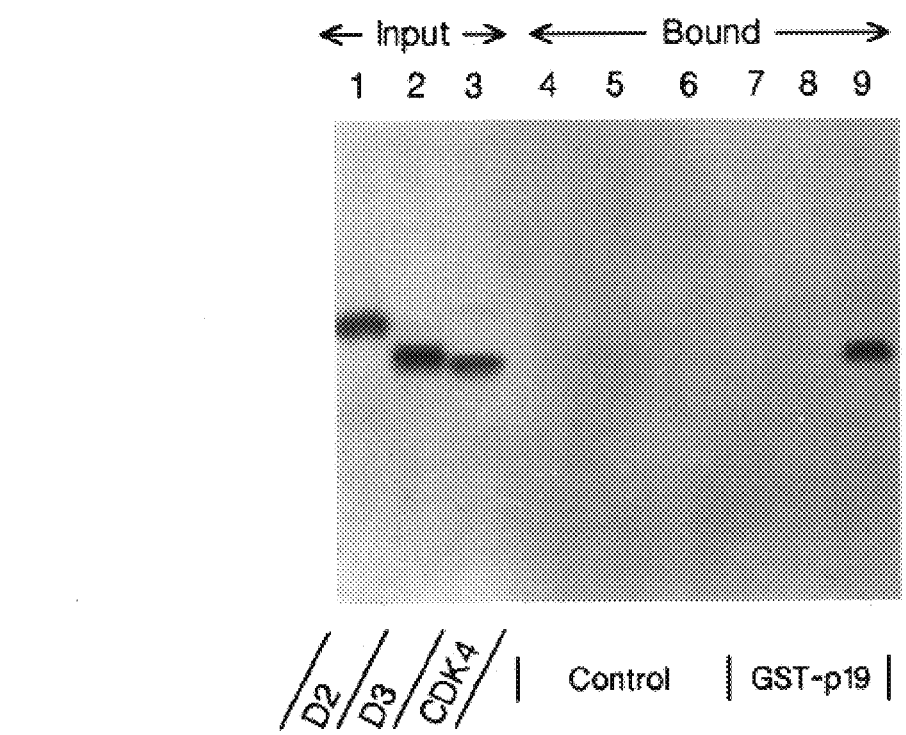
Figure 3A:
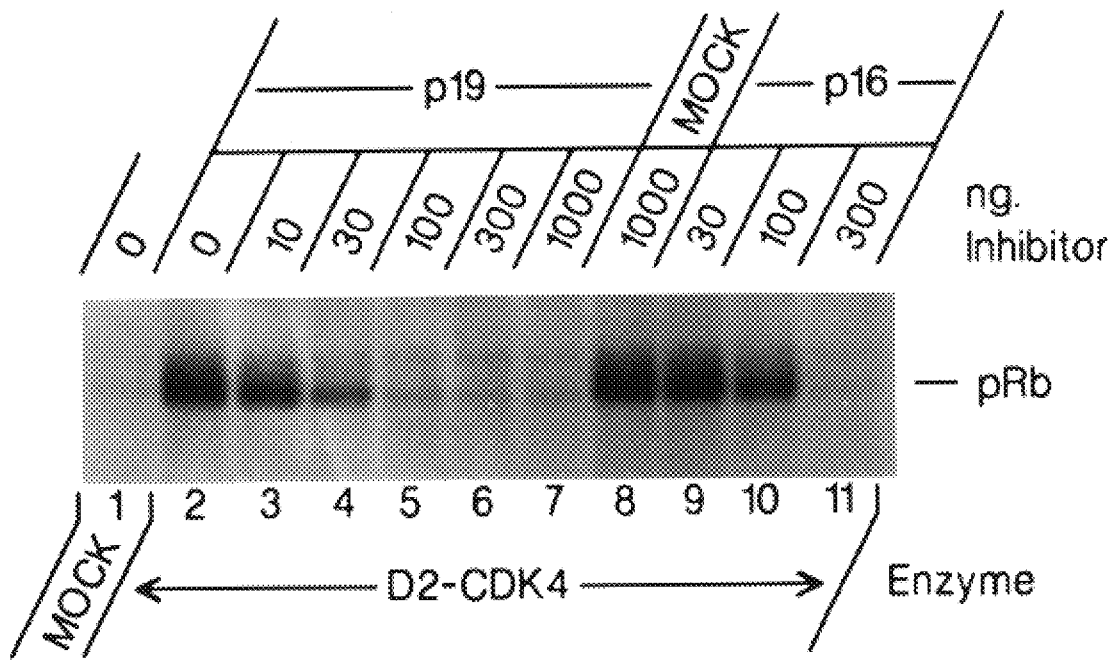
FIG. 3 presents results demonstrating that p19 and p18 inhibit the pRb kinase activities of CDK4-cyclin D and CDK6-cyclin D. Active holoenzyme complexes composed of CDK4-cyclin D2 (panels A and C) and CDK6-cyclin D2 (panels B and D) were produced in insect Sf9 cells coinfected with the appropriate vectors (Kato et al., Genes & Devel. 7:331–342 (1993)). Sf9 extracts infected with a wild-type baculovirus were used as controls for background kinase activity (lane 1 (mock) in all panels)). GST fusion proteins containing the complete coding sequences of mouse p19, mouse p18 or human p16 were purified and eluted from glutathione-Sepharose beads, and the amounts of protein (ng) indicated above each lane were added to fixed quantities of Sf9 lysates containing the indicated enzymes. The extracts were then assayed for pRb kinase activity as described (Kato et al., Genes & Devel. 7:331–342 (1993)) and the products resolved on denaturing gels. Panels C and D include similar experiments using GST proteins containing either mouse IκB (MAD3) (lanes 9 and 10) or a subdomain of the protein (amino acids 73–242) containing its ankyrin repeats (lanes 11 and 12). The autoradiographic exposure times were 15 hrs.
Figure 3B:
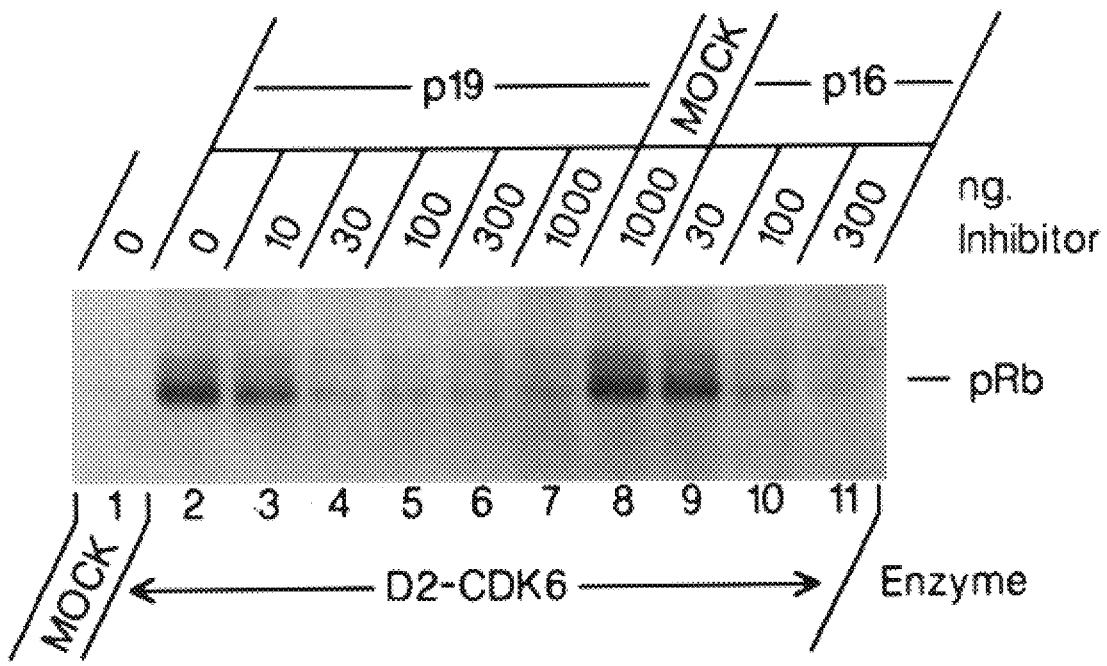
Figure 3C:
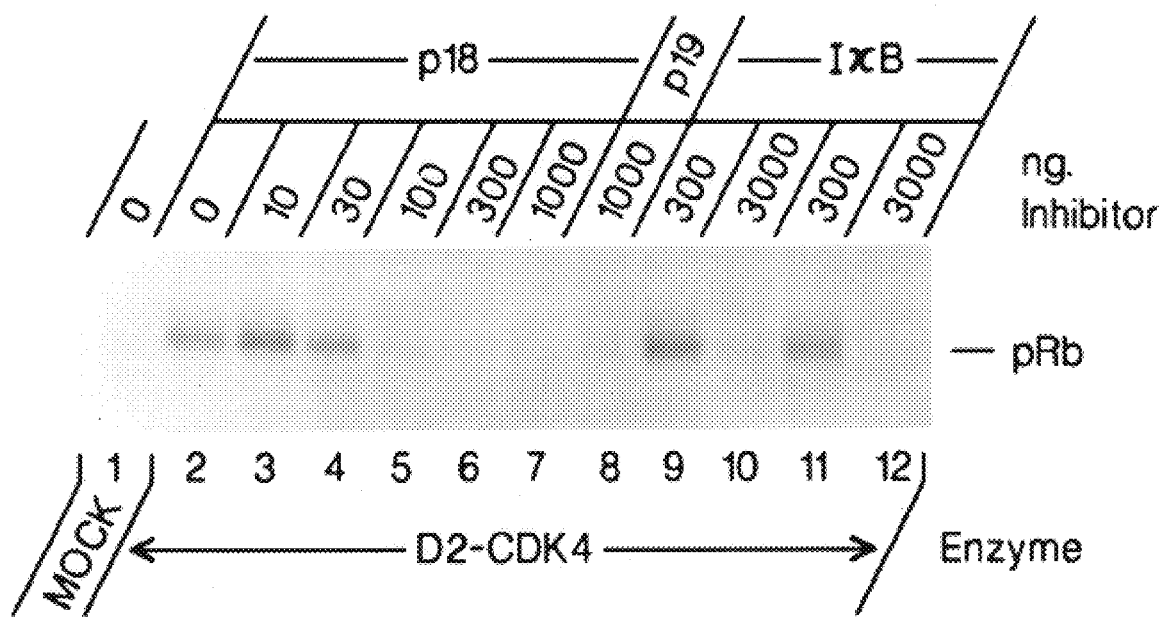
Figure 3D:
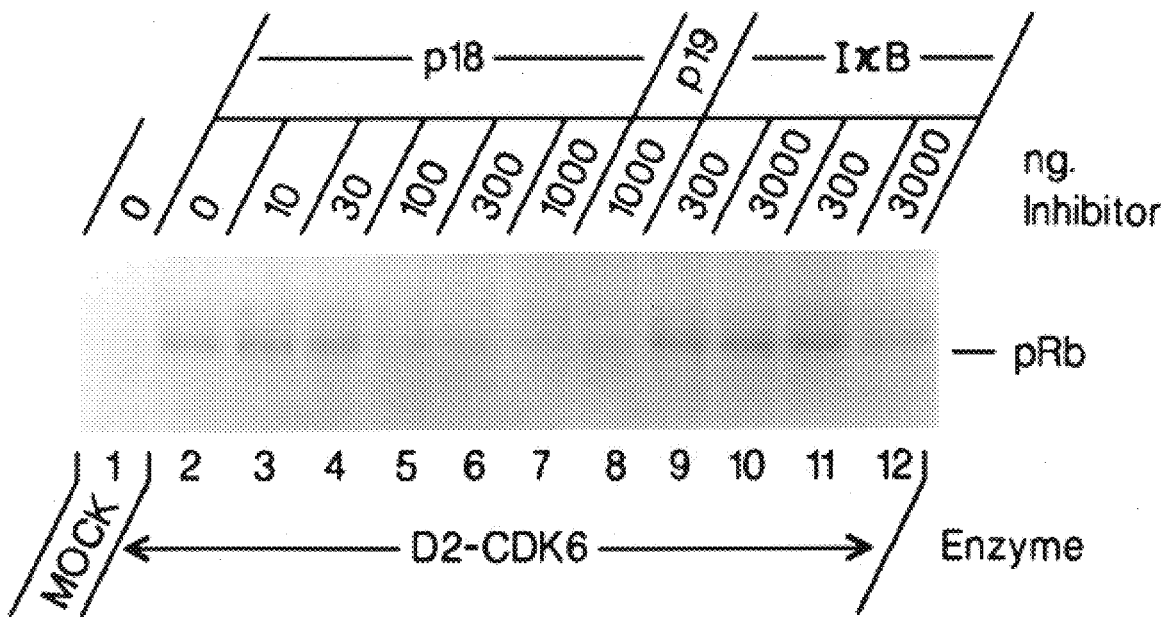

As reported previously (Matsuoka et al., Mol. Cell. Biol. 14:7265–7275 (1994)), several cdk translation products were produced from each template, with major radiolabeled species in the 34 kDa range being obtained with the cdc2, cdk2, cdk4, and cdk5 cDNAs (FIG. 2, Panel A, lanes 1, 2, 4, and 5). The predominant CDK6 species was about 38 kDa (lane 6) as predicted from its nucleotide sequence (Bates et al., Oncogene 9:71–79 (1994); Meyerson et al., EMBO J. 11:2909–2917 (1992)), but cdk3 products were significantly larger than expected, due to improper translational termination (lane 3) (Matsuoka et al., Mol. Cell. Biol. 14:7265–7275 (1994)). None of the radiolabeled translation products bound to control glutathione-Sepharose beads (FIG. 2, Panel A, lanes 7–12), and only the CDK4 and CDK6 proteins efficiently bound to beads containing the GST-p19 fusion protein (lanes 16 and 18). In the same assay, D-type cyclins were unable to interact with GST-p19 beads (FIG. 2, Panel B). Virtually identical results were obtained using GST-p18.

CDK Inhibition Assays

To determine whether their binding could inhibit CDK4 and CDK6 activity, bacterially-produced p19 and p18 fusion proteins were mixed at different concentrations with extracts containing enzymatically active complexes of CDK4-cyclin D2 and CDK6-cyclin D2 produced in baculovirus vector-infected insect cells, and the enzymes were assayed for pRb kinase activity (Kato et al., Genes & Devel. 7:331–342 (1993)). FIG. 3 shows that addition of the GST-p19 fusion protein reduced the pRb kinase activity of the CDK4-cyclin D2 (Panel A) and CDK6-cyclin D2 (Panel B) holoenzymes (lanes 2–7) to background levels equal to those observed with extracts of cells infected with a control, wild-type baculovirus (lanes 1). GST-p19 was as potent as human p16 in inhibiting the pRb kinase activity of either CDK4-cyclin D or CDK6-cyclin D (Panels A and B, lanes 9–11). However, addition of up to 1 ug of a control GST protein had no effect on either enzyme (lanes 8).

Figure 4A:
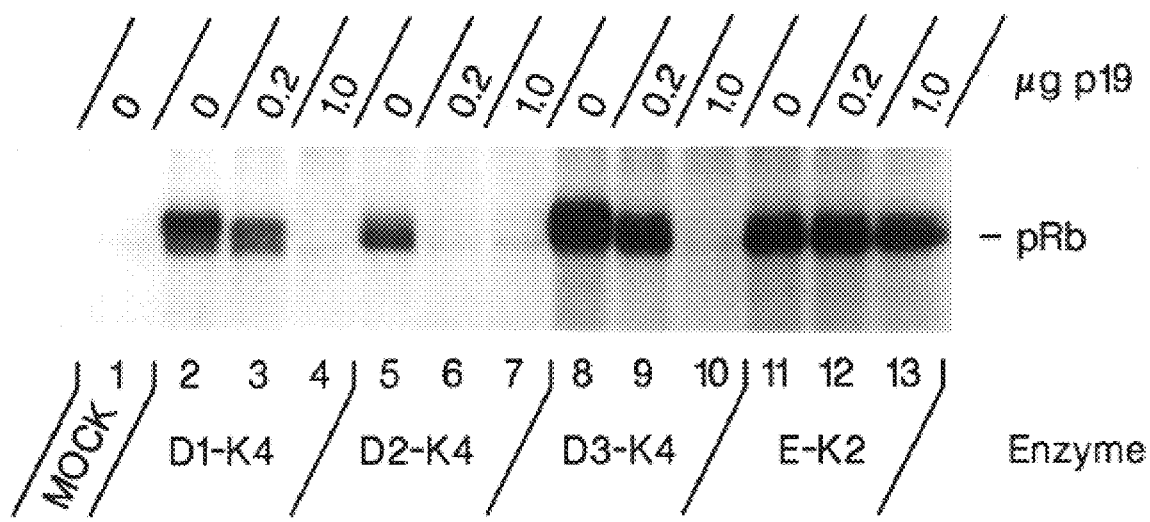
FIG. 4 shows results that demonstrate that p19 specifically inhibits cyclin D-dependent kinases. Insect extracts containing the holoenzymes indicated below each panel or those derived from cells infected with a wild-type baculovirus (mock, lane 1 in each panel) were incubated with the amounts of purified GST-p19 protein indicated at the tops of both panels. The extracts were then assayed for pRb kinase activity (Panel A) or for histone H1 kinase activity (Panel B), and the products of the reactions were resolved on denaturing gels. Exposure times were 15 hrs (Panel A) and 4 hrs (Panel B).
Figure 4B:
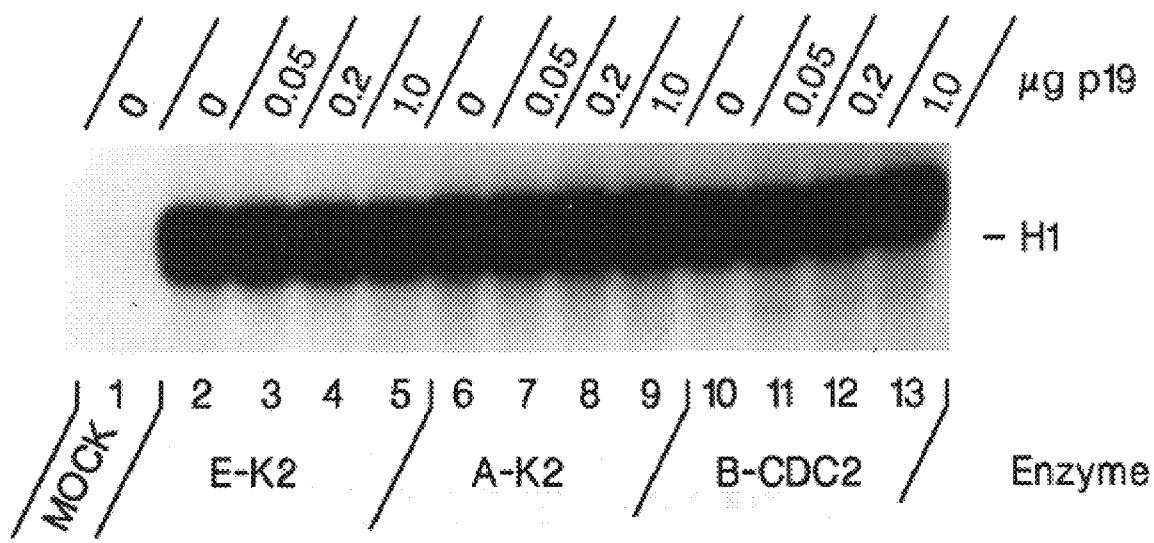

Although human p18 has been reported to have greater affinity for CDK6 than for CDK4 (Guan et al., Genes & Devel. 8:2939–2952 (1994)), the murine GST-p18 fusion protein is as potent as GST-p19 in inhibiting both kinases in vitro (FIG. 3, panels C and D, lanes 2–7). However, not all proteins containing repeated ankyrin motifs can effectively inhibit these enzymes. Mouse IκB (MAD3), for example, (FIG. 3, Panels C and D, lanes 9 and 10) or a subdomain of the protein containing only the ankyrin repeats (lanes 11 and 12) were at least 30-fold less efficient in extinguishing CDK4 and CDK6 activity than were the p19 and p18 fusion proteins. Moreover, although combinations of CDK4 with any of the D-type cyclins proved to be effective substrates for p19-mediated inhibition (FIG. 4, Panel A, lanes 1–10), p19 neither attenuated the pRb kinase activity of CDK2-cyclin E (FIG. 4, Panel A, lanes 11–13) nor affected the histone H1 kinase activity of CDK2-cyclin E, CDK2-cyclin A, or CDC2-cyclin B (FIG. 4, Panel B). Similar data were obtained with mouse p18. Therefore, both p19 and p18 interact specifically with CDK4 and CDK6 to inhibit their pRb kinase activities in complexes with D-type cyclins.

Example 4

Mouse p19 Protein does Not Displace Cyclin D from Complexes with CDK4

Spodoptera frugiperda (Sf9) cell lysates (2.5 to 5 ul, corresponding to $5 \times 10^4$ cells) containing CDKs and cyclins (Kato et al., *Genes & Devel.* 7:331–342 (1993)) were mixed with purified, soluble GST or the indicated GST fusion proteins in 10 ul of 50 mM Hepes buffer, pH 7.5, containing 10 mM $MgCl_2$, and 1 mM DTT, and incubated for 2 hours at 4° C. Kinase activity was assayed in a 25 ul reaction mixture at 30° C. for 20 minutes in the same buffer to which 2.5 mM EGTA, 10 mM β-glycerophosphate, 0.1 mM Na orthovanadate, 1 mM NaF, 20 $\mu$M ATP, 5 $\mu$Ci $\gamma$-$^{32}$P-ATP (6000 Ci/mmol; Amersham) were added. Either 0.2 ug soluble GST-pRb (Ewen et al., *Cell* 73:487–497 (1993); Kato et al., *Genes & Devel.* 7:331–342 (1993)) or 1 ug histone H1 (Boehringer Mannheim) were used as substrates. The reaction products were electrophoretically separated on denaturing gels, and phosphorylated proteins were detected by autoradiography.

For preparation of radiolabeled Sf9 lysates, cells infected with recombinant baculovirus vectors encoding cyclin D2 and CDK4 were metabolically labeled 40 hours after infection for 8 hours with 200 $\mu$Ci/ml $^{35}$S-methionine (specific activity 1000 Ci/mmol; ICN, Irvine, Calif.) and harvested as described (Kato et al., *Genes & Devel.* 7:331–342 (1993)). Portions of the lysate (7.5 ul) were diluted with 0.5 ml of IP kinase buffer containing 10 mg/ml BSA, and GST-p19 (0.3 ug) was added as indicated prior to incubation for 2 hours at 4° C. Complexes containing cyclin D2 and CDK4 were precipitated either with rabbit antiserum to intact recombinant cyclin D2 (serum $R_T$) or to the C-terminus of CDK4 (serum $R_Z$) preadsorbed to protein A-Sepharose beads (Matsushime et al., *Mol. Cell. Biol.* 14:2066–2076 (1994)). For detection of kinase activity in the immune complexes, the beads were washed twice in IP buffer and twice in kinase buffer without protease inhibitors, suspended in 25 ul kinase reaction mixture, and assayed as described above. Phosphorylated GST-pRb and metabolically labeled cyclin D2 and cdk4 were resolved by electrophoresis on 12.5% polyacrylamide gels and detected by autoradiography.

Figure 5:
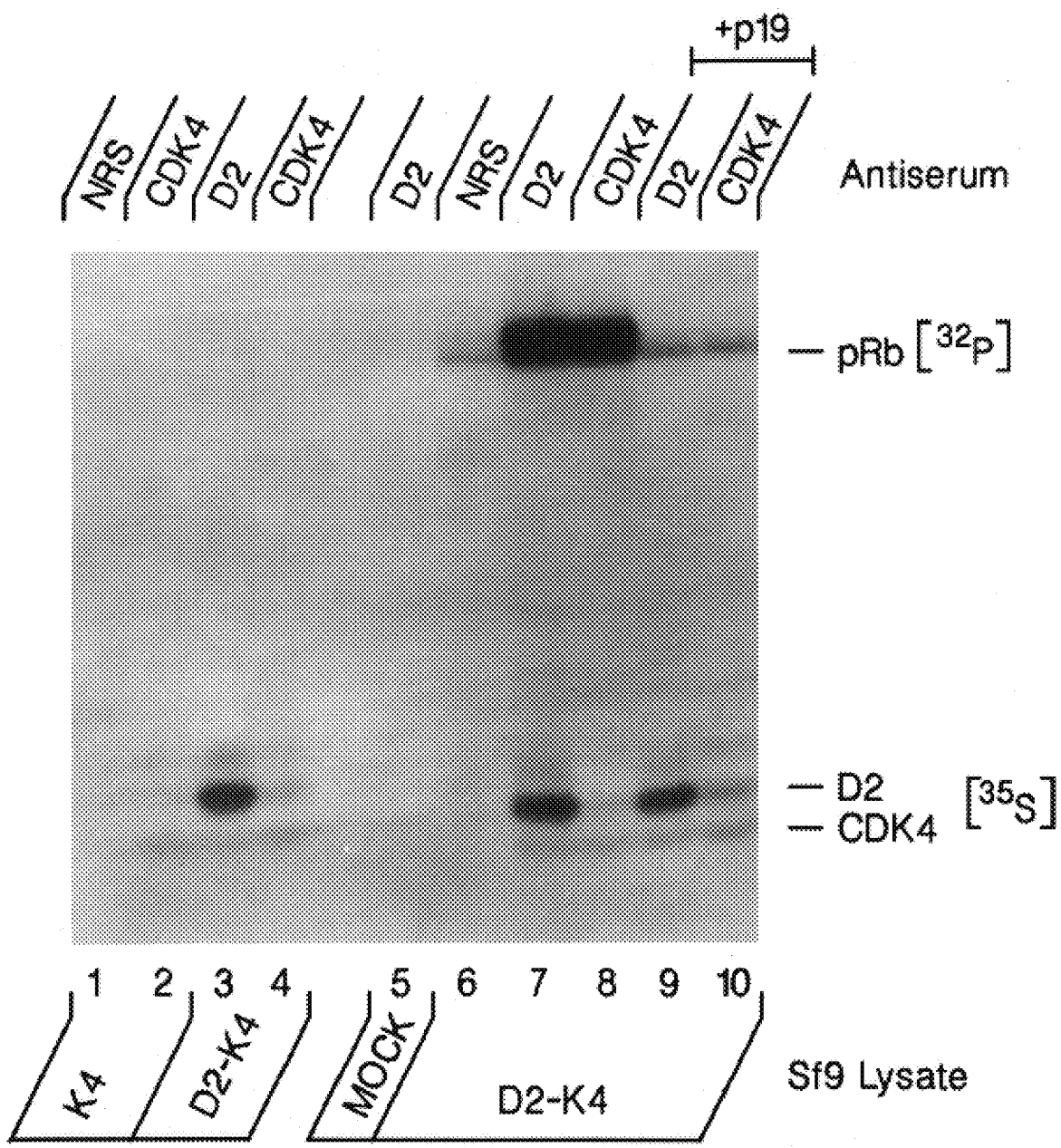
FIG. 5 shows binding of p19 to the CDK4-cyclin D2 complex and inhibition of pRb kinase activity. Insect cells infected with a baculovirus encoding CDK4 (lanes 1 and 2), co-infected with vectors encoding both CDK4 and cyclin D2 (lanes 3, 4, 6–10), or mock infected with a wild-type baculovirus (lane 5) were metabolically labeled for the final 8 hrs of infection with $^{35}$S-methionine. Lysates containing radiolabeled cdk4 and cyclin D2 were distributed into equal aliquots, and purified p19 protein (0.3 ug) was added to two of the indicated extracts (lanes 9 and 10). Extracts were precipitated with nonimmune rabbit serum (NRS) or with the indicated antisera to cyclin D2 or CDK4. The immune complexes resolved in lanes 1–4 were separated directly on denaturing gels to quantify the recovery of radiolabeled cyclin D2 and CDK4, whose electrophoretic mobilities are indicated at the right of the panel. The remaining immune complexes were used to assay precipitated pRb kinase activity, after which the reaction products were separated similarly. The position of $^{32}$P-labeled pRb is also indicated in the right margin. The autoradiographic exposure time was 15 hrs.

In cells that fail to express a functional pRb protein, p16$^{InK4a}$ has been reported to be found in a complex with CDK4 at the expense of cyclin D (Bates et al., *Oncogene* 9:1633–1640 (1994); Serrano et al., *Nature* 366:704–707 (1993)). Therefore, p16$^{InK4a}$ might compete with cyclin D for binding sites on CDK4, extinguishing its activity by displacing the positive regulator. When metabolically labeled lysates from baculovirus-infected Sf9 cells containing cyclin D2 and CDK4 were immunoprecipitated with antibodies to the individual subunits, antibodies to either subunit coprecipitated the other (FIG. 5, lanes 3 and 4). Two forms of CDK4 are produced in this system (Kato et al., *Genes & Devel.* 7:331–342 (1993)), the faster migrating form (designated at the right margin) being equivalent in mass to that detected in mammalian cells. In the experiment shown, lysates from coinfected Sf9 cells contained much more cyclin D2 (lane 3) than CDK4 (lane 4), so that all of the CDK4 coprecipitated with cyclin D under these conditions (compare the CDK4 signal in lanes 3 and 4). Consistent with these data, the washed immune complexes recovered after precipitatio n with either antiserum contained similar amounts of pRb kinase activity (lanes 7 and 8). When p19 was added to these lysates prior to immunoprecipitation, pRb kinase activity in recovered immune complexes was reduced to background levels (compare lanes 9 and 10 to lane 6), but the amount of cyclin D in the complexes was not significantly reduced (lane 10 versus lane 4). Under these conditions, similar amounts of p19 were recovered in immune complexes generated with antisera to cyclin D2 or CDK4 even though cyclin D does not interact with p19 directly. Therefore, p19 can bind to the CDK4-cyclin D holoenzyme and directly inhibit its activity without disrupting the interaction between cyclin D and CDK4.

Discussion

Both p19 and p18 share the cardinal structural and biochemical properties of previously described human Ink4 gene products, p16$^{InK4a}$ and p15$_{InK4b}$. They are composed of repeated ankyrin motifs, bind to CDK4 and CDK6, and specifically inhibit the pRb kinase activities of CDK4-cyclin D and CDK6-cyclin D complexes. InK4d-p19 can bind to binary CDK4-cyclin D complexes and inhibit their activity in vitro without displacing cyclin D. However, while antibodies to p19 coprecipitated CDK4 and CDK6 from lysates of proliferating mammalian cells, cyclin D was not detected in these complexes, suggesting that p19 might preferentially interact with the non-cyclin D-complexed forms of these CDKs in vivo. Interactions with CDK4 and CDK6 appear quite specific to the InK4 subfamily of ankyrin repeat proteins in the sense that other proteins containing these motifs, such as IκB, bind only weakly to these CDKs and inhibit their activities in vitro only if added in quantities at least 30-fold in excess of those of the InK4 polypeptides. The fact that cDNAs encoding p19 were as frequently isolated as the D-type cyclins from the yeast two hybrid screen, whereas other ankyrin repeat proteins (apart from p18) were not identified among the remaining interacting clones, provides additional confidence in the specificity of its association with CDK4. In turn, the InK4 proteins as a group fail to inhibit other CDK-cyclin complexes, including CDK2-cyclin E, CDK2-cyclin A, and CDC2-cyclin B, and they do not bind to CDC2, CDK2, CDK3, or CDK5 in vitro. This evidence supports the position that these proteins play physiologic roles as specific regulators of CDK4 and CDK6 activity in vivo.

Example 5

Figures 6A, 6B:
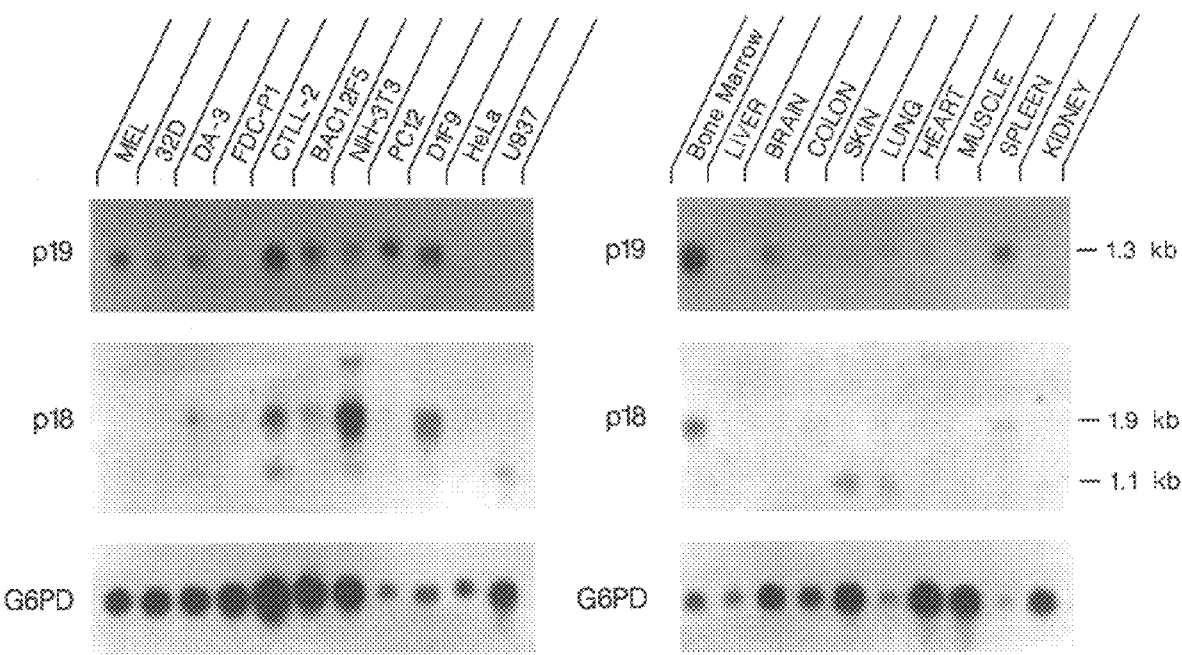
FIG. 6 shows the expression of p19 and p18 mRNAs in cell lines and mouse tissues. Total cellular RNA was extracted from the indicated cell lines (panel A) or mouse tissues (panel B), electrophoretically separated on agarose gels containing formamide (10 ug/lane), transferred to nitrocellulose, and hybridized with the indicated $^{32}$P-labeled cDNA probes. Autoradiographic exposure times were 5 days (p19), 12 days (p18) and 2 days (G6PD).

Expression of p18 and p19 in Mice
InK4c-p18 and InK4d-p19 are Expressed in Many Tissues in Mice A single class of p19 mRNA transcripts 1.3 kb in length was detected in a variety of mouse cell lines, as well as in many mouse tissues, when p19 cDNA was used as a probe in hybridization studies (FIG. 6). The p19 cDNA was originally isolated from thymic lymphoma cells, and relatively high levels of p19 mRNA were detected in hematopoietic organs, such as bone marrow and spleen (FIG. 6, Panel B), as well as in blood cell lines including MEL (erythroid), 32D, DA-3 and FDC-P1 (immature myeloid), BAC1.2F5 (macrophages), and CTLL-2 (T cells) (FIG. 6, Panel A). As reported for its human cognate (Guan et al., *Genes & Devel.* 8:2939–2952 (1994)), the patterns of expression of p18 were more complex. First, at least three forms of mRNA were observed, and these were differentially expressed in various tissues. Note, for example, that skin and lung primarily express a p18 transcript of 1.1 kb, whereas the predominant mRNA in bone marrow and spleen is considerably larger (1.9 kb). Unlike the human InK4a and InK4b genes, which are expressed at very low levels in many tissues and are deleted in a high percentage of established cell lines, both p19 and p18 expression can be readily detected.

Expression of p19 During the Macrophage Cell Cycle

Murine BAC1.2F5 macrophages were cultured in Dulbecco's modified Eagle's medium (DMEM) supplemented with 15% fetal bovine serum, 2 mM glutamine, 100 U/ml penicillin, 100 ug/ml streptomycin, and 25% L cell-conditioned medium as a source of colony-stimulating factor-1 (CSF-1) (Stanley, *Methods Enzymol.* 116:564–587 (1986)). The cells were arrested in early G1 phase by CSF-1 starvation for 18 hours, after which they were restimulated with CSF-1 to reenter the cycle synchronously (Matsushime et al., *Cell* 65:701–713 (1991); Tushinski and Stanley, *J. Cell. Physiol.* 122:221–228 (1985)). Cells ($2\times10^7$ per data point) were harvested at indicated intervals thereafter, and the DNA content of representative aliquots was measured by flow cytometric analysis of propidium iodide stained nuclei (Matsushime et al., *Cell* 65:701–713 (1991)). For preparation of RNA, washed cells were scraped into 4.2 M guanidine thiocyanate, 0.1 M Na acetate (pH 5), 5 mM EDTA and layered over 2M $CsCl_2$, 0.1 M Na acetate, 5 mM EDTA in a Beckman SW41 centrifuge tube. Following centrifugation at 33,000 rpm overnight, the pelleted RNA was suspended in 10 mM Tris HCl, pH 7.5, 10 mM EDTA, and 0.5% SDS, extracted twice with phenol and twice with chloroform, and precipitated with 2.5 volumes of ethanol at $-20°$ C. RNA was separated electrophoretically in 1% agarose, blotted to nitrocellulose, and hybridized with the indicated cDNA probes at 42° C. for 20 hours in 5× SSPE buffer (1× SSPE is 0.15 M NaCl, 10 mM $NaH_2PO_4$, 1 mM EDTA) containing 50% formamide (Dean et al., *Oncogene Res.* 1:279–296 (1987)). Filters were washed with 2× SSC containing 0.1% SDS first at 42° C. and then at 65° C.

Asynchronously proliferating macrophages or synchronized cells prepared as described above ($1\times10^6$ cells per time point) were metabolically labeled for 1 hr. with 200 $\mu$Ci/ml $^{35}$S-methionine, and p19 immunoprecipitated from the cell lysates was resolved on denaturing polyacrylamide gels and detected by autoradiography using previously described methods (Matsushime et al., *Cell* 65:701–713 (1991)). In some experiments, immunoprecipitated p19 resolved on gels was transferred to nitrocellulose and immunoblotted with antiserum to CDK4; sites of antibody binding were detected using $^{125}$I-labeled S. aureus protein A (Downing et al., *Mol. Cell. Biol.* 8:1795–1799 (1988)).

Because both p19 and p18 are expressed in bone marrow-derived macrophages, we were able to study their regulation throughout the cell cycle. BAC1.2F5 macrophages arrest in early G1 phase when deprived of CSF-1 for 18–22 hrs and can be induced to reenter the cell cycle synchronously by readdition of the growth factor (Matsushime et al., *Cell* 65:701–713 (1991); Tushinski and Stanley, *J. Cell. Physiol.* 122:221–228 (1985)). FIG. 7 shows that p19 mRNA could be detected in starved, quiescent cells (time 0) but decreased in abundance as cells entered G1 phase. However, as cells approached the G1/S transition (about 10 hrs.), p19 mRNA synthesis was abruptly reinitiated and increased as the cells progressed through the remainder of the cycle. Maximal cell division occurred at 18–20 hrs. Although the cells rapidly lost synchrony in the second cycle, and the second G1 phase was shorter than the first (Matsushime et al., *Cell* 65:701–713 (1991)), p19 levels again fell during G1 (about 22–28 hrs.) but increased in S phase (32–36 hrs). The relative abundance of p19 mRNA, determined by scanning the Northern blots with a phosphoimager, is summarized graphically at the bottom of FIG. 7. Virtually identical results were obtained using NIH-3T3 cells induced to reenter the cell cycle from quiescence by serum readdition.

During reentry into the cell cycle, p18 mRNA was induced with kinetics similar to that of p19. However, CSF-1-starved macrophages expressed the 1.1 kb p18 mRNA species, whereas only the 1.9 kb form was induced at the G1/S transition and remained elevated until cells reentered another cycle. The kinetics of induction of the p19 and p18 mRNAs in the first cycle were similar to that of cyclin A, which is also induced near the G1/S boundary (Pines and Hunter, *Nature* 346:760–763 (1990)), but are readily distinguished from those of cyclin D1 mRNAs, which are induced early in G1 phase and oscillate only modestly as cells continue to proliferate (Matsushime et al., *Cell* 65:701–713 (1991)). The expression of a "housekeeping" gene, glucose 6-phosphate dehydrogenase (G6PD), showed minimal oscillation throughout the cycle, although its mRNA was somewhat less abundant in growth factor deprived cells.

Expression of $p18^{InK4c}$ and $p19^{InK4d}$ mRNAs can be readily detected in mouse tissues and cell lines where they appear to oscillate throughout the cell cycle. Several forms of p18 mRNA were observed which were differentially regulated in various tissues, whereas the pattern of p19 expression was less complex, with only a single 1.3 kb mRNA observed. In synchronized macrophages, the abundance of p19 mRNA temporally correlated with the rates of p19 protein synthesis observed throughout the cell cycle, with the levels of mRNA and protein reaching a nadir in G1 phase, abruptly increasing as cells entered S phase, and declining again as cells completed mitosis and reentered G1.

Example 6

Antibodies to p18 and p19

Polyclonal Antibodies

A polyclonal antibody composition is produced by immunizing an animal with purified p18 or p19 protein produced, for example, by expression of nucleic acid sequences encoding p18 or p19 in an appropriate host/vector system (see Example 2), and preparing serum from the immunized animal (Harlow and Lane, *Antibodies: A Laboratory Manual*, Cold Spring Harbor Laboratory, Cold Spring Harbor (1989), pages 53–137).

Monospecific Antibodies

A synthetic peptide corresponding to the eight C-terminal amino acids of mouse p19 was conjugated to keyhole limpet hemocyanin and used to immunize rabbits (Downing et al., *Mol. Cell. Biol.* 11:2489–2495 (1991)). The antiserum precipitated radiolabeled mouse p19 produced by translation in vitro, but did not crossreact with mouse p18 or human p16 produced in parallel.

Figure 8D:
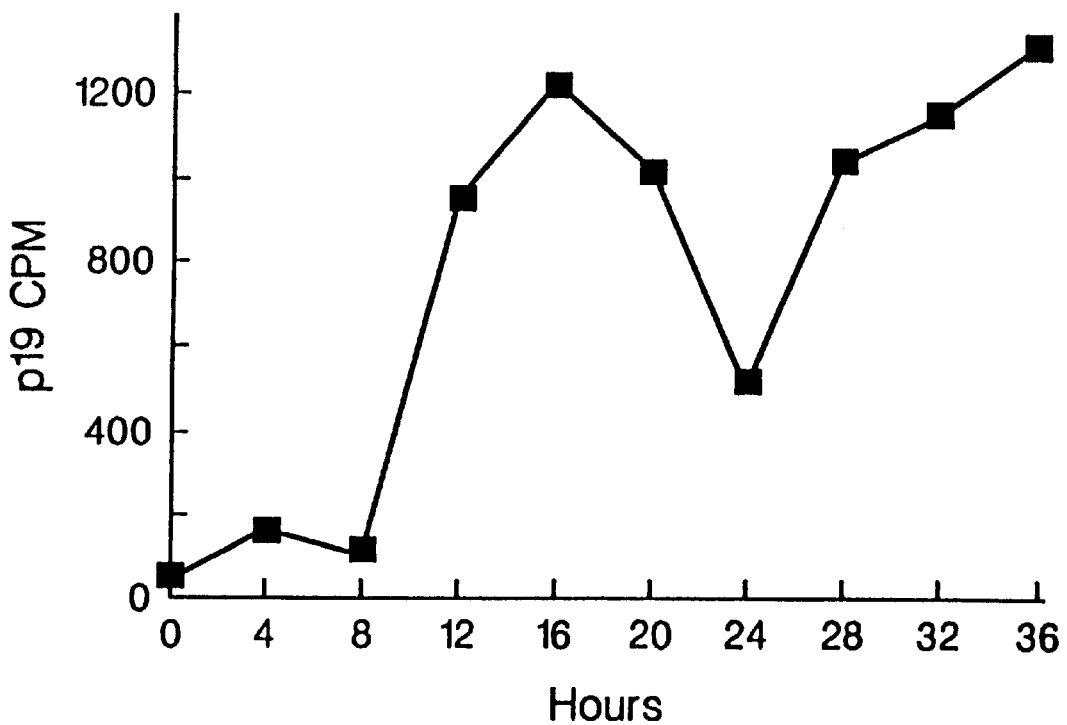
FIG. 8 shows p19 protein expression. In Panel A, NIH-3T3 fibroblasts (lanes 1–3) and BAC1.2F5 macrophages (lanes 4 and 5) were metabolically labeled with $^{35}$S-methionine for 1 hour, cell lysates immunoprecipitated with antiserum directed to a synthetic peptide based on the p19 C-terminus and resolved on denaturing gels. No p19 was detected after competition with the cognate peptide (lanes 2 and 5), whereas an unrelated peptide had no competitive effect (lane 3). In Panel B, lysates of BAC1.2F5 macrophages were immunoprecipitated with nonimmune rabbit serum (NRS, lane 1), antiserum to the p19 C-terminus (lane 2), and antiserum to CDK4 (lane 3), separated on denaturing gels, transferred to nitrocellulose and immunoblotted with antiserum to CDK4. In Panel C, CSF-1 starved macrophages stimulated to synchronously reenter cycle (as in FIG. 7) were pulse labeled for 1 hour at the indicated times in hours (top) with $^{35}$S-methionine, and precipitates prepared with antiserum to the p19 C-terminus were separated on denaturing gels. Panel D shows the rate of synthesis of p19 throughout the cell cycle, as determined by phosphoimaging analysis of the data shown in Panel C. Exposure times were 5, 2, and 4 days for Panels A, B, and C, respectively.
Figure 9A:
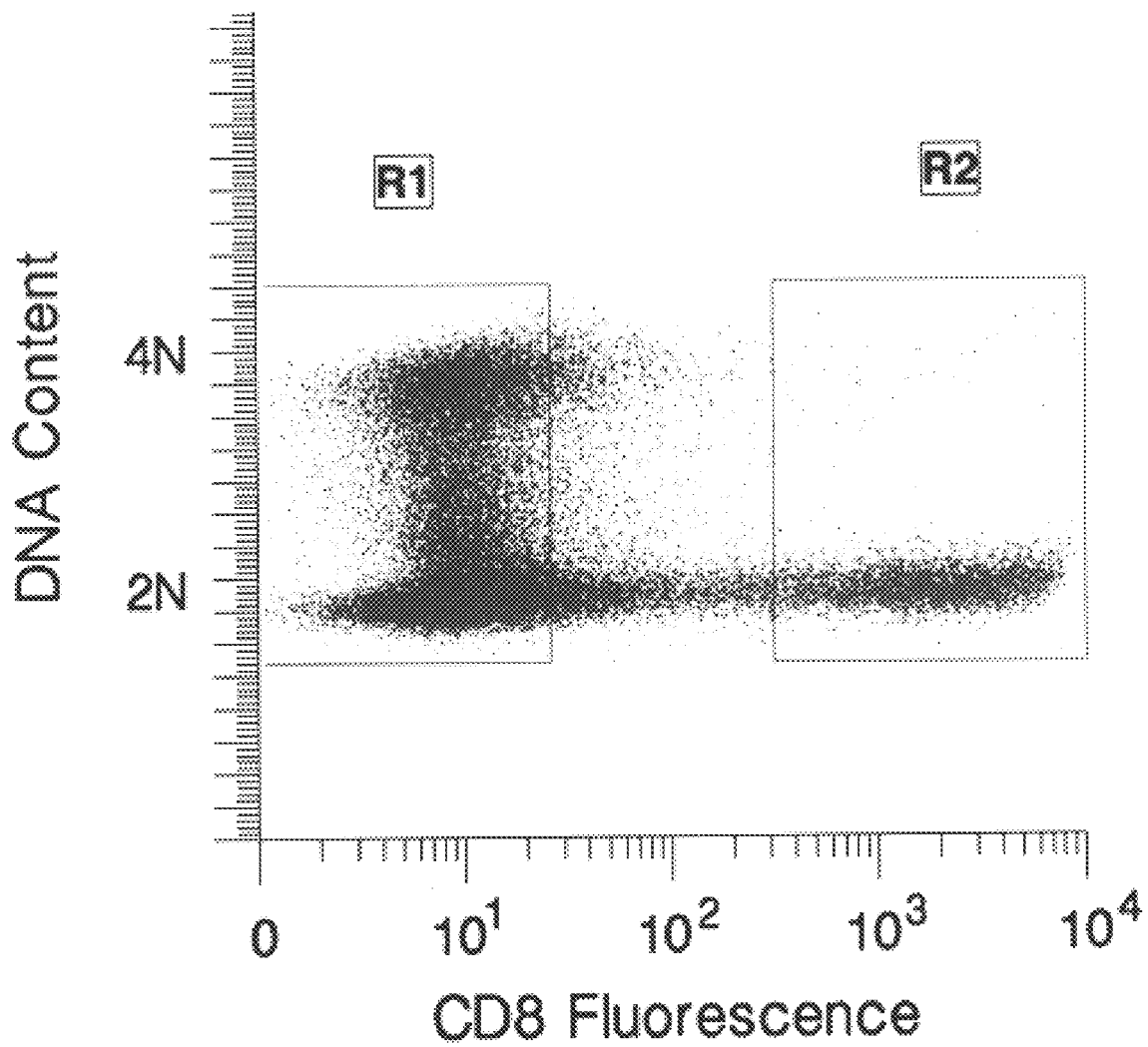
FIG. 9 displays results from experiments that demonstrate that vector-mediated p19 expression induces G1 phase arrest. NIH-3T3 cells transfected with a vector encoding both p19 and CD8 were analyzed 48 hours later for CD8 fluorescence and DNA content (Panel A). Cells yielding a fluorescence profile equivalent to those obtained with CD8-negative fibroblasts (box R1) and those expressing the highest level of CD8 antigen (box R2) were separately gated and analyzed for DNA content (Panel B). In panel C, immunoprecipitates from NIH-3T3 fibroblasts infected with a control CD8 vector or a vector containing p19 (as indicated at the bottom of the panel) were analyzed 48 hours later for pRb kinase activity. Immune complexes were obtained with normal rabbit serum (NRS), monoclonal antibody (D1-72-13G) to cyclin D1 (D1), antiserum to the cdk4 C-terminus (CDK4), or antiserum to CDK4 plus competing cognate peptide (CDK4+P), as indicated at the top of the panel. Precipitates were prepared from cells engineered to overexpress cyclin D1 (3T3-D1, lanes 1–8) or from parental NIH-3T3 cells (3T3, lanes 9–11). To obtain matched autoradiographic signals, lysates were prepared from ⅛th the number 3T3-D1 cells versus parental cells. The exposure time was 8 hrs.
Figure 9B:
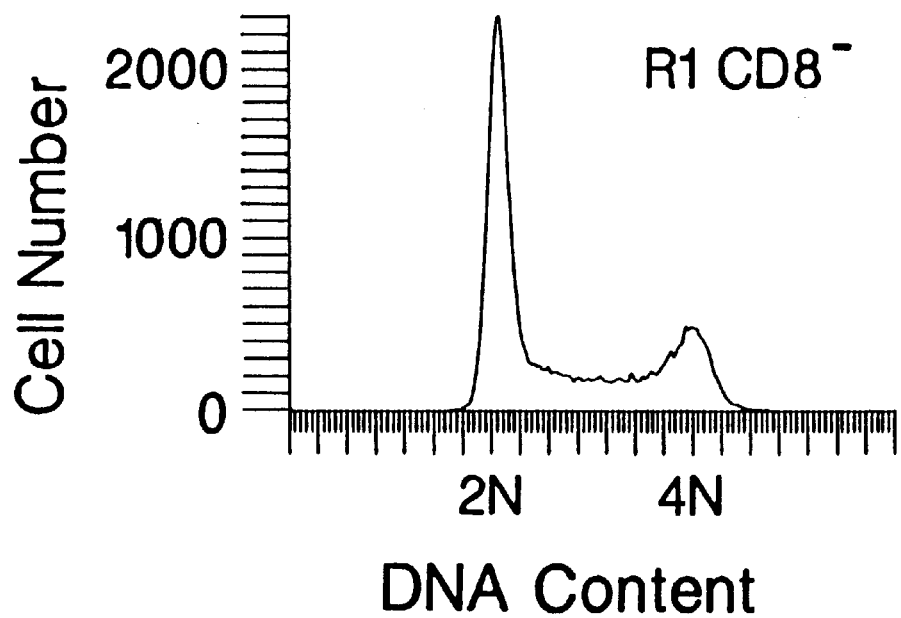
Figure 9C:
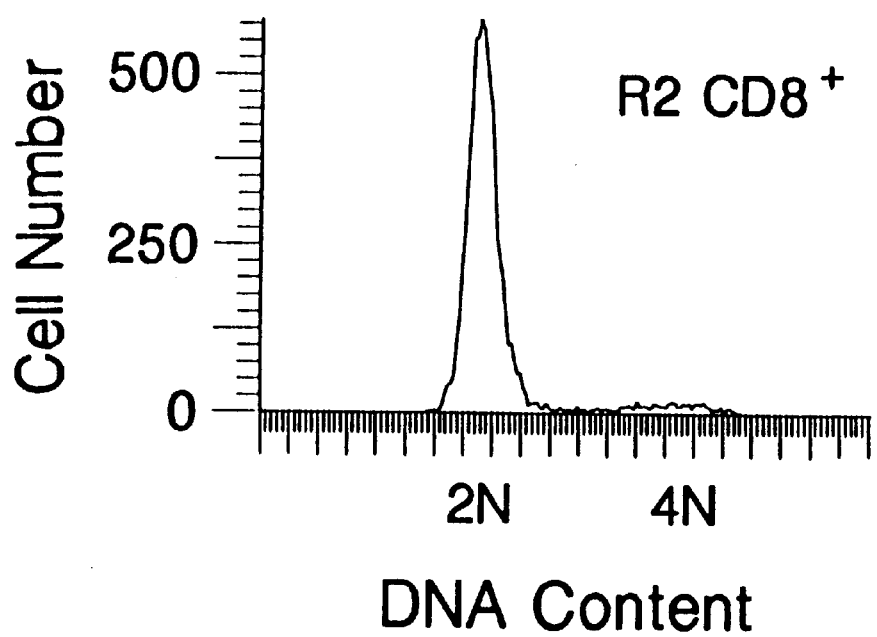
Figure 9D:
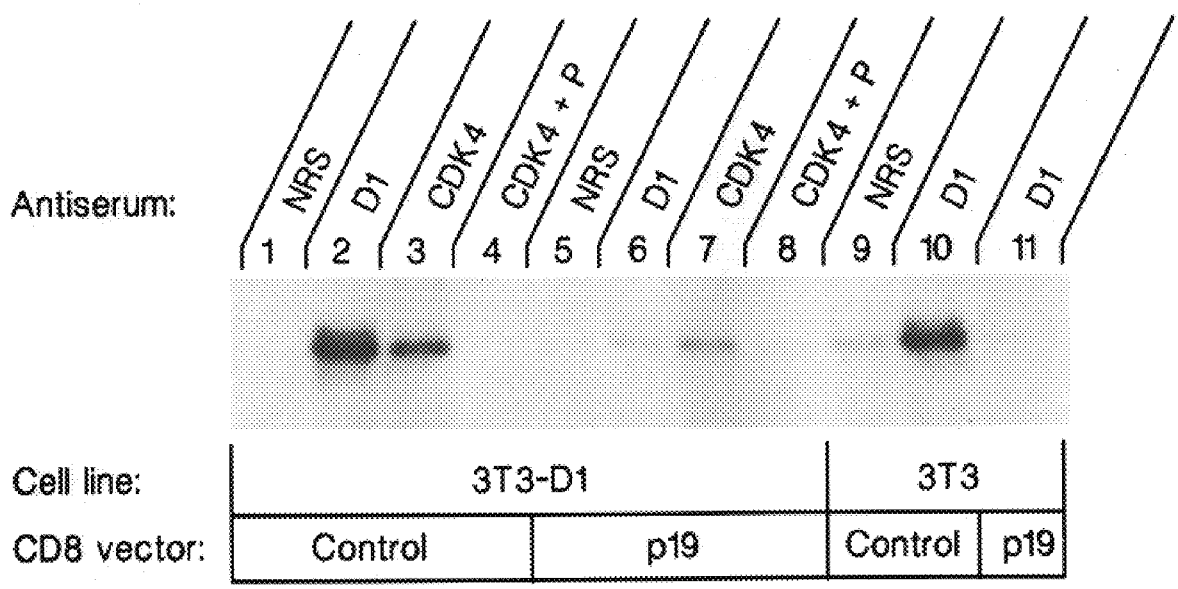

An anti-peptide (monospecific) serum directed to the p19 carboxyl terminus was used to immunoprecipitate the metabolically labeled protein from proliferating mouse cells (FIG. 8, Panel A, lanes 1 and 4). The immunoprecipitated 19 kDa protein could be competed with the cognate peptide (lanes 2 and 5) but not with an unrelated peptide based on the CDK2 C-terminus (lane 3). InK4d-p19 immunoprecipitates also contained CDK4 (FIG. 8, Panel B, lane 2) but did not contain detectable levels of cyclin D1. Similar results were obtained with cell lines expressing CDK6. Thus, although p19 can bind to CDK4-cyclin D complexes in vitro (FIG. 5), like other InK4 proteins, it may preferentially interact with unbound CDK4 and CDK6 in vivo. Consistent with the kinetics of p19 mRNA expression in synchronized macrophages (FIG. 7), synthesis of p19 protein was first detected near the G1/S boundary, decreased as cells divided and re-entered a second G1 phase, and increased again during the following S phase (FIG. 8, Panel C). Hence, p19 mRNA and protein synthesis are periodic with relative nadirs during G1 phase.

Monoclonal Antibodies

For preparation of monoclonal antibodies, spleen cells from the animals immunized with p18 or p19 proteins, or with synthetic p18 or p19 oligopeptides are removed, fused with myeloma cells, such as SP2/0-AG14 myeloma cells, and allowed to become monoclonal antibody producing hybridoma cells (Harlow and Lane, *Antibodies: A Laboratory Manual*, Cold Spring Harbor Laboratory, Cold Spring Harbor (1989), pages 139–281). Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired p18- or p19-specific antibodies are cloned and the class and subclass is determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)). Monoclonal antibodies are purified using methods known in the art (Harlow and Lane, *Antibodies: A Laboratory Manual*, Cold Spring Harbor Laboratory, Cold Spring Harbor (1989), pages 283–318; Grandics, *Biotechnology Laboratory*, May issue, pages 58–62 (1994); Grandics, *Biotechnology Laboratory*, June issue, pages 12–14 (1994); Grandics, *Biotechnology Laboratory*, July issue, pages 16–18 (1994)).

Example 7

InK4d-p19-Mediated Arrest of G1

Enforced Expression of p19 in Mammalian Fibroblasts

The BamHI-EcoRI fragment encoding p19 and a HindIII-BamHI fragment containing the entire coding sequence of mouse CD8 (Zamoyska et al., *Cell* 43:153–163 (1985)) were both subcloned into the pSRα-MSV-TK retrovirus vector (Muller et al., *Mol. Cell. Biol.* 11:1785–1792 (1994)) provided by Dr. Charles Sawyers (UCLA Medical Center, Los Angeles, Calif.). In this construct, p19 is expressed under the control of viral LTR sequences, whereas CD8 expression is controlled by an internal thymidine kinase promoter. The plasmid was transfected into NIH-3T3 cells (Chen and Okayama, *Mol. Cell. Biol.* 7:2745–2752 (1987)), and 48 hours later, transfected cells were immunostained with anti-CD8, counterstained with propidium iodide, and analyzed by flow cytometry to determine the DNA content of gated CD8-positive and CD8-negative cells (Look et al., *J. Clin. Invest.* 73:1617–1628 (1984)).

For virus production and infection, the same plasmid was cotransfected into 293T cells (Pear et al., *Proc. Natl. Acad. Sci. (USA)* 90:8392–8396 (1993)) together with a plasmid encoding an ecotropic helper virus containing a defective virion packaging (ψ2) sequence (Muller et al., *Mol. Cell. Biol.* 11:1785–1792 (1994)). Culture supernatants containing retroviruses harvested 48–72 hours after transfection were used to infect proliferating NIH-3T3 fibroblasts. Infected cells were analyzed 48 hours later by flow cytometry as described above or were lysed in IP kinase buffer, and CDK4-cyclin D complexes were immunoprecipitated and assayed for Rb kinase activity (Matsushime et al., *Mol. Cell. Biol.* 14:2066–2076 (1994)).

InK4d-p19 Arrests G1 Progression

Expression of p19 is extinguished during G1 phase as CDK4-cyclin D or CDK6-cyclin D executes its critical functions. To determine whether constitutive expression of p19 would specifically arrest the cell cycle in G1 phase, p19 cDNA was inserted into a retroviral expression vector that also encodes the CD8 cell surface antigen. Asynchronously proliferating mouse NIH-3T3 fibroblasts were transfected with CD8 vectors lacking or containing p19 cDNA, and 48 hours later, the transfected cells were analyzed for both CD8 expression and DNA content by two color flow cytometry. Cells transfected with the vector encoding both CD8 and p19 yielded a proportion of untransfected recipients that exhibited background CD8 fluorescence and were distributed throughout the cell cycle (delimited by box R1 in FIG. 9, Panels A and B). By contrast, 85% of those cells that expressed high levels of CD8 antigen (gated in box R2) exhibited a 2N DNA content characteristic of those in G1 phase (FIG. 9, Panels A and B). Cells transfected with the control CD8 expression vector, whether CD8-positive or not, were distributed throughout the cell cycle in a manner indistinguishable from those of untransfected cells (G1= 54.6%±4.9; S=36.5%±3.1; and remainder G2/M) indicating that transfection per se was not toxic and did not induce cell cycle arrest. In five independent experiments, transfection with the CD8 vector coexpressing p19 increased the proportion of cells in G1 by 22%±12, whereas transfection with the control CD8 vector had no effect.

By cotransfecting the p19 vector plasmid together with a second plasmid providing retroviral helper functions into SV40 T antigen-positive 293T cells, virions were produced that were capable of efficiently infecting NIH-3T3 cells. Within 48 hours of infection, the majority of such cells became CD8-positive and exhibited a concomitant (18%±3%) increase in their G1 fraction as compared to cells infected with the control CD8 vector lacking p19 cDNA. Cells harvested upon completion of the experiment, unlike proliferating NIH-3T3 cells, lacked detectable cyclin D-dependent kinase activity (FIG. 9, Panel B, lanes 9–11). Even using cells engineered to overexpress cyclin D (Quelle et al., *Genes & Devel.* 7:1559–1571 (1993)), where the levels of cyclin D-dependent kinase are elevated 5–10 fold (Matsushime et al., *Mol. Cell. Biol.* 14:2066–2076 (1994)), infection with the p19 vector almost completely inhibited cyclin D-dependent kinase (or cdk4 kinase) activity (FIG. 9, Panel B, lanes 1–8). Therefore, G1 phase arrest induced by constitutive p19 expression is accompanied by inhibition of cyclin D-dependent kinase activity in vivo.

Introduction of a vector encoding p19 into NIH-3T3 fibroblasts led to G1 phase arrest, indicating that p19 synthesis during the G1 interval, but apparently not during later phases, can halt cell cycle progression. Cyclin D1-dependent (CDK4) kinase activity was markedly reduced in cells engineered to ectopically express p19, including those that were engineered to overexpress cyclin D1, demonstrating that p19 has potent CDK4 inhibitory activity in vivo. The simplest interpretation is that p19-mediated inhibition of CDK4 kinase activity renders such cells unable to transit a cyclin D-dependent G1 phase checkpoint.

Example 8

Cloning of Human p19 cDNA Sequences

To obtain a human cDNA encoding InK4d-p19, a ~300-bp SpeI-HincII fragment of the murine p19 cDNA was isolated, labeled with α³²P-dCTP (DuPont-NEN, Boston, Mass.) by use of random hexamers and the Klenow fragment of DNA polymerase (Boehringer Mannheim, Indianapolis, Ind.) (Feinberg and Vogelstein, *Anal. Biochem.* 132:6–13 (1983)), and was used to screen a lambda gt-10 CDNA library prepared from human bone marrow (Clontech Laboratories, Palo Alto, Calif.). This library was chosen based on the preliminary observation that the message of the Ink4d gene was highly expressed in hematopoietic tissues as demonstrated in Northern blots of tissues from mouse organs (Example 5). Colony lifts on nylon membrane filters (Amersham, Arlington Heights, Ill.) were hybridized with 1×10⁶ cpm of probe per ml in 3×SSC, 1×Denhardt, 40 ug/ml denatured salmon testis DNA and 35% formamide at 42° C. overnight. Filters were washed in 1×SSC, 0.1% SDS at 42° C. followed by autoradiography. The conditions for hybridization and washing were predetermined by Southern blot analysis using the mouse probe on fractionated human genomic DNA. Candidate clones were plaque purified, and cDNA inserts were subcloned into pBluescript (Stratagene, La Jolla, Calif.) plasmid vector and subjected to restriction enzyme mapping by standard methods (Sambrook et al., *Molecular Cloning: A Laboratory Manual*, 2nd Ed., Cold Spring Harbor Laboratory Press, Cold Spring Harbor, N.Y. (1989), pages 5.28–5.32) and to sequencing analysis by the dideoxynucleotide chain-termination method (Sanger et al., *Proc. Natl. Acad. Sci. (USA)* 74:5463–5467 (1977)) modified for use with double-stranded DNA templates (United Stated Biochemical, Cleveland, Ohio.).

To obtain human cDNA for InK4d-p19, one million plaques from a human bone marrow CDNA library were screened. Three independent human p19 cDNA clones were isolated, including a 1.4-kb cDNA clone (clone 19-4) and two smaller, presumed partial cDNA clones (clones 19-1 and 19-3). Given the size of mRNA transcripts detected in Northern blot analysis (~1.4-kb; see Example 10), it is likely that clone 19-4 contains a full-length cDNA. Sequence analysis of the three clones revealed an open reading frame of 498 bp that encodes a 166 amino acid polypeptide having a predicted molecular weight of 17.7 kilodaltons (kDa) (FIG. 10A). As described in Example 1, the mouse Ink4d gene product comprises four repeats of an ankyrin motif, and belongs to the InK4 gene family. The sequence of the human InK4d-p19 polypeptide is 86% identical at the amino acid level to that of the murine InK4d-p19 clone and 44% identical to human InK4c-p18, its most closely related InK family member (FIG. 10B).

Example 9

Analysis and Cloning of Human p19 Genomic DNA Sequences

Southern Blot Analysis

High molecular weight genomic DNA was isolated by standard techniques from Epstein-Barr virus (EBV) transformed lymphoblastoid cell lines established from peripheral blood of healthy volunteers. The isolated DNA was digested with restriction endonuclease EcoRI, BglII or HindIII, size fractionated by electrophoresis through a 0.9% agarose gel, transferred to a nylon membrane (HyBond-N, Amersham), and hybridized with a ³²P-labeled 1.4-kb human InK4d-p19 cDNA (clone 19-4). After high stringency washing in 0.1×SSC and 0.1% SDS at 65° C., the filters were exposed to XAR-5 film (Kodak, Rochester, N.Y.) with intensifying screens at –70° C. Results of this analysis demonstrate a single InK4d-p19 hybridizing restriction fragment following digestion with EcoRI (~23 kb), BglII (~22 kb), and HindIII (~9 kb), consistent with InK4d-p19 being encoded by a single copy gene. The estimated size of the genomic locus for the human Ink4d gene is <20 kb.

Isolation of a P1 Phage Clone for the Human p19 Locus

A human genomic P1-phage library (Genome Systems, St. Louis, Mo.) was screened by the polymerase chain reaction (PCR) using a pair of oligonucleotide primers, the sequences of which are derived from the cloned human p19 cDNA nucleotide sequence:

AGCAAGGTGCCAGCCCCAATGTCCA (5' primer) (SEQ ID NO:14); and

GCGTCCCTGCGATGGAGATCAGATT (3' primer) (SEQ ID NO:15).

The primers were designed to amplify a 225 bp fragment within putative exon 2 of the gene, as predicted by comparing the p19 sequence with the genomic organization of InK4a-p16 genes (Serrano et al., *Nature* 366:704–707 (1993); Kamb et al., *Science* 264:436–440 (1994); Noburi et al., *Nature* 368:753–756 (1994)). The predicted genomic organization was verified by amplification reactions that yielded a product of expected size from human genomic DNA. PCR amplification conditions were optimized prior to screening the library.

Three partially overlapping P1-phage clones (#3857, #3858, #3859) yielded the expected sized InK4d-p19 PCR amplification fragment. Southern blot analysis of DNA isolated from these clones revealed identical sized InK4d-p19 hybridizing EcoRI, BglII, and HindIII restriction fragments compared to those seen with total human genomic DNA (i.e., ~23 kb, ~22 kb and ~9 kb, respectively), demonstrating that the P1-phage clones contained the entire InK4d-p19 genomic locus. Clone #3857 was used as a probe for fluorescence in situ hybridization analysis (see Example 11).

Example 10

Expression of p19 in Human Cells

Cell Culture, Cell Cycle Fractionation and Induction of Apoptosis

HeLa and CEM-C7 (a human immature T-cell line) cells were cultured under standard conditions (Zieve et al., *Exp. Cell Res.* 126:397–405 (1980); Lahti et al., *Mol. Cell Biol.* 15:1–111 (1995)). For cell cycle fractionation, HeLa cells were arrested at mitosis as described by Zieve et al. by sequential treatment with 5 mM thymidine and 0.4 ug/ml of nocadazole for 8 hours and 12 hours, respectively. Mitotic cells were then harvested by mechanical release from the culture dish. After releasing from nocadazole block by washing with phosphate buffer and putting back the cells into complete culture media, the cells entering cell cycle were sequentially harvested for RNA isolation at every 2 hours for 24 hours, and DNA content of aliquots at each time point was measured by flow cytometric analysis of propidium iodide stained nuclei (see Example 5). Apoptosis was induced by treated CEM-C7 cells with a FAS monoclonal antibody (Upstate Biotechnology, Inc.) at 100 ng/ml, and cells were collected at various time points for RNA and DNA analysis. Programmed cell death was confirmed by morphological analysis of nuclei and DNA analysis by fractionation in a 0.9% agarose gel followed by ethidium bromide staining (Lahti et al., *Mol. Cell Biol.* 15:1–11 (1995)).

Northern Blot Analysis

Total cellular RNA and poly(A)+ RNA were isolated from murine and human cell lines by standard methods (Sambrook et al., *Molecular Cloning: A Laboratory Manual*, 2nd Ed., Cold Spring Harbor Laboratory Press, Cold Spring Harbor, N.Y. (1989), pages 7.39–7.52). Approximately 20 ug of total cellular RNA or 4 ug of poly(A)+ RNA were fractionated on 1.0% agarose-formaldehyde gels by electrophoresis and blotted to nitrocellulose or nylon membrane filters. Northern blots containing poly(A)+ RNA from various human adult or fetal tissues were purchased (Clontech). Filters were hybridized with a cDNA probe for human InK4d-p19 or chicken or human cDNAs for β-actin. Final wash of the filters was in 0.1×SSC, 0.1% SDS at 60° C.

Figure 11:
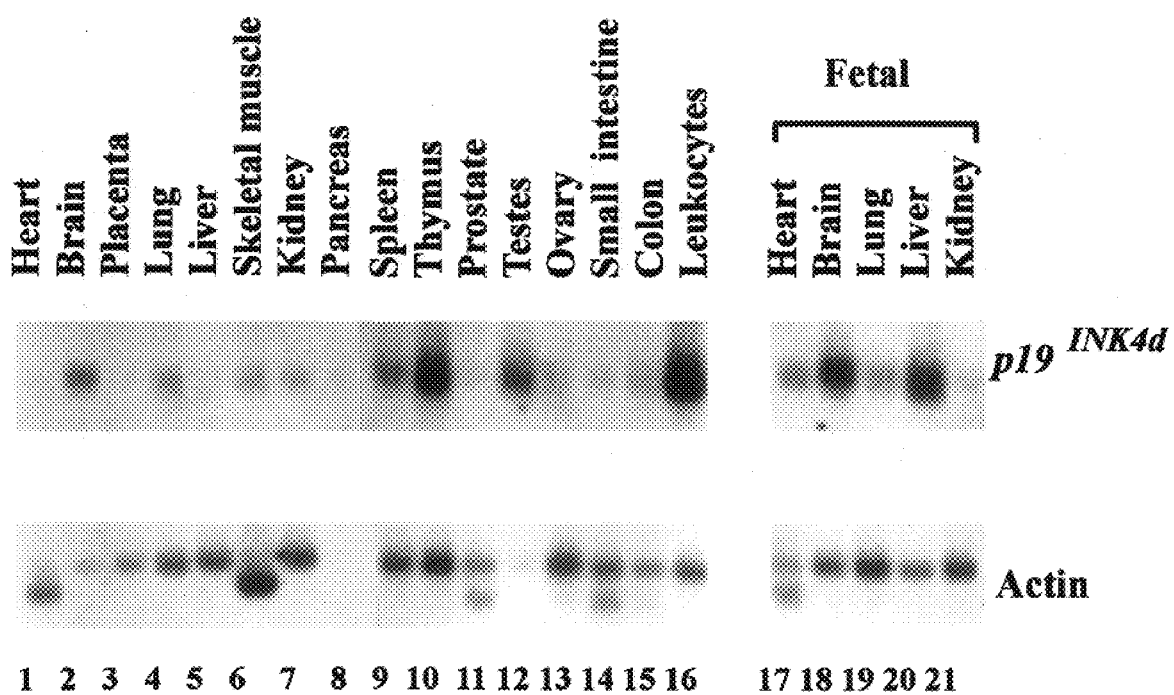
FIG. 11 shows the expression pattern of human INK4d-p19. Northern blots were prepared using the indicated human adult and fetal tissues. Two μg of poly(A)+ RNA were electrophoretically separated on agarose gels containing formaldehyde, transferred to nylon, and hybridized with $^{31}$P-labeled InK4d-p19 cDNA probe (p19$^{Ink4d}$). Filters were then stripped and rehybridized with a β-actin probe ("actin") to assess the amount of RNA per lane. Autoradiographic exposure times were 18 hrs for p19, and 8 hrs for actin.
Figure 12:
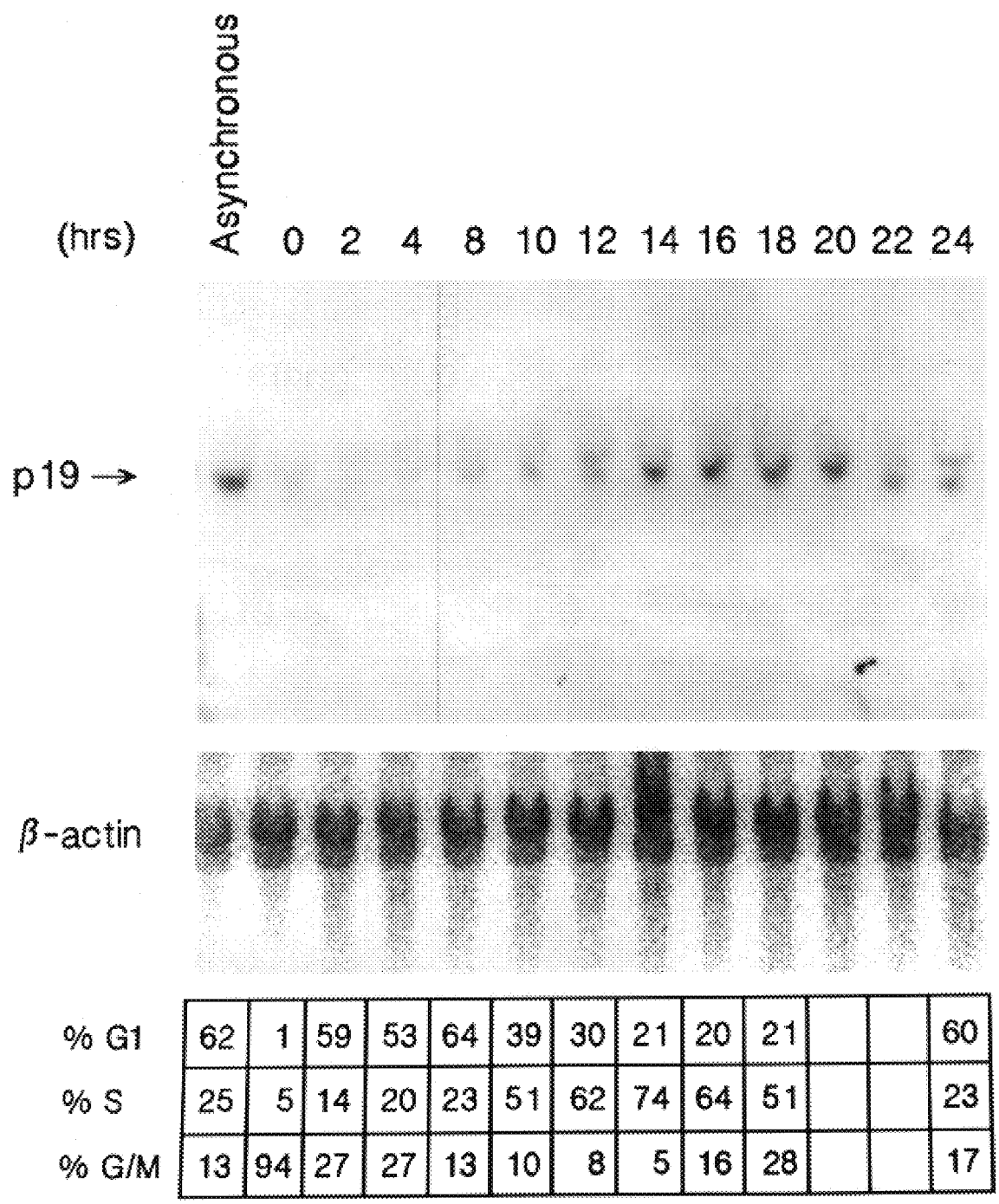
FIG. 12 shows the expression of p19 during the cell cycle in the human cervical carcinoma cell line HeLa. Human HeLa cells were arrested in mitosis by a sequential thymidine/nocodazole block. Mitotic cells were then harvested by mechanical release and re-seeded into culture dishes in the presence of complete medium containing 10% FCS. Total cellular RNA was extracted from cells at the indicated times and subjected to Northern blot analysis using either the p19 (top panel) or β-actin probes (middle panel). The different cell cycle phases were determined by flow cytometric analysis of cellular DNA content (bottom panel). The membrane was visualized using a Molecular Dynamics Phosphoimager 400A for either 6 hrs (p19 or 1 hr (β-actin).

Northern blot analysis of various human adult and fetal organs was used to assess the tissue distribution of human InK4d (p19) expression. A 1.4 kb transcript was expressed ubiquitously with high levels in brain, thymus, spleen, peripheral blood leukocyte and fetal liver as shown in FIG. 11. Because the expression levels of mouse p19 mRNA oscillate during the cell cycle in mouse macrophages (Example 5), the pattern of expression of human p19 was examined as a function of the cell cycle in the human cervical carcinoma cell line LeLa. Similar to the results shown in FIG. 7, Human InK4d mRNA was present in cells synchronized at mitosis with nocadazole block, and the MRNA level declined gradually according to the G1 progression after release from the drug. When approximately 50% of the cells began to enter S phase (12 hours after the release), the p19 mRNA signal began to rise and reached maximum expression at a point which corresponds to the entry from mid to late S phase for the majority of the cells (18–20 hours after the release) (FIG. 12).

Figure 13A:
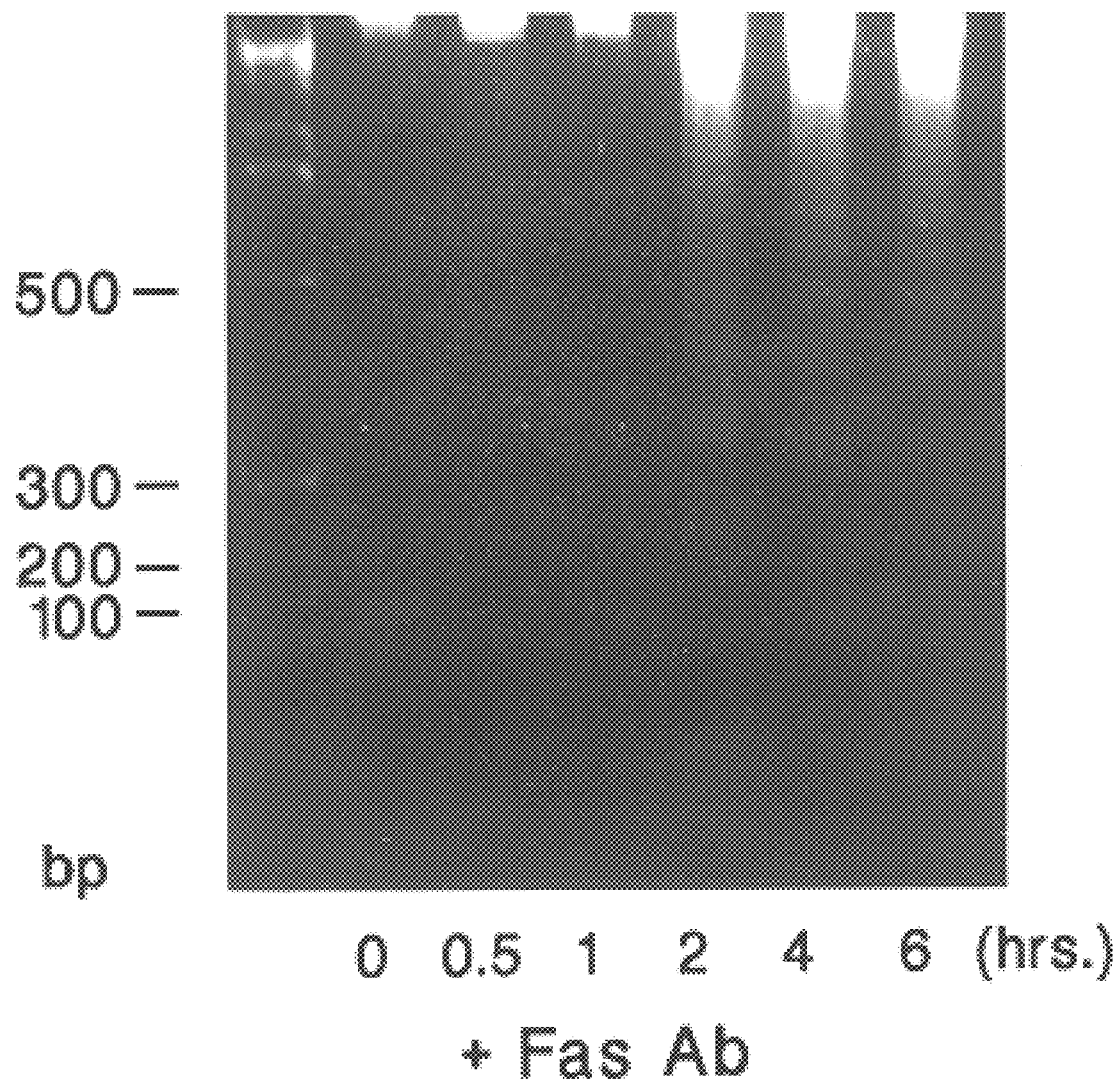
FIG. 13 shows the expression of p19 during Fas mediated apoptosis. Expression of p19 was examined using human CEM-C7 immature T cells treated with a Fas monoclonal antibody (Fas Ab). Human CEM-C7 cells were grown at a density of 2×10$^6$ cells per ml and treated with a Fas Ab at 100 ng/ml. Equivalent numbers of cells (2×10$^7$) were collected at various times after Ab treatment and used for RNA and DNA isolation. In panel A, DNA was analyzed by electrophoresis on 2% agarose-TBE gels containing ethidium bromide and visualized under ultraviolet light. The characteristic DNA ladder is apparent approximately 2 hrs post-Ab treatment. In panel B, total RNA extracted from untreated and Fas Ab-treated CEM-C7 cells was probed with the human p19 cDNA probe (left panel). The time post Fas Ab treatment is shown below each lane. The same RNA gel is shown visualized by ethidium bromide, with 18S and 28S NRAs marked (right panel). The Northern blot was visualized using a Molecular Dynamics Phosphoimager 400A for 6 hrs.
Figure 13B:
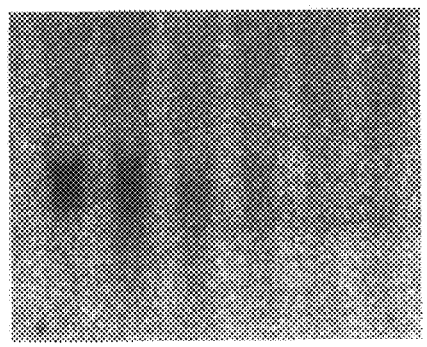
Figure 13C:
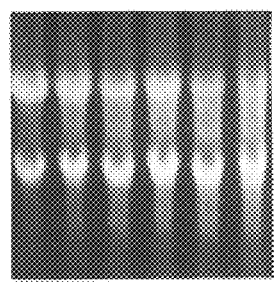

Several of the organs where human p19 gene is highly expressed are known to contain cells that are undergoing apoptosis. Accordingly, p19 expression during FAS-induced apoptosis was analyzed. As shown in FIG. 13, the immature T-cell line CEM-C7 undergoes apoptotic cell death with 1–2 hrs after treatment of FAS antibody. In this system, the p19 gene is rapidly (within 60 min.) down regulated by this treatment. In contrast, expression levels of other members of the InK4 gene family, InK4a-p16 and InK4b-p18, were maintained at a constant level for up to 6 hrs following FAS treatment (data not shown).

Example 11

Chromosomal Assignment of the Human p19 Gene

Fluorescence in situ hybridization (FISH) was used to define the chromosomal location of the gene for human p19 (Selleri et al., *Proc. Natl. Acad. Sci.* (*USA*) 88:887–891 (1991); Tkachuk et al., *Science* 250:559–562 (1990)). Bromodeoxyuridine-synchronized, phytohemagglutinin-stimulated peripheral blood lymphocytes from a normal male donor were used as a source of metaphase chromosomes. DNA from the human p19-containing P1-phage clone #3857 (Example 9) was nick-translated with digoxigenin-11-UTP (Boehringer Mannheim) and hybridized overnight at 37° C. to fixed metaphase chromosomes as described (Okuda et al., *Genomics* 21:217–821 (1994)). As a control probe to indicate the human chromosome 19 band q13, a cosmid clone for human D-site-binding protein gene (DBP) (Khatib et al., *Genomics* 23:344–351 (1994)) was labeled with biotin-11-dUTP (Gibco-BRL, Gaithersburg, Md.) and included in the incubation mixture. Specific hybridization signals were detected by applying the fluorescein-conjugated sheep antibodies to digoxigenin (Boehinger Marnheim), and avidin Texas red (Vector Laboratories Inc., Burlingame, Calif.) to biotin, followed by counter staining in propidium iodide (Sigma Chemicals, St. Louis, Mo.). Fluorescein microscopy was performed with a Zeiss standard microscope equipped with fluorescence filters to detect green signals (fluorescein-labeled p19) in comparison with red signals (Texas-red-labeled DBP on 19q13).

Figure 14:
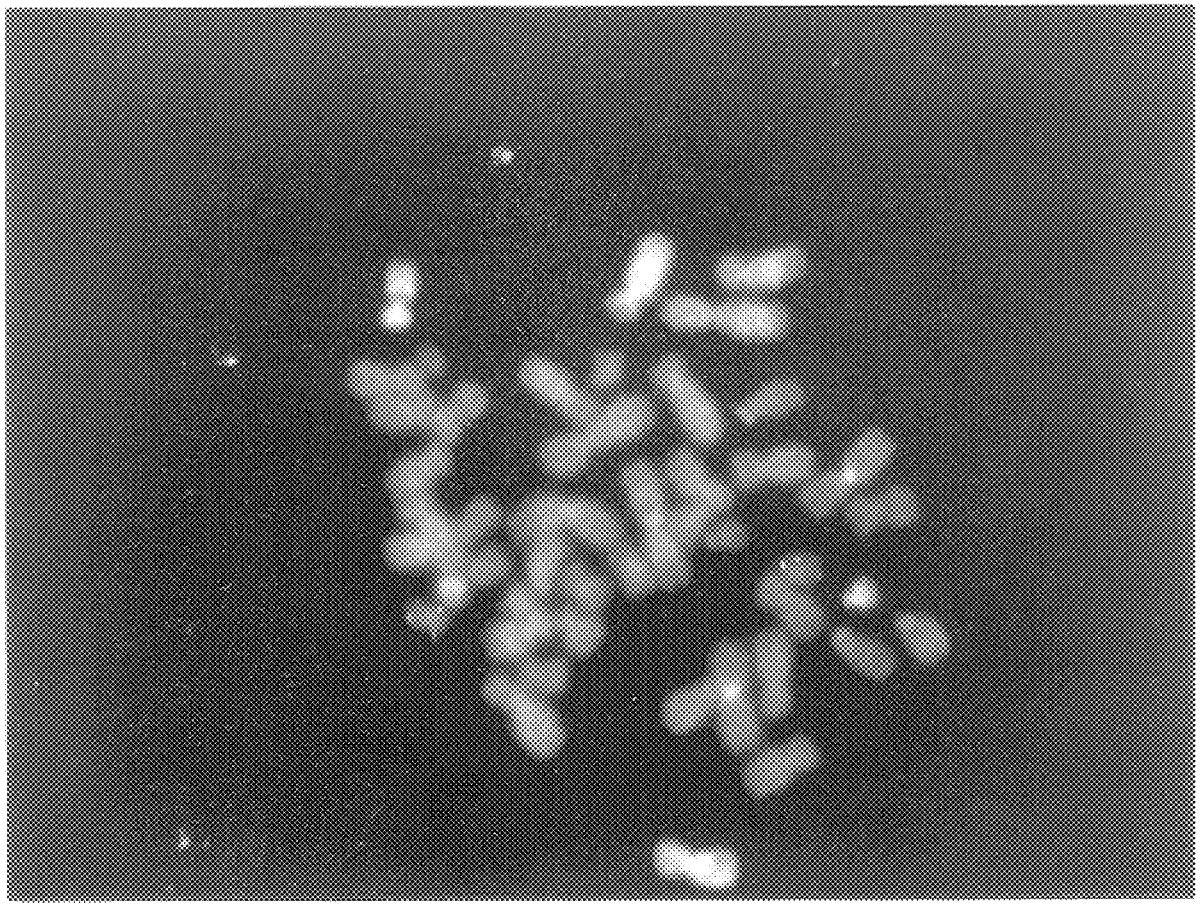
FIG. 14 shows the results of fluorescent in situ hybridization (FISH) of human chromosomes using a genomic P1 phage clone of human p19 sequences as a probe.

Analysis of metaphase preparations demonstrated the localization of p19 hybridizing sequences to a telomeric region on the short arm of chromosome 19 (FIG. 14). The identity of chromosome 19 was confirmed by the co-localization of the signal for the human DBP gene in the short arm of this chromosome in two-color analysis. On the basis of the distance of the signal from centromere relative to the entire length of the short arm, Ink4d, the gene for human p19, was assigned to band 19p13. Chromosome 19 band p13 is involved in non-random translocation t(1;19) (q23;p13), which is primarily observed in pediatric patients with acute lymphoblastic leukemia having a pre-B cell immunophenotype. Using the nucleic acids of the inventions as a probe, Southern blots were prepared on 3 pediatric ALL patients whose leukemic blasts contained a t(1;19) translocation. No evidence of a rearrangement in, or either hemizygous or homozygous loss of, InK4d-p19 was observed in these cases, suggesting that the InK4d gene was not involved in these particular translocations. The nucleic acids of the invention are useful as probes in hybridization analyses or, in the case of the oligonucleotides of the invention, as p19-specific primers for amplification and analysis of genomic DNA by PCR (Bos, J., in *PCR Technology: Principles and Applications for DNA Amplification*, Erlich, ed., Stockton Press, New York (1989), pages 225–233), in further studies of chromosomal structures in additional cases and types of carcinomas and neoplasms.

Deposits

A CDNA clone having coding sequences derived from the InK4c (p18) gene from mouse is contained in plasmid pSKp18$^{Ink4c\ (mouse)}$.

A cDNA clone having coding sequences derived from the InK4d (p19) gene from mouse is contained in plasmid pSKp19$^{Ink4d\ (mouse)}$.

A cDNA clone having coding sequences derived from the InK4d (p19) gene from human is contained in plasmid p19-4B.

Plasmids pSKp18$^{Ink4c\ (mouse)}$ and pSKp19$^{Ink4d\ (mouse)}$ were deposited under the Budapest Treaty with the American Type Culture Collection (A.T.C.C.), 12301 Parklawn Drive, Rockville, Md., 20852, U.S.A. on Feb. 6, 1995, and assigned the accession numbers 97045 and 97044, respectively. Plasmid p19-4B was deposited under the Budapest Treaty with the American Type Culture Collection (A.T.C.C.), 12301 Parklawn Drive, Rockville, Md., 20852, U.S.A. on Feb. 6, 1995, and assigned the accession number 97043. After issuance of a patent on this application, the A.T.C.C. will make the plasmids available to requesters in accordance with the Budapest Treaty and applicable U.S. patent laws and regulations. These deposits are not a license to practice the invention, and no admission is intended to be made that the deposits were necessary to satisfy the patent laws of the United States or any other country.

Utility of the Invention

The embodiments of the invention described above can be used for such purposes as listed below, alone or in combination with each other or other complementary methods and/or compositions.

(1) The nucleic acids of the invention, which include sequences encoding the polypeptide sequences of a p18 protein from a non-human mammal or a p19 protein from mice, humans and other mammals, are useful for producing p18 or p19 proteins, or fusion proteins derived therefrom, using recombinant DNA technology (see Example 2).

(2) Methods for detecting one or more nucleic acids encoding p18 or p19 polypeptide sequences, or alterations in such nucleic acids, are useful to diagnose certain types of cancers or to identify predispositions to certain types of cancers. The methods of the invention utilize one or more nucleic acids encoding p18 or p19 polypeptide sequences in hybridization and/or amplification assays specific for p18 or p19 genetic sequences. Genetic alterations in p18 or p19 nucleic acids that correlate with cancer and are detected by the methods of the invention include RFLPs, deletions, insertions, inversions, point mutations, altered mRNA splicing products, and the like. The methods for detecting p18 or p19 nucleic acids are also useful for isolating p18 or p19 nucleic acids from other mammals such as cats, dogs, horses, pigs, cows, etc. (see Example 8).

(3) The nucleic acids of the invention are also useful in methods of gene therapy in order to enhance or restore p18 or p19 activity in mammalian cells by, for example, directing the constitutive expression of a protein containing p18 or p19 polypeptide sequences in cells in need of regulation of cellular growth, the cell cycle, or DNA replication (see Example 7).

(4) One subset of the nucleic acids of the invention, antisense oligonucleotides that bind to mRNA molecules encoding p18 or p19, are useful for inhibiting p18 and/or p19 activity in mammalian cells in need of stimulation of cellular growth, the cell cycle, or DNA replication. In particular, cells in need of growth stimulation include hematopoietic stem cells. InK4c-p18 and InK4d-p19 are expressed at high levels in hematopoietic tissues, i.e., bone marrow and spleen, and may likely act to prevent the cycling of hematopoietic stem cells. A key goal of transplantation therapy is to grow hematopoietic stem cells in vitro, maintaining them in an immature, multipotential state. To the extent that these cells are kept out of cycle by CDK inhibitors p18 or p19, it is possible to move them into the cell cycle and grow them in vitro by reducing the amount of p18 or p19 present in stem cells by treatment with the antisense oliognucleotides of the invention.

(5) The nucleic acids of the invention are useful for making transgenic non-human animals that have a genetically engineered alteration in one or more nucleic acids encoding p18, p19 or both p18 and p19. In particular, the genomic DNA sequences of p18 and p19 from mice are used to generate transgenic mice that are homozygous for a p18 null allele, a p19 null allele, or for both p18 and p19 null alleles. Transgenic mice with reduced or absent p18 and/or p19 activity develop certain types of carcinomas and neoplasms in a reproducible and thus predictable manner, and serve as useful animal models for human cancers.

(6) Purified p18 or p19 proteins, peptide fragments and oligopeptides, or fusion proteins derived from the joining of a p18 or p19 polypeptide sequence with a second polypeptide sequence, inhibit mammalian cells from proceeding past the G1 phase of the cell cycle, i.e., prevent cells from initiating the replication of chromosomal DNA molecules. Purified p18 or p19 proteins or fusion proteins derived therefrom are useful for treating diseases characterized by uncontrolled cell growth such as cancers, carcinomas, tumors, neoplasms and the like. The p18 or p19 proteins, fusion proteins, peptide fragments or synthetic oligopeptides derived therefrom, can be introduced into eukaryotic cells to arrest their progression from G1 to S phases during interphase and thus inhibit growth of the cells, particularly cells undergoing rapid or uncontrolled growth (see Example 7).

(7) Methods are known in the art for using non-polypeptide G1 kinase inhibitors to distinguish and selectively kill transformed (neoplastic) cells and have been described by, e.g., Crissman et al. (U.S. Pat. No. 5,185,260 (Feb. 9, 1993)). Such methods reflect the fact that, at low doses, G1 kinase inhibitors selectively and reversibly arrest normal cells without arresting neoplastic cells; the latter may be selectively killed by therapeutic agents that do not affect normal cells in the G1 phase. The polypeptide G1 kinase inhibitors of the invention (i.e., p18 and p19 proteins or fusion proteins or oligopeptides derived therefrom) function in these methods with enhanced selectivity with regard to the G1 kinases (i.e., CDK4, CDK6) that are specifically inhibited thereby, and may be used in conjunction with chemotherapeutic agents known in the art to kill neoplastic cells.

(8) The methods and compositions of the invention are useful for the identification and design of synthetic compositions that inhibit p18 or p19 activities in vivo. For example, fusion polypeptides (see Example 2), peptide fragments generated by proteolysis or synthetic oligopeptides containing different portions of the p18 or p19 polypeptide sequences can be assayed for their ability to bind CDK4 and CDK6 kinases by using the assay described herein (see Example 3). In this fashion, the polypeptide sequences comprised within CDK-binding motifs are identified. The structure of these polypeptide motifs is used in turn in computer-assisted rational drug design to generate p18 or p19 mimetics that are assayed for their ability to bind CDK4 and/or CDK6 kinases according to the methods of the invention (Martin, Y. C., *Methods in Enzymology* 203:587–613 (1991)). The p18 or p19 mimetics can be introduced into eukaryotic cells to arrest their progression from G1 to S phases during interphase and thus inhibit growth of the cells (see Example 7).

(9) The proteins and polypeptide sequences of the invention are also useful as antigens in order to generate antibodies that specifically bind p18 or p19 epitopes. Specifically, p18 or p19 proteins, or fusion proteins derived therefrom, are produced by recombinant DNA technology and used to immunize animals. Alternatively, synthetic oligopeptides having polypeptide sequences derived from a p18 or p19 protein are prepared and used to immunize animals (see Example 6).

(10) Antibodies that specifically bind proteins having p18 or p19 polypeptide sequences (see Example 6) are useful in assays to detect various forms of, quantitate the levels of, or to determine the presence (or absence) and distribution of, p18 or p19 protein in cells from a mammal. Alterations in p18 or p19 polypeptides that correlate with cancer and are detected by the methods of the invention include, for example, truncated proteins resulting from aborted translation. Antibodies to p18 or p19 polypeptides are also used to isolate p18 or p19 proteins from other mammals such as cats, dogs, horses, pigs, cows, etc.

What is claimed is:

1. An isolated nucleic acid molecule comprising a sequence numbering at least 30 to all consecutive nucleotides of a nucleic acid sequence selected from the group consisting of SEQ ID NOS:5, 6, 7, 8, and a sequence complementary thereto, said isolated nucleic acid molecule optionally further comprises a detectable label.

2. A method of detecting a nucleic acid encoding an InK4d-p 19 protein, comprising (a) hybridizing nucleic acids in a sample with the isolated nucleic acid molecule of claim 1 that is detectably labeled; and (b) detecting the hybridized and labeled nucleic acid.

3. A method of inhibiting chromosomal DNA replication and arresting cell growth, comprising transforming a cultured eukaryotic cell with an expression vector comprising the isolated nucleic acid of claim 1, wherein said isolated nucleic acid encodes a complete Ink4d-p-19 polypeptide of SEQ ID NO:2 or SEQ ID NO:9, under conditions such that expression of said polypeptide inhibits chromosomal DNA replication or cell growth.

4. A method of producing a InK4d-p 19 polypeptide, comprising
   (a) transforming a eukaryotic cell with an expression vector comprising the isolated nucleic acid molecule of claim 1, wherein said isolated nucleic acid molecule encodes SEQ ID NO:2 or SEQ ID NO:9; and
   (b) providing culture conditions such that the InK4d-p19 polypeptide is expressed in said cell from said vector.

5. An isolated protein comprising the amino acid sequence as set forth in SEQ ID NO:2 or SEQ ID NO:9.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 168 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Met Ala Glu Pro Trp Gly Asn Glu Leu Ala Ser Ala Ala Arg Gly
1               5                   10                  15

Asp Leu Glu Gln Leu Thr Ser Leu Leu Gln Asn Asn Val Asn Val Asn
                20                  25                  30

Ala Gln Asn Gly Phe Gly Arg Thr Ala Leu Gln Val Met Lys Leu Gly
            35                  40                  45

Asn Pro Glu Ile Ala Arg Arg Leu Leu Leu Arg Gly Ala Asn Pro Asn
50                  55                  60

Leu Lys Asp Gly Thr Gly Phe Ala Val Ile His Asp Ala Ala Arg Ala
65                  70                  75                  80

Gly Phe Leu Asp Thr Val Gln Ala Leu Leu Glu Phe Gln Ala Asp Val
                85                  90                  95

Asn Ile Glu Asp Asn Glu Gly Asn Leu Pro Leu His Leu Ala Ala Lys
            100                 105                 110

Glu Gly His Leu Pro Val Val Glu Phe Leu Met Lys His Thr Ala Cys
        115                 120                 125

Asn Val Gly His Arg Asn His Lys Gly Asp Thr Ala Phe Asp Leu Ala
130                 135                 140

Arg Phe Tyr Gly Arg Asn Glu Val Ile Ser Leu Met Glu Ala Asn Gly
145                 150                 155                 160

Val Gly Gly Ala Thr Ser Leu Gln
                165
```

(2) INFORMATION FOR SEQ ID NO:2:

(i) SEQUENCE CHARACTERISTICS:
      (A) LENGTH: 166 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

```
Met Leu Leu Glu Glu Val Cys Val Gly Asp Arg Leu Ser Gly Ala Arg
1               5                   10                  15

Ala Arg Gly Asp Val Gln Glu Val Arg Arg Leu Leu His Arg Glu Leu
                20                  25                  30

Val His Pro Asp Ala Leu Asn Arg Phe Gly Lys Thr Ala Leu Gln Val
            35                  40                  45

Met Met Phe Gly Ser Pro Ala Val Ala Leu Glu Leu Leu Lys Gln Gly
        50                  55                  60

Ala Ser Pro Asn Val Gln Asp Ala Ser Gly Thr Ser Pro Val His Asp
```

```
               65                  70                  75                  80
Ala Ala Arg Thr Gly Phe Leu Asp Thr Leu Lys Val Leu Val Glu His
                    85                  90                  95

Gly Ala Asp Val Asn Ala Leu Asp Ser Thr Gly Ser Leu Pro Ile His
                100                 105                 110

Leu Ala Ile Arg Glu Gly His Ser Ser Val Val Ser Phe Leu Ala Pro
            115                 120                 125

Glu Ser Asp Leu His His Arg Asp Ala Ser Gly Leu Thr Pro Leu Glu
        130                 135                 140

Leu Ala Arg Gln Arg Gly Ala Gln Asn Leu Met Asp Ile Leu Gln Gly
145                 150                 155                 160

His Met Met Ile Pro Met
                165
```

(2) INFORMATION FOR SEQ ID NO:3:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
ATGGCCGAGC CTTGGGGAA CGAGTTGGCG TCCGCAGCTG CCAGGGGGGA CCTAGAGCAA    60
CTTACTAGTT TGTTGCAAAA TAATGTAAAC GTCAACGCTC AAAATGGATT TGGGAGAACT   120
GCGCTGCAGG TTATGAAACT TGGAAATCCG GAGATTGCCA GGAGGCTTCT CCTCAGAGGT   180
GCTAATCCCA ATTTGAAAGA TGGAACTGGT TTTGCTGTCA TTCATGATGC TGCCAGAGCA   240
GGTTTCCTGG ACACTGTACA GGCTTTGCTG GAGTTCCAGG CTGATGTTAA CATTGAAGAT   300
AATGAAGGGA ACCTGCCCTT GCACTTGGCT GCCAAAGAAG GCCACCTCCC TGTGGTGGAG   360
TTCCTTATGA AGCACACAGC CTGCAATGTG GGGCATCGGA ACCATAAGGG GGACACCGCC   420
TTCGACTTGG CCAGGTTCTA TGGAAGAAAT GAGGTCATTA GCCTGATGGA GGCAAATGGG   480
GTTGGGGGAG CCACAAGCCT GCAGTGA                                      507
```

(2) INFORMATION FOR SEQ ID NO:4:

(i) SEQUENCE CHARACTERISTICS:
        (A) LENGTH: 694 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
CCTCGAGATT TACCCTGCGA AGGACCTGAC TCTGAAATTC TGCCTCAAAT CACCACTGTG    60
AACAAGGGAC CCTAAAGAAT GGCCGAGCCT TGGGGGAACG AGTTGGCGTC CGCAGCTGCC   120
AGGGGGGACC TAGAGCAACT TACTAGTTTG TTGCAAAATA ATGTAAACGT CAACGCTCAA   180
AATGGATTTG GGAGAACTGC GCTGCAGGTT ATGAAACTTG GAAATCCGGA GATTGCCAGG   240
AGGCTTCTCC TCAGAGGTGC TAATCCCAAT TTGAAAGATG GAACTGGTTT TGCTGTCATT   300
CATGATGCTG CCAGAGCAGG TTTCCTGGAC ACTGTACAGG CTTTGCTGGA GTTCCAGGCT   360
GATGTTAACA TTGAAGATAA TGAAGGGAAC CTGCCCTTGC ACTTGGCTGC CAAAGAAGGC   420
CACCTCCCTG TGGTGGAGTT CCTTATGAAG CACACAGCCT GCAATGTGGG GCATCGGAAC   480
```

```
CATAAGGGGG ACACCGCCTT CGACTTGGCC AGGTTCTATG GAAGAAATGA GGTCATTAGC    540

CTGATGGAGG CAAATGGGGT TGGGGGAGCC ACAAGCCTGC AGTGAATGTG TAGAGGTCTC    600

TCTCACTGAC CTCACACTGT CCGTTAGTTG GTTGGCTGTC CGTTTCACTA TCACTTATTA    660

AAATATAGGG TTTCTTCGCT TTGTTTTAAA ATAT                                694
```

(2) INFORMATION FOR SEQ ID NO:5:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
ATGCTTCTGG AAGAAGTCTG CGTCGGCGAC CGGTTGAGTG GCGCACGGGC CCGTGGCGAC     60

GTGCAAGAGG TCCGCCGCCT TCTTCACCGG GAGCTGGTGC ATCCTGACGC CCTGAACCGC    120

TTTGGCAAGA CGGCCTTGCA GGTCATGATG TTTGGAAGTC CAGCAGTTGC TTTGGAGCTC    180

CTGAAGCAAG GTGCCAGCCC CAATGTCCAA GATGCCTCCG GTACTAGTCC TGTGCATGAT    240

GCGGCTCGCA CCGGGTTCCT GGACACCCTG AAGGTTCTGG TGGAGCATGG TGCTGATGTC    300

AATGCCCTGG ACAGCACTGG GTCGCTCCCC ATCCATCTGG CGATAAGAGA GGGCCATAGC    360

TCCGTGGTCA GCTTCCTAGC TCCTGAATCT GATCTCCACC ACAGGGACGC TTCCGGTCTC    420

ACTCCCCTGG AGTTGGCTCG GCAGAGAGGG GCTCAGAACC TCATGGACAT TCTGCAGGGG    480

CACATGATGA TCCCAATGTG A                                              501
```

(2) INFORMATION FOR SEQ ID NO:6:

(i) SEQUENCE CHARACTERISTICS:
        (A) LENGTH: 941 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
CGAATTCGGC ACGAGAGTTG GCCCTGGTGG CACCGCAGTC CCTAGAGTTC TGATCCAGCT     60

CTTGCTGGTT CCCCAGCCCT GACCTTAACT GGGCTTGGGG CTGGGTGGGT TTCACAGTCC    120

ACCGGTATCC ACTATGCTTC TGGAAGAAGT CTGCGTCGGC GACCGGTTGA GTGGCGCACG    180

GGCCCGTGGC GACGTGCAAG AGGTCCGCCG CCTTCTTCAC CGGGAGCTGG TGCATCCTGA    240

CGCCCTGAAC CGCTTTGGCA AGACGGCCTT GCAGGTCATG ATGTTTGGAA GTCCAGCAGT    300

TGCTTTGGAG CTCCTGAAGC AAGGTGCCAG CCCCAATGTC CAAGATGCCT CCGGTACTAG    360

TCCTGTGCAT GATGCGGCTC GCACCGGGTT CCTGGACACC CTGAAGGTTC TGGTGGAGCA    420

TGGTGCTGAT GTCAATGCCC TGGACAGCAC TGGGTCGCTC CCCATCCATC TGGCGATAAG    480

AGAGGGCCAT AGCTCCGTGG TCAGCTTCCT AGCTCCTGAA TCTGATCTCC ACCACAGGGA    540

CGCTTCCGGT CTCACTCCCC TGGAGTTGGC TCGGCAGAGA GGGGCTCAGA ACCTCATGGA    600

CATTCTGCAG GGGCACATGA TGATCCCAAT GTGACCCAAG GCCACTGTCT CCAGCCTTAC    660

TGGGTTACTT GTCAACAAAA GAGGAAAGAA ACTTTCTCTT TTCACACCTG TCCATTGAAG    720

AAGGGAGTGG GAGGAGCAGT TTGTGGTTTA TTGGTGTTGA TTTCTTGAGT GTGTGTGTTT    780
```

```
GGGGGGTGTT TCTCATTTGT TTTTCCTCAC CCCTTTTGGT GTGTTGGAAA AGAAGGGTCC        840

TACAGGCAAC AGATCTAAAT GGTTCAGTTT CCTCTGCACT GGGGCTGCAC CAGGGCAGGG        900

GTTAAAGCCC TAGCCTCAGA GTGAGGTCAT CACTTCCCGG G                            941

(2) INFORMATION FOR SEQ ID NO:7:

(i) SEQUENCE CHARACTERISTICS:
        (A) LENGTH: 555 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TGACAGCGCC GGGCTGGGGC GGGGCGGGGG GCTTTGCAGG CCGCCAGTGT CGACATGCTG         60

CTGGAGGAGG TTCGCGCCGG CGACCGGCTG AGTGGGCGG CGGCCCGGGG CGACGTGCAG        120

GAGGTGCGCC GCCTTCTGCA CCGCGAGCTG GTGCATCCCG ACGCCCTCAA CCGCTTCGGC        180

AAGACGGCGC TGCAGGTCAT GATGTTTGGC AGCACCGCCA TCGCCCTGGA GCTGCTGAAG        240

CAAGGTGCCA GCCCCAATGT CCAGGACACC TCCGGTACCA GTCCAGTCCA TGACGCAGCC        300

CGCACTGGAT TCCTGGACAC CCTGAAGGTC CTAGTGGAGC ACGGGGCTGA TGTCAACGTG        360

CCTGATGGCA CCGGGGCACT TCCAATCCAT CTGGCAGTTC AAGAGGGTCA CACTGCTGTG        420

GTCAGCTTTC TGGCAGCTGA ATCTGATCTC CATCGCAGGG ACGCCAGGGG TCTCACACCC        480

TTGGAGCTGG CACTGCAGAG AGGGGCTCAG GACCTCGTGG ACATCCTGCA GGGCCACATG        540

GTGGCCCCGC TGTGA                                                        555

(2) INFORMATION FOR SEQ ID NO:8:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..501

(xi) SEQUENCE DESCRIPTION: SEQ ID NO:8:

ATG CTG CTG GAG GAG GTT CGC GCC GGC GAC CGG CTG AGT GGG GCG GCG          48
Met Leu Leu Glu Glu Val Arg Ala Gly Asp Arg Leu Ser Gly Ala Ala
 1               5                  10                  15

GCC CGG GGC GAC GTG CAG GAG GTG CGC CGC CTT CTG CAC CGC GAG CTG          96
Ala Arg Gly Asp Val Gln Glu Val Arg Arg Leu Leu His Arg Glu Leu
             20                  25                  30

GTG CAT CCC GAC GCC CTC AAC CGC TTC GGC AAG ACG GCG CTG CAG GTC         144
Val His Pro Asp Ala Leu Asn Arg Phe Gly Lys Thr Ala Leu Gln Val
         35                  40                  45

ATG ATG TTT GGC AGC ACC GCC ATC GCC CTG GAG CTG CTG AAG CAA GGT         192
Met Met Phe Gly Ser Thr Ala Ile Ala Leu Glu Leu Leu Lys Gln Gly
     50                  55                  60

GCC AGC CCC AAT GTC CAG GAC ACC TCC GGT ACC AGT CCA GTC CAT GAC         240
Ala Ser Pro Asn Val Gln Asp Thr Ser Gly Thr Ser Pro Val His Asp
 65                  70                  75                  80

GCA GCC CGC ACT GGA TTC CTG GAC ACC CTG AAG GTC CTA GTG GAG CAC         288
Ala Ala Arg Thr Gly Phe Leu Asp Thr Leu Lys Val Leu Val Glu His
                 85                  90                  95
```

```
GGG GCT GAT GTC AAC GTG CCT GAT GGC ACC GGG GCA CTT CCA ATC CAT        336
Gly Ala Asp Val Asn Val Pro Asp Gly Thr Gly Ala Leu Pro Ile His
            100                 105                 110

CTG GCA GTT CAA GAG GGT CAC ACT GCT GTG GTC AGC TTT CTG GCA GCT        384
Leu Ala Val Gln Glu Gly His Thr Ala Val Val Ser Phe Leu Ala Ala
        115                 120                 125

GAA TCT GAT CTC CAT CGC AGG GAC GCC AGG GGT CTC ACA CCC TTG GAG        432
Glu Ser Asp Leu His Arg Arg Asp Ala Arg Gly Leu Thr Pro Leu Glu
    130                 135                 140

CTG GCA CTG CAG AGA GGG GCT CAG GAC CTC GTG GAC ATC CTG CAG GGC        480
Leu Ala Leu Gln Arg Gly Ala Gln Asp Leu Val Asp Ile Leu Gln Gly
145                 150                 155                 160

CAC ATG GTG GCC CCG CTG TGA                                            501
His Met Val Ala Pro Leu  *
                165
```

(2) INFORMATION FOR SEQ ID NO:9:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO:9:

```
Met Leu Leu Glu Glu Val Arg Ala Gly Asp Arg Leu Ser Gly Ala Ala
 1               5                  10                  15

Ala Arg Gly Asp Val Gln Glu Val Arg Arg Leu Leu His Arg Glu Leu
            20                  25                  30

Val His Pro Asp Ala Leu Asn Arg Phe Gly Lys Thr Ala Leu Gln Val
        35                  40                  45

Met Met Phe Gly Ser Thr Ala Ile Ala Leu Glu Leu Leu Lys Gln Gly
    50                  55                  60

Ala Ser Pro Asn Val Gln Asp Thr Ser Gly Thr Ser Pro Val His Asp
65                  70                  75                  80

Ala Ala Arg Thr Gly Phe Leu Asp Thr Leu Lys Val Leu Val Glu His
            85                  90                  95

Gly Ala Asp Val Asn Val Pro Asp Gly Thr Gly Ala Leu Pro Ile His
            100                 105                 110

Leu Ala Val Gln Glu Gly His Thr Ala Val Val Ser Phe Leu Ala Ala
        115                 120                 125

Glu Ser Asp Leu His Arg Arg Asp Ala Arg Gly Leu Thr Pro Leu Glu
    130                 135                 140

Leu Ala Leu Gln Arg Gly Ala Gln Asp Leu Val Asp Ile Leu Gln Gly
145                 150                 155                 160

His Met Val Ala Pro Leu
                165
```

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CCGGATCCAT GGCCGAGCCT TGGGG                                              25

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CCGAATTCTC ACTGCAGGCT TGTGG                                              25

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CCGGATCCAT GCTTCTGGAA GAAGT                                              25

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CCGAATTCTC ACATTGGGAT CATCA                                              25

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

AGCAAGGTGC CAGCCCCAAT GTCCA                                              25

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GCGTCCCTGC GATGGAGATC AGATT                                              25

(2) INFORMATION FOR SEQ ID NO:16:
```

```
    (i) SEQUENCE CHARACTERISTICS:
        (A) LENGTH: 148 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Met Glu Pro Ser Ala Asp Trp Leu Ala Thr Ala Ala Arg Gly Arg
1               5                  10                  15

Val Glu Glu Val Arg Ala Leu Leu Glu Ala Val Ala Leu Pro Asn Ala
                20                  25                  30

Pro Asn Ser Tyr Gly Arg Arg Pro Ile Gln Val Met Met Met Gly Ser
            35                  40                  45

Ala Arg Val Ala Glu Leu Leu Leu Leu His Gly Ala Glu Pro Asn Cys
        50                  55                  60

Ala Asp Pro Ala Thr Leu Thr Arg Pro Val His Asp Ala Ala Arg Glu
65                  70                  75                  80

Gly Phe Leu Asp Thr Leu Val Val Leu His Arg Ala Gly Ala Arg Leu
                85                  90                  95

Asp Val Arg Asp Ala Trp Gly Arg Leu Pro Val Asp Leu Ala Glu Glu
                100                 105                 110

Leu Gly His Arg Asp Val Ala Arg Tyr Leu Arg Ala Ala Gly Gly
            115                 120                 125

Thr Arg Gly Ser Asn His Ala Arg Ile Asp Ala Ala Glu Gly Pro Ser
            130                 135                 140

Asp Ile Pro Asp
145

(2) INFORMATION FOR SEQ ID NO:17:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Met Leu Leu Glu Glu Val Cys Val Gly Asp Arg Leu Ser Gly Ala Arg
1               5                  10                  15

Ala Arg Gly Asp Val Gln Glu Val Arg Arg Leu Leu His Arg Glu Leu
                20                  25                  30

Val His Pro Asp Ala Leu Asn Arg Phe Gly Lys Thr Ala Leu Gln Val
            35                  40                  45

Met Met Phe Gly Ser Pro Ala Val Ala Leu Glu Leu Leu Lys Gln Gly
        50                  55                  60

Ala Ser Pro Asn Val Gln Asp Ala Ser Gly Thr Ser Pro Val His Asp
65                  70                  75                  80

Ala Ala Arg Thr Gly Phe Leu Asp Thr Leu Lys Val Leu Val Glu His
                85                  90                  95

Gly Ala Asp Val Asn Ala Leu Asp Ser Thr Gly Ser Leu Pro Ile His
                100                 105                 110

Leu Ala Ile Arg Glu Gly His Ser Ser Val Val Ser Phe Leu Ala Pro
            115                 120                 125

Glu Ser Asp Leu His His Arg Asp Ala Ser Gly Leu Thr Pro Leu Glu
```

-continued

```
            130                 135                 140
Leu Ala Arg Gln Arg Gly Ala Gln Asn Leu Met Asp Ile Leu Gln Gly
145                 150                 155                 160

His Met Met Ile Pro Met
                165
```

(2) INFORMATION FOR SEQ ID NO:18:

(i) SEQUENCE CHARACTERISTICS:
        (A) LENGTH: 168 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Met Ala Glu Pro Trp Gly Asn Glu Leu Ala Ser Ala Ala Ala Arg Gly
1               5                   10                  15

Asp Leu Glu Gln Leu Thr Ser Leu Leu Gln Asn Asn Val Asn Val Asn
                20                  25                  30

Ala Gln Asn Gly Phe Gly Arg Thr Ala Leu Gln Val Met Lys Leu Gly
            35                  40                  45

Asn Pro Glu Ile Ala Arg Arg Leu Leu Leu Arg Gly Ala Asn Pro Asn
50                  55                  60

Leu Lys Asp Gly Thr Gly Phe Ala Val Ile His Asp Ala Ala Arg Ala
65                  70                  75                  80

Gly Phe Leu Asp Thr Val Gln Ala Leu Leu Glu Phe Gln Ala Asp Val
                85                  90                  95

Asn Ile Glu Asp Asn Glu Gly Asn Leu Pro Leu His Leu Ala Ala Lys
                100                 105                 110

Glu Gly His Leu Pro Val Val Glu Phe Leu Met Lys His Thr Ala Cys
            115                 120                 125

Asn Val Gly His Arg Asn His Lys Gly Asp Thr Ala Phe Asp Leu Ala
130                 135                 140

Arg Phe Tyr Gly Arg Asn Glu Val Ile Ser Leu Met Glu Ala Asn Gly
145                 150                 155                 160

Val Gly Gly Ala Thr Ser Leu Gln
                165
```

(2) INFORMATION FOR SEQ ID NO:19:

(i) SEQUENCE CHARACTERISTICS:
        (A) LENGTH: 555 base pairs
        (B) TYPE: nucleic acid
        (C) STRANDEDNESS: single
        (D) TOPOLOGY: linear (ii) MOLECULE TYPE: peptide (ix) FEATURE:
        (A) NAME/KEY: CDS
        (B) LOCATION: 55..552

(xi) SEQUENCE DESCRIPTION: SEQ ID NO:19:

```
TGACAGCGCC GGGCTGGGGC GGGGCGGGGG GCTTTGCAGG CCGCCAGTGT CGAC ATG     57
                                                              Met
                                                              1

CTG CTG GAG GAG GTT CGC GCC GGC GAC CGG CTG AGT GGG GCG GCG GCC    105
Leu Leu Glu Glu Val Arg Ala Gly Asp Arg Leu Ser Gly Ala Ala Ala
        5                   10                  15
```

```
CGG GGC GAC GTG CAG GAG GTG CGC CGC CTT CTG CAC CGC GAG CTG GTG        153
Arg Gly Asp Val Gln Glu Val Arg Arg Leu Leu His Arg Glu Leu Val
         20                  25                  30

CAT CCC GAC GCC CTC AAC CGC TTC GGC AAG ACG GCG CTG CAG GTC ATG        201
His Pro Asp Ala Leu Asn Arg Phe Gly Lys Thr Ala Leu Gln Val Met
 35                  40                  45

ATG TTT GGC AGC ACC GCC ATC GCC CTG GAG CTG CTG AAG CAA GGT GCC        249
Met Phe Gly Ser Thr Ala Ile Ala Leu Glu Leu Leu Lys Gln Gly Ala
 50                  55                  60                  65

AGC CCC AAT GTC CAG GAC ACC TCC GGT ACC AGT CCA GTC CAT GAC GCA        297
Ser Pro Asn Val Gln Asp Thr Ser Gly Thr Ser Pro Val His Asp Ala
             70                  75                  80

GCC CGC ACT GGA TTC CTG GAC ACC CTG AAG GTC CTA GTG GAG CAC GGG        345
Ala Arg Thr Gly Phe Leu Asp Thr Leu Lys Val Leu Val Glu His Gly
         85                  90                  95

GCT GAT GTC AAC GTG CCT GAT GGC ACC GGG GCA CTT CCA ATC CAT CTG        393
Ala Asp Val Asn Val Pro Asp Gly Thr Gly Ala Leu Pro Ile His Leu
100                 105                 110

GCA GTT CAA GAG GGT CAC ACT GCT GTG GTC AGC TTT CTG GCA GCT GAA        441
Ala Val Gln Glu Gly His Thr Ala Val Val Ser Phe Leu Ala Ala Glu
     115                 120                 125

TCT GAT CTC CAT CGC AGG GAC GCC AGG GGT CTC ACA CCC TTG GAG CTG        489
Ser Asp Leu His Arg Arg Asp Ala Arg Gly Leu Thr Pro Leu Glu Leu
130                 135                 140                 145

GCA CTG CAG AGA GGG GCT CAG GAC CTC GTG GAC ATC CTG CAG GGC CAC        537
Ala Leu Gln Arg Gly Ala Gln Asp Leu Val Asp Ile Leu Gln Gly His
                150                 155                 160

ATG GTG GCC CCG CTG TGA                                                 555
Met Val Ala Pro Leu
             165

(2) INFORMATION FOR SEQ ID NO:20:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO:20:

Met Leu Leu Glu Glu Val Arg Ala Gly Asp Arg Leu Ser Gly Ala Ala
 1               5                  10                  15

Ala Arg Gly Asp Val Gln Glu Val Arg Arg Leu Leu His Arg Glu Leu
             20                  25                  30

Val His Pro Asp Ala Leu Asn Arg Phe Gly Lys Thr Ala Leu Gln Val
         35                  40                  45

Met Met Phe Gly Ser Thr Ala Ile Ala Leu Glu Leu Leu Lys Gln Gly
 50                  55                  60

Ala Ser Pro Asn Val Gln Asp Thr Ser Gly Thr Ser Pro Val His Asp
 65                  70                  75                  80

Ala Ala Arg Thr Gly Phe Leu Asp Thr Leu Lys Val Leu Val Glu His
                 85                  90                  95

Gly Ala Asp Val Asn Val Pro Asp Gly Thr Gly Ala Leu Pro Ile His
            100                 105                 110

Leu Ala Val Gln Glu Gly His Thr Ala Val Val Ser Phe Leu Ala Ala
        115                 120                 125

Glu Ser Asp Leu His Arg Arg Asp Ala Arg Gly Leu Thr Pro Leu Glu
    130                 135                 140
```

Leu Ala Leu Gln Arg Gly Ala Gln Asp Leu Val Asp Ile Leu Gln Gly
145                 150                 155                 160

His Met Val Ala Pro Leu
                165

(2) INFORMATION FOR SEQ ID NO:21:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Met Leu Leu Glu Glu Val Arg Ala Gly Asp Arg Leu Ser Gly Ala Ala
1               5                   10                  15

Ala Arg Gly Asp Val Gln Glu Val Arg Arg Leu Leu His Arg Glu Leu
                20                  25                  30

Val His Pro Asp Ala Leu Asn Arg Phe Gly Lys Thr Ala Leu Gln Val
            35                  40                  45

Met Met Phe Gly Ser Thr Ala Ile Ala Leu Glu Leu Leu Lys Gln Gly
50                  55                  60

Ala Ser Pro Asn Val Gln Asp Thr Ser Gly Thr Ser Pro Val His Asp
65                  70                  75                  80

Ala Ala Arg Thr Gly Phe Leu Asp Thr Leu Lys Val Leu Val Glu His
                85                  90                  95

Gly Ala Asp Val Asn Val Pro Asp Gly Thr Gly Ala Leu Pro Ile His
                100                 105                 110

Leu Ala Val Gln Glu Gly His Thr Ala Val Val Ser Phe Leu Ala Ala
            115                 120                 125

Glu Ser Asp Leu His Arg Arg Asp Ala Arg Gly Leu Thr Pro Leu Glu
130                 135                 140

Leu Ala Leu Gln Arg Gly Ala Gln Asp Leu Val Asp Ile Leu Gln Gly
145                 150                 155                 160

His Met Val Ala Pro Leu
                165

(2) INFORMATION FOR SEQ ID NO:22:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Met Leu Leu Glu Glu Val Cys Val Gly Asp Arg Leu Ser Gly Ala Arg
1               5                   10                  15

Ala Arg Gly Asp Val Gln Glu Val Arg Arg Leu Leu His Arg Glu Leu
                20                  25                  30

Val His Pro Asp Ala Leu Asn Arg Phe Gly Lys Thr Ala Leu Gln Val
            35                  40                  45

Met Met Phe Gly Ser Pro Ala Val Ala Leu Glu Leu Leu Lys Gln Gly
50                  55                  60

Ala Ser Pro Asn Val Gln Asp Ala Ser Gly Thr Ser Pro Val His Asp
65                  70                  75                  80

```
Ala Ala Arg Thr Gly Phe Leu Asp Thr Leu Lys Val Leu Val Glu His
                85                  90                  95

Gly Ala Asp Val Asn Ala Leu Asp Ser Thr Gly Ser Leu Pro Ile His
                100                 105                 110

Leu Ala Ile Arg Glu Gly His Ser Val Val Ser Phe Leu Ala Pro
            115                 120                 125

Glu Ser Asp Leu His His Arg Asp Ala Ser Gly Leu Thr Pro Leu Glu
        130                 135                 140

Leu Ala Arg Gln Arg Gly Ala Gln Asn Leu Met Asp Ile Leu Gln Gly
145                 150                 155                 160

His Met Met Ile Pro Met
                165
```

(2) INFORMATION FOR SEQ ID NO:23:

(i) SEQUENCE CHARACTERISTICS:
        (A) LENGTH: 168 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Met Ala Glu Pro Trp Gly Asn Glu Leu Ala Ser Ala Ala Arg Gly
1               5                   10                  15

Asp Leu Glu Gln Leu Thr Ser Leu Leu Gln Asn Asn Val Asn Val Asn
                20                  25                  30

Ala Gln Asn Gly Phe Gly Arg Thr Ala Leu Gln Val Met Lys Leu Gly
            35                  40                  45

Asn Pro Glu Ile Ala Arg Arg Leu Leu Leu Arg Gly Ala Asn Pro Asp
        50                  55                  60

Leu Lys Asp Arg Thr Gly Phe Ala Val Ile His Asp Ala Ala Arg Ala
65                  70                  75                  80

Gly Phe Leu Asp Thr Leu Gln Thr Leu Leu Glu Phe Gln Ala Asp Val
                85                  90                  95

Asn Ile Glu Asp Asn Glu Gly Asn Leu Pro Leu His Leu Ala Ala Lys
                100                 105                 110

Glu Gly His Leu Arg Val Val Glu Phe Leu Val Lys His Thr Ala Ser
            115                 120                 125

Asn Val Gly His Arg Asn His Lys Gly Asp Thr Ala Cys Asp Leu Ala
        130                 135                 140

Arg Leu Tyr Gly Arg Asn Glu Val Val Ser Leu Met Gln Ala Asn Gly
145                 150                 155                 160

Ala Gly Gly Ala Thr Asn Leu Gln
                165
```

(2) INFORMATION FOR SEQ ID NO:24:

(i) SEQUENCE CHARACTERISTICS:
        (A) LENGTH: 148 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Met Glu Pro Ser Ala Asp Trp Leu Ala Thr Ala Ala Ala Arg Gly Arg
```

-continued

```
1               5               10              15
Val Glu Glu Val Arg Ala Leu Leu Glu Ala Val Ala Leu Pro Asn Ala
                20              25              30

Pro Asn Ser Tyr Gly Arg Arg Pro Ile Gln Val Met Met Met Gly Ser
            35              40              45

Ala Arg Val Ala Glu Leu Leu Leu His Gly Ala Glu Pro Asn Cys
        50              55              60

Ala Asp Pro Ala Thr Leu Thr Arg Pro Val His Asp Ala Ala Arg Glu
65              70              75              80

Gly Phe Leu Asp Thr Leu Val Val Leu His Arg Ala Gly Ala Arg Leu
                85              90              95

Asp Val Arg Asp Ala Trp Gly Arg Leu Pro Val Asp Leu Ala Glu Glu
            100             105             110

Leu Gly His Arg Asp Val Ala Arg Tyr Leu Arg Ala Ala Ala Gly Gly
        115             120             125

Thr Arg Gly Ser Asn His Ala Arg Ile Asp Ala Ala Glu Gly Pro Ser
130             135             140

Asp Ile Pro Asp
145
```

(2) INFORMATION FOR SEQ ID NO:25:

(i) SEQUENCE CHARACTERISTICS:
        (A) LENGTH: 138 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Met Arg Glu Glu Asn Lys Gly Met Pro Ser Gly Gly Gly Ser Asp Glu
1               5               10              15

Gly Leu Ala Ser Ala Ala Ala Arg Gly Leu Val Glu Lys Val Arg Gln
                20              25              30

Leu Leu Glu Ala Gly Ala Asp Pro Asn Gly Val Asn Arg Phe Gly Arg
            35              40              45

Arg Ala Ile Gln Val Met Met Met Gly Ser Ala Arg Val Ala Glu Leu
        50              55              60

Leu Leu Leu His Gly Ala Glu Pro Asn Cys Ala Asp Pro Ala Thr Leu
65              70              75              80

Thr Arg Pro Val His Asp Ala Ala Arg Glu Gly Phe Leu Asp Thr Leu
                85              90              95

Val Val Leu His Arg Ala Gly Ala Arg Leu Asp Val Arg Asp Ala Trp
            100             105             110

Gly Arg Leu Pro Val Asp Leu Ala Glu Glu Arg Gly His Arg Asp Val
        115             120             125

Ala Gly Tyr Leu Arg Thr Ala Thr Gly Asp
130             135
```